United States Patent
Pritzker et al.

(10) Patent No.: US 11,031,096 B2
(45) Date of Patent: Jun. 8, 2021

(54) METHOD FOR DETERMINING EFFICACY OF CHEMOTHERAPY TREATMENT FOR A SUBJECT

(71) Applicant: RNA DIAGNOSTICS INC., Toronto (CA)

(72) Inventors: Kenneth Pritzker, Toronto (CA); Amadeo Mark Parissenti, Sudbury (CA); Laura Pritzker, Toronto (CA); Mu Zhu, Waterloo (CA); Xiaohui Wang, Waterloo (CA); Stacey Santi, Copper Cliff (CA); Rashmi Narendrula, Sudbury (CA); Baoqing Guo, Sudbury (CA)

(73) Assignee: RNA DIAGNOSTICS INC., Toronto (CA)

( * ) Notice: Subject to any disclaimer, the term of this patent is extended or adjusted under 35 U.S.C. 154(b) by 785 days.

(21) Appl. No.: 14/396,309

(22) PCT Filed: Apr. 24, 2013

(86) PCT No.: PCT/CA2013/000408
§ 371 (c)(1),
(2) Date: Oct. 22, 2014

(87) PCT Pub. No.: WO2013/159200
PCT Pub. Date: Oct. 31, 2013

(65) Prior Publication Data
US 2015/0154350 A1 Jun. 4, 2015

Related U.S. Application Data

(60) Provisional application No. 61/637,676, filed on Apr. 24, 2012, provisional application No. 61/806,222, filed on Mar. 28, 2013.

(51) Int. Cl.
| G16B 25/00 | (2019.01) |
| C12Q 1/6886 | (2018.01) |
| C12Q 1/68 | (2018.01) |
| G01N 27/447 | (2006.01) |

(52) U.S. Cl.
CPC .............. G16B 25/00 (2019.02); C12Q 1/68 (2013.01); C12Q 1/6886 (2013.01); G01N 27/44791 (2013.01); C12Q 2600/142 (2013.01)

(58) Field of Classification Search
None
See application file for complete search history.

(56) References Cited

U.S. PATENT DOCUMENTS

| 6,251,247 B1 | 6/2001 | Mitsuhashi et al. |
| 7,197,401 B2 | 3/2007 | Hastings |
| 7,504,209 B2 | 3/2009 | Ingham et al. |
| 7,888,035 B2 | 2/2011 | Klass et al. |
| 7,968,291 B2 | 6/2011 | Brees et al. |
| 8,131,473 B1 | 3/2012 | Coffin et al. |
| 8,239,142 B2 * | 8/2012 | Collette ................ G16B 50/00 702/20 |
| 2003/0203408 A1 | 10/2003 | Williams et al. |
| 2006/0063170 A1 | 3/2006 | Erlander et al. |
| 2006/0166231 A1 | 7/2006 | Baker et al. |
| 2006/0246577 A1 | 11/2006 | Schroeder et al. |
| 2008/0318801 A1 | 12/2008 | Leung |
| 2010/0057371 A1 | 3/2010 | Denisov |
| 2010/0317001 A1 | 12/2010 | Parissenti et al. |
| 2014/0287063 A1 | 9/2014 | Parissenti et al. |
| 2015/0154350 A1 | 6/2015 | Pritzker et al. |
| 2015/0315656 A1 | 11/2015 | Zhu et al. |
| 2016/0077051 A1 | 3/2016 | Parissenti et al. |

FOREIGN PATENT DOCUMENTS

| AU | 2008295394 B2 | 3/2009 |
| EP | 1772522 | 4/2007 |
| JP | 5602018 B2 | 12/2010 |
| WO | 2004/090780 A2 | 3/2004 |
| WO | 2009030029 | 12/2009 |
| WO | 2013020201 | 2/2013 |

OTHER PUBLICATIONS

Schroeder et al. (BMC Molecular Biology2006, 7:3, pp. 1-14).*
Agilent Technologies (Agilent 2100 Bioanalyzer, Expert User's Guide, Copyright 2000, pp. 1-419) (Year: 2000).*
Agilent 2100 Bioanalyzer Protocol for RNA 6000 Nano LabChip kit, Jul. 2004 update.
Bulletin 5783 Rev A "Why choose the Experion Automated Eletrophoresis System From Bio-Rad?", Bio-Rad.
Oragene-RNA "Interpreting Bioanalyzer Results for RNA Collected Using Oragene-RNA", 2010 DNA Genotek, PD-WP-017 Issue 1.0.
Benner,"ChIP—Seq Analysis: Finding Peaks (ChIP-enriched Regions), retrieved from internet:" http://biowhat.ucsd.edu/homer/chipseq/peaks.html, retrieved on Mar. 26, 2012 12:34:41 PM.
Degradometer Version 1.4, Software Manual.
Denisov et al., RNA quality Indicator (RQI)—A New Tool for Assessing RNA Integrity to reliably detect differences in gene expression using qPCR experiments, BIO-RAD, poster.
Freed et al., When ribosomes go bad: diseases of ribosome biogenesis, Mol. BioSyst., 2010, 6, 481-493.

(Continued)

*Primary Examiner* — Pablo S Whaley
(74) *Attorney, Agent, or Firm* — Bereskin & Parr LLP/S.E.N.C.R.L., s.r.l.; Tony Orsi

(57) ABSTRACT

Various embodiments are described herein related to an assay, method and apparatus for performing an RNA Disruption Assay (RDA) for cellular RNA optionally in response to a cytotoxic treatment such as chemotherapy and/or radiation treatment. The method comprises obtaining at least one electropherogram dataset corresponding to a unique biological sample comprising the cellular RNA at a time point, optionally during or after the treatment; determining values for features from at least two shifted regions of the at least one electropherogram dataset, the shifting being due to the treatment; and optionally determining an RDA score based on a combination of the values of the features.

12 Claims, 45 Drawing Sheets

(56) References Cited

OTHER PUBLICATIONS

McArthur et al., Targeting Cell Cycle Checkpoints with Specific Inhibitor Drugs, http://www.petermac.org/Research/MolecularOncologyProjects. Accessed Mar. 26, 2012.
Kim et al., A robust peak detection method for RNA structure interference by high-throughput contact mapping, Bioinformatic.s, vol. 25, No. 9, 2009, pp. 1137-1144.
Yoon et al., HiTRACE: High-throughput robust analysis for capillary electrophoresis, Bioinformatics, vol. 00, No. 00 2011, pp. 1-13.
Hatzis et al., Effects of Tissue Handling on RNA Integrity and Microarray Measurements from Resected Breast Cancers, Mar. 21, 2012 104 (6), Abstract.
Denisov et al., Development and Validation of RQI: An RNA Quality Indicator for the Experion Automated Eletrophoresis System, Bulletin 5761, 2008 Bio-Rad Laboratories, Inc.
Belin et al., Dysregulation of Ribosome Biogenesis and Translational Capacity is Associated with Tumor Progression of Human Breast Cancer Cells, Sep. 2009, 4(9), e7147.
Agilent RNA 6000 Nano Kit Quick Start Guide, Agilent Technologies, Edition Apr. 2007.
Auer et al., Chipping away at the chip bias: RNA degradation in microarray analysis, Nature Genetics, Dec. 2003, 35(4):292-293.
Weigelt et al., "Gene expression profiles of primary breast tumors maintained in distant metastases", PNAS, Dec. 23, 2003, 100(26):15901-15905.
Hurvitz et al., "Final Analysis of a Phase II, 3-Arm, Randomized Trial of Neoadjuvant Trastuzumab or Lapatinib or the Combination of Trastuzumab and Lapatinib, Followed by 6 cycles of Docetaxel and Carboplatin with Trastuzumab and/or Lapatinib in Patients with HER2+ Breast Cancer (TRIO-US B07)", San Antonio Breast Cancer Symposium Cancer Therapy and Research Center at UT Health Science Center Dec. 10-14, 2013 (poster).
King, KL et al. 28S ribosime degradation in lymphoid cell apoptosis: evidence for caspase and BCL-2-dependent and-independent pathways. Cell Death and Differentiation, 2000, vol. 7, pp. 994-1001.
Neschadim Anton et al. Relaxin receptor antagonist AT-001 synergizes with docetaxel in androgen-independent prostate xenografts. Endocrine-Related Cancer, 2014, 21(3):459-71.
Martinet et al. Reactive oxygen species induce RNA damage in human atherosclerosis Introduction. European Journal of Clinical Investitgation. vol. 34, Issue 5, Jan. 1, 2004, pp. 323-327.
Tzu-Hsueh Yang et al. Determination of RNA degradation by capillary electrophoresis with cyan light-emited diode-induced flourescence. Journal of Chromatography. Elsevier Science Puglishers B.V., NL. vol. 1239, Mar. 21, 2012, pp. 78-84.
Best et al. Integrity of Prostatic Tissue for Molecular Analysis After Robotic-Assisted Laparoscopic and Open Prostatectomy. Urology, Belle Mead, NJ, US. vol. 70, No. 2, Aug. 1, 2007, pp. 328-332.
Wong et al., "Reduced Plasma RNA Integrity in Nasopharyngealcarcinoma Patients", Clinical Cancer Research, Apr. 15, 2006, 12:2512-2516, 12(8).
Parissenti A. M. et al., "Relationship of tumor RNA integrity to clinicopathologic parameters associated with epirubicin/docetaxel chemotherapy", 2007 Breast Cancer Symposium, Sep. 7 and 8, 2007, Abstract No. 107.
Parissenti A. M. et al., "Relationship of tumor RNA integrity to clinicopathologic parameters associated with epirubicin/docetaxel chemotherapy", 2007 Breast Cancer Symposium, Sep. 7 and 8, 2007, (Poster).
Parissenti A. M. et al., "Relationship of tumor RNA integrity to clinicopathologic parameters associated with epirubicin/docetaxel chemotherapy", Nov. 2007, Making Connections: A Canadian Cancer Research Conference Celebrating NCIC's 60th Anniversary, 203-204 (Abstract).
Pandey et al., Induction of the Interferon-Inductible RNA-Degrading Enzyme, RNase L, by Stree-Inducing Agents in the Human Cervical Carcinoma Cells, RNA Biology, May/Jun. 2004, pp. 21-27; 1:1.

Parissenti et al., "Reductions in Tumor RNA Integrity Associated with Clinical Response to Epirubicin/Docetaxel Chemotherapy in Breast Cancer Patients", Cancer Research 69 [Suppl 2], 378s, 2008.
Balatsos et al., "Drug action on poly(A) polymerase activity and isoforms during U937 cell apoptosis", Journal of Experimental and Clinical Cancer Research, Jan. 1, 2001, 20(1):63-69.
Ogston et al., "A new histological grading system to assess response of breast cancers to primary chemotherapy: Prognostic significance and survival", Breast, Oct. 2003, 12(5):320-327.
Carey et al., "Telomerase activity and prognosis in primary breast cancers", Journal of Clinical Oncology, Oct. 1999, 17(10):3075-3081.
Schroeder et al., "The RIN: an RNA integrity number for assigning integrity values to RNA measurements", BMC Molecular Biology, Biomed Central Ltd., Jan. 31, 2006, 7(1):3.
Imbeaud et al., "Towards standardization of RNA quality assessment using user-independent classifiers of microcapillary electrophoresis traces", Nucleic Acids Research, 2005, 33(6):e56, doi:10.1093/nar/gni054.
Wong et al. "Plasma RNA integrity analysis: methodology and validation", Annals of the New York Academy of Sciences, 2006, 1075:174-178.
Minotti et al., "Anthracyclines: molecular advances and pharmacologic developments in antitumor activity and cardiotoxicity", Pharmacol Rev, 2004, 56:185-229.
Parissenti A. M. et al., "Relationship of tumor RNA integrity to clinicopathologic parameters associated with epirubicin/docetaxel chemotherapy", Internet Citation, Sep. 7, 2007 (Sep. 7, 2007), pp. 1-4.
Strand, Carina et al. RNA quality in frozen breast cancer samples and the influence on gene expression analysis—a comparison of three evaluation methods using microcapillary electrophoreses traces. BMC Molecular Biology 2007, 8:38.
Houge, G., et al. Fine Mapping of 28S rRNA Sites Specifically Cleaved in Cells Undergoing Apoptosis. Molecular and Cellular Biology, Apr. 1995, vol. 15, No. 4, pp. 2051-2062.
Hoat, Trinh X., et al. Specific cleavage of ribosomal RNA and mRNA during victorin-induced apoptotic cell death in pat. The Plant Journal (2006) 46, pp. 922-933.
Marx, Vivien. RNA Quality: Defining the Good, the Bad, & the Ugly. Genomics Proteomics. Retrieved from Internet www.dnaarrays.org/P_GenProMag.pdf May 4, 2005.
King, KL et al. 28S ribosome degradation in lymphoid cell apoptosis: evidence for caspase and Bcl-2 dependent and independent pathways. Cell Death and Differentiation (2000) 7, 994-1001.
Fimognari, Carmela et al. Protective effect of creatine against RNA damage. Mutation Research 670 (2009) 59-67.
Fimognari, Carmela et al. Corrigendum to "Protective effect of creatine against RNA damage". Mutation Research. 670 (2009) 59-67.
Copois, Virginie et al. Impact of RNA degradation on gene expression profiles: Assessment of different methods to reliably determine RNA quality. Journal of Biotechnology 127 (2007) 549-559.
Banerjee et al., "RNase L-independent specific 28S rRNA cleavage in murine coronavirus-infected cells", Journal of Virology, Oct. 2000, pp. 8793-80, 74(19).
Parissenti et al., "Association of low tumor RNA integrity with response to chemotherapy in breast cancer patients", Breast Cancer Research and Treatment. Jan. 2010, pp. 347-56, 119(2), doi: 10.1007/s10549-009-0531-x.
Kemp et al., "p53 induction and apoptosis in response to radio- and chemotherapy in vivo is tumor-type-dependent", Cancer Research, Jan. 1, 2001, pp. 327-32, 61(1).
Kim et al., "The role of apoptosis in cancer cell survival and therapeutic outcome", Cancer Biology & Therapy, Nov. 2006, pp. 1429-1442, 5:11.
Raman et al., "Quality control in microarray assessment of gene expression in human airway epithelium", BMC Genomics, Oct. 24, 2009, 10:493, doi: 10.1186/1471-2164-10-493.
Samali et al., "The ability to cleave 28S ribosomal RNA during apoptosis is a cell-type dependent trait unrelated to DNA fragmentation", Cell Death and Differentiation, May 1997, pp. 289-93, 4(4).

(56) References Cited

OTHER PUBLICATIONS

Gjertsen, Bjorn Tore et al. Multiple apoptotic death types triggered through activation of separate pathways by cAMP and inhibitors of protein phosphatases in one (IPC leukemia) cell line. Journal of Cell Science 107, 3363-3677, 1994.
Greenhalgh D.A. et al. Effect of 5-fluorouracil combination therapy on RNA processing in human colonic carcinoma cells. Br. J. Cancer, 1990, vol. 61, pp. 415-419.
Thadani-Mulero, Maria et al. Androgen Receptor on the Move: Boarding the Microtubule Expressway to the Nucleus. Cancer Research, 72(18), pp. 4611-5, 2012.
Cheang, Maggie C. U., et al. Ki67 Index, HER2 Status, and Prognosis of Patients With Luminal B Breast Cancer. J. Natl. Cancer Institute, 2009, 101, pp. 736-750.
Goldhirsch A. et al. Strategies for subtypes—dealing with the diversity of breast cancer: highlights of the St Gallen International Expert Consensus on the Primary Therapy of Early Breast Cancer 2011. Annals of Oncology, vol. 22, pp. 1736-1747, 2011.
Narendrula, Rashmi. Quantitative and qualitative changes in cellular RBA in response of chemotherapy. Oral presentation, Apr. 4, 2012.
Johnson G.D. et al. "Cleavage of rRNA ensures translational cessation in sperm at fertilization, Molecular Human Reproduction", Aug. 2011, pp. 721-726, 17(12).
Fimognari et al., "RNA as a new target for toxic and protective agents", Mutation Research, Sep. 2008, pp. 15-22, 648(1-2).
Telli M. et al., "Insight or Confusion: Survival After Response-Guided Neoadjuvant Chemotherapy in Breast Cancer", Journal of Clinical Oncology, Oct. 2013 pp. 3613-3615, 31(29).
Young, L.E. Zeroing in on cancer. Laurentian University Magazine, Winter 2010, p. 5. Retrieved from the internet <URL:http://www.laurentian.ca/NR/rdonlyres/D6249D37-F645-49F1-8CA0-1EA940D81CB4/0/Winter10_English_low.pdf>.
Hannemann J. et al. Changes in Gene Expression Associated With Response to Neoadjuvant Chemotherapy in Breast Cancer, Journal of Clinical Oncology, May 2005, 3331-3342, 23(15).
Sotiriou et al. (200) Gene expression profiles derived from tine needle aspiration correlate with response to chemotherapy in breast cancer. Breast Cancer Research. 4:R3 (8 pages).
Thisted. (1998) What is a P-Value? The University of Chicago, p. 1-6.
Fleige et al. (2006) RNA integrity and the effect on the real-time qRT-PCR performance. Molecular Aspects of Medicine, 27:126-139.
Thuerigen et al. (2006). Gene Expression Signature Predicting Pathologic Complete R esponse with Gemcitabine, Epirubicin, and Docetaxel in Primary Breast Cancer, Journal of Clinical Oncology, 24(12):1839-1845.
Degen et al. (2000) Caspase-dependent cleavage of nucleic acids. Cell Death and Differentiation, 7:616-627.
Fulda et al. (2006) Extrinsic versus intrinsic apoptosis pathways in anticancer chemotherapy. Oncogene, 25:4798-4811.
Kaufman et al. (2000) Induction of Apoptosis by Cancer Chemotherapy. Experimental Cell Research, 256:42-49.
Toomey et al., "RE: RNA Disruption Assay as a Biomarker of Pathological Complete Response in Neoadjuvant Trastuzumab-Treated Human Epidermal Growth Factor Receptor 2—Positive Breast Cancer", JNCI, 2016, 108(8): djw111, pp. 1-2.
Trudeau, "Response", JNCI, 2016, 108(8): djw105, p. 1.
Mueller et al., "RNA Integrity Number (RIN)—Standardization of RNA Quality Control", Agilent Technologies, Inc., 2016, pp. 1-7.
Vespucci et al., "Agilent 2100 Bioanalyzer—2100 Expert Users Guide", Agilent Technologies, Inc., 2005, pp. 1-419.
Parissenti et al., "Tumor RNA disruption predicts survival benefit from breast cancer chemotherapy", Breast Cancer Res. Treat., 2015, 153(1): 135-144.
Olinski, R. et al. Epirubicin-induced oxidative DNA damage and evidence for its repair in lymphocytes of cancer patients who are undergoing chemotherapy, Mol.Pharmacol. 52 (1997) 882-885.

Vaishampayan, U. et al. Taxanes: an overview of the pharmacokinetics and pharmacodynamics, Urology 54 (1999) 22-29.
Morse, D.L. et al. Docetaxel induces cell death through mitotic catastrophe in human breast cancer cells, Mol.Cancer Ther. 4 (2005) 1495-1504.
Wieder, T. et al. Activation of caspase-8 in drug-induced apoptosis of B-lymphoid cells is independent of CD95/Fas receptor-ligand interaction and occurs downstream of caspase-3, Blood 97 (2001) 1378-1387.
Mueller, O. et al. RNA Integrity Number (RIN)—Standardization of RNA Quality Control. (2004).
Ganansia-Leymarie, V. et al. Signal transduction pathways of taxane-induced apoptosis. Curr Med. Chem Antica Ag 2003; 3: 291-306.
Cera, C. et al. Interaction between second generation anthracyclines and DNA in the nucleosomal structure, Nucleic Acids Res. 19 (1991) 2309-2314.
Spadari, S. et al. DNA polymerases and DNA topoisomerases as targets for the development of anticancer drugs, Anticancer Res. 6 (1986) 935-940.
Bachur, N.R. et al. Helicase inhibition by anthracycline anticancer agents, Mol.Pharmacol. 41 (1992) 993-998.
Honaas, Loren et al., A practical examination of RNA isolation methods for European pear (*Pyrus communis*). BMC Research Notes, 10:237, 2017. (DOI 10.1186/s13104-017-2564-2).
Jamshidi, Neema et al., Genomic Adequacy from Solid Tumor Core Needle Biopsies of ex Vivo Tissue and in Vivo Lung Masses: Prospective Study. Radiology, 2016.
Sellin Jeffries, Mario K. et al., A comparison of commercially-available automated and manual extraction kits for the isolation of total RNA from small tissue samples. BMC Biotechnology 2014, 14:94.
Kim, Jin-He et al., Comparison of three different kits for extraction of high-quality RNA from frozen blood. SpringerPlus 2014, 3:76.
Yu, Keke et al., Effect of multiple cycles of freeze—thawing on the RNA quality of lung cancer tissues. Cell Tissue Bank (2017) 18:433-440.
Unger, Conny et al., Ultraviolet C radiation influences the robustness of RNA integrity measurement. Electrophoresis 2015, 36, 2072-208.
Amundson, S.A. et al., Human in vivo radiation-induced biomarkers: gene expression changes in radiotherapy patients. Cancer Research, 64, 6368-6371, Sep. 15, 2004.
Shin, S. et al., Alteration of miRNA profiles by ionizing radiation in A549 human non-small cell lung cancer cells. International Journal of Oncology (2009) 35:81-86.
Burke, H. B. et al., Predicting response to adjuvant and radiation therapy in patients with early stage breast carcinoma. Cancer (1998), 82, pp. 874-877.
Formenti, S. C. et al., Low HER2/NEU gene expression is associated with pathological response to concurrent paclitaxel and radiation therapy in locally advanced breast cancer. Int. J. Radiation Oncology Biol. Phys., vol. 52, No. 2, pp. 397-405, 2002.
Xia, Fen and Powell, Simon N. The molecular basis of radiosensitivity and chemosensitivity in the treatment of breast cancer. Semin Radiat Oncol (2002), 12(4) 296-304. Abstract provided.
Hu, Ze-Ping et al. Metabolomic response of human skin tissue to low dose ionizing radiation. 2012, Mol BioSyst 8; 1979-1986. Abstract provided.
Delic, J. et al., 1993. "Gamma-ray induced transcription and apoptosis-associated loss of 28S rRNA in interphase human lymphocytes". Int J Radiat Biol 64; 39-46. Abstract provided.
Al-Mayah, A.H.J. et al., 2012. "Possible role of exosomes containing RNA in mediating nontargeted effect of ionizing radiation". Radiat Research 177; 539-545. Abstract provided.
Krolak, J.M. et al., 1989. "18S Ribosomal RNA is Degraded during Ribosome Maturation in Irradiated HeLa cells". Radiat Research 118; 330-340. Abstract provided.
Parissenti et al., Gene Expression Profiles as Biomarkers for the Prediction of Chemotherapy Drug Response in Human Tumor Cells, Anticancer Drugs 18(5) (Jun. 2007) 499-523.
Chang et al., Apoptosis and proliferation as predictors of chemotherapy response in patients with breast carcinoma. Cancer 2000, 89(11): 2145-52.

(56) References Cited

OTHER PUBLICATIONS

Archer, et al., Early changes in apoptosis and proliferation following primary chemotherapy for breast cancer. Br J Cancer 2003; 89(6): 1035-41.
Narla, et al. Ribosomopathies: human disorders of ribosome dysfunction. Blood 2010, Apr. 22. 115(16): 3196-205.
Burger, et al., Chemotherapeutic drugs inhibit ribosome biogenesis at various levels. The Journal of Biological chemistry Apr. 16, 2010; 285(16): 12416-25.
Crawford, et al., (1997) 16S mitochondrial ribosomal degradation is associated with apoptosis. Free Rad. Biol. Med. 22(7): 1295-1300.
Swe et al., (2000) zVAD-fmk and DEBD-cho induced late mitotic arrest and apoptotic expressions. Apoptosis 5(1): 29-36.
Cortazar et al. (2014) Pathological complete response and long-term clinical benefit in breast cancer: the CTNeoBC pooled analysis. Lancet vol. 384: 115-116.
Samkari, A., et al. Tumor RNA disruption as a tool to predict response to neoadjuvant chemotherapy in breast cancer: Optimizing timing of biopsy. (2016) Abstract No. P1-09-19 [abstract]. In: Proceedings of the 2016 San Antonio Breast Cancer Symposium; Dec. 6-10, 2016; San Antonio, TX. Philadelphia (PA): AACR; Cancer Res 2017; 77 (4 suppl): Abstract, 5 pages (Year: 2017).
Pritzker K., et al. RNA Disruption and Drug Response in Breast Cancer Primary Systemic Therapy. Journal of the National Cancer Institute, 2015, 51:76-80.
He, Kaiyu et al. Targets and Intracellular Signaling Mechanisms for Deoxynivalenol-Induced Ribosomal RNA Cleavage. Toxicological Sciences, 127(2), 382-390, 2012.
Scholl SM et al. Breast tumours response to primary chemotherapy predicts local and distant control as well as survival. Eur J Ca 1995; 31A: 1969-1995.
Curran W et al. Phase III comparison of sequential versus concurrent chemo-radiation for patients with unresected stage III non-small cell lung cancer (NSCLC): report of Radiation Oncology Group (RTOG) 9410. Lung Ca 2003; 29 (suppl 1): 93, abstract 303.
Bellon JR et al. Concurrent radiation therapy and paclitaxel or docetaxel chemotherapy in high-risk breast cancer. Int J Rad Onc Bio Phys 2000; 48: 393-397.
Chollet P et al. Clinical and pathological response to primary chemotherapy in operable breast cancer. Eur J Ca 1997; 33: 862-866.
Koukourakis MI et al. Weeky docetaxel and concomitant boost radiotherapy for non-small cell lung cancer. A phase I/II dose escalation trial. Eur J Ca 1998; 34: 838-844.
Onishi H et al. Concurrent two-dimensional radiotherapy and weekly docetaxel in the treatment of stage III non-small lung cancer: a good local response but no good survival due to radiation pneumonitis. Lung Ca 2003; 40: 79-84.
Adelstein DJ et al. An Intergroup phase III comparison of standard radiation therapy and two schedules of concurrent chemoradiotherapy in patients with unresectable squamous cell head and neck cancer. JCO 2003; 21: 92-98.
Rivera E, Mejia JA, Arun BK, Adinin RB, Walters RS, Brewster A et al. Phase 3 study comparing the use of docetaxel on an every-3-week versus weekly schedule in the treatment of metastatic breast cancer. Cancer 2008; 112 (7):1455-1461.
Bear HD et al. The effect on tumor response of adding sequential preoperative docetaxel to preoperative doxorubicin and cyclophosphamide: preliminary results from National Surgical Adjuvant Breast and Bowel Project protocol B-27. JCO 2003; 21: 4165-4174.
Bissery MC et al. Experimental antitumor activity of Taxotere (RP 56976, NCS 628503) a Taxol analogue. Ca Res 1991; 51: 4845-4852.
Kuerer HM, Newman LA, Smith TL, Ames FC, Hunt KK, Dhingra K et al. Clinical course of breast cancer patients with complete pathological primary tumor and axillary lymph node response to doxorubicin-based neoadjuvant chemotherapy. J Clin Oncol 1999; 17(2):460-469.

Forastiere AA et al. Concurrent chemotherapy and radiotherapy for organ preservation in advanced laryngeal cancer. NEJM 2003; 349: 2091-2098.
Denis F et al. Final results of the 94-01 French Head and Neck Oncology and Radiotherapy Group randomized trial comparing radiotherapy alone with concomitant radiochemotherapy in advanced-stage oropharynx carcinoma. JCO 2004; 22: 69-76.
Bosset JF et al. Chemotherapy with preoperative radiotherapy in rectal cancer. NEJM 2006; 355: 1114-1123.
Formenti SS, Dunnington G, Uzieli B, Lenz H, Keren-Rosenberg S, Silberman H et al. Original p53 status predicts for pathological response in locally advanced breast cancer patients treated preoperatively with continuous infusion 5-fluorouracil and radiation therapy. Int J Radiat Oncol Biol Phys 1997; 39(5):1059-1068.
Djuzenova CS, et al. Radiosensitivity in breast cancer assessed by the histone y-H2AX and 53BP1 foci. Radiation Oncology 8:98.
Formenti SC et al. Preoperative twice-weekly paclitaxel with concurrent radiation therapy followed by surgery and postoperative doxorubicin-based chemotherapy in locally advanced breast cancer: a phase I/II trial. JCO 2003; 21: 864-870.
Gazet JC et al. Assessment of the effect of pretreatment with neoadjuvant therapy on primary breast cancer. Br J Ca 1996; 73: 758-762.
Johung et al. A clinical model for identifying radiosensitive tumor genotypes in non-small cell lung cancer 2013 Clin Cancer Res. 19(22).
Martin M et al. Adjuvant docetaxel for node-positive breast cancer. NEJM 2005; 352: 2302-2313.
Mueller, O. et al., A microfluidic system for high-speed reproducible DNA sizing and quantitation. Electrophoresis 21 (2000) 128-134.
Hutcheon AW et al. Improvements in survival in patients receiving primary chemotherapy with docetaxel for breast cancer: a randomized controlled trial. Br Ca Res Tr 2001; 69: 298.
Nabholtz JM et al. Docetaxel and doxorubicin compared with docetaxel and cyclophosphamide as first-line chemotherapy for metastatic breast cancer: results of a randomized, multicenter phase III trial. JCO 2003; 21: 968-975.
Ravdin PM et al. Phase II trial of docetaxel in advanced anthracycline-resistant or anthracenedione-resistant breast cancer. JCO 1995; 13: 2879-2885.
Mauer AM et al. Phase I study of docetaxel with concomitant thoracic radiation therapy. JCO 1998; 16: 159-164.
O'Shaughnessy J et al. Superior survival with capecitabine plus docetaxel combination therapy in anthracycline-pretreated patients with advanced breast cancer; phase III trial results. JCO 2002; 20: 2812-2823.
Valero V et al. Phase II trial of docetaxel: a new highly effective antineoplastic agent in the management of patients with anthracycline-resistant metastatic breast cancer. JCO 1995; 13: 2886-2894.
Nature. Comprehensive molecular portraits of human breast tumours. 490:61-70, Oct. 4, 2012.
Chan S et al. Prospective randomized trial of docetaxel versus doxorubicin in patients with metastatic breast cancer. The 303 Study Group. JCO 1999; 17: 2341-2354.
Posner MR et al. Cisplatin and Fluorouracil alone or with docetaxel in head and neck cancer. NEJM 2007; 357: 1705-1715.
Rodel C et al. Prognostic significance of tumor regression after preoperative chemoradiotherapy for rectal cancer. JCO 2005; 23: 8688-8696.
Sauer R et al. Preoperative versus postoperative chemoradiotherapy for rectal cancer. NEJM 2004; 351: 1731-1740.
Ruyck et al. TGFR1 polymorphisms and late clinical radiosensitivity in patients treated for gynecologic tumors. Int. J. Radiation Oncol.Biol Phys. 2006. 65: 1240.
Roche H et al. Sequential adjuvant epirubicin-based and docetaxel chemotherapy for node-positive breast cancer patients; the FNCLCC PACS 01 trial. JCO 2006; 24: 5664-5671.
Smith IC et al. Neoadjuvant chemotherapy in breast cancer significantly enhanced response with docetaxel. JCO 2002; 20: 1456-1466.
Tabernero J, Climent MA, Lluch A, Albanell J, Vermorken JB, Barnadas A et al. A multicentre, randomised phase II study of

(56) References Cited

OTHER PUBLICATIONS weekly or 3-weekly docetaxel in patients with metastatic breast cancer. Ann Oncol 2004; 15(9):1358-1365.
Von Minckwitz G et al. Doxorubicin with cyclophosphamide followed by docetaxel every 21 days compared with doxorubicin and docetaxel every 14 days as preoperative treatment in operable breast cancer: the GEPARDUO study of the German Breast Group. JCO 2005; 23: 2676-2685.
Handbook, Qiagen. Sample & Assay Technologies, "RNeasy® MinElute® Cleanup Handbook: For RNA cleanup and concentration with small elution volumes", Oct. 1, 2010, pp. 1-32.

\* cited by examiner

Minimum 18S/Total Area

Max Intermediate/28S

Effect of Radiation on RNA Disruption in A2780 Cells

METHOD FOR DETERMINING EFFICACY OF CHEMOTHERAPY TREATMENT FOR A SUBJECT

FIELD

The various embodiments described herein generally relate to assays, methods and apparatus for assessing RNA disruption optionally in response to a cytotoxic treatment optionally chemotherapy and/or radiation therapy.

BACKGROUND

Ribonucleic acids (RNA) are biopolymers which encode genetic information and play various roles in a cell, including encoding proteins. RNA preparations are employed in the investigation of gene expression, for example, by microarray experiments, RT-PCR and many other methods. The results of experiments employing RNA preparations and the significance of results obtained by such experiments, is largely dependent upon the integrity of the RNA employed. Different methods are available to measure RNA integrity of a sample. Typically the methods compare heat degraded or RNAse degraded samples to samples with intact RNA with regard to the capacity of the RNA at a particular degradation level to be sufficiently intact to permit PCR amplification of specific mRNAs such as "housekeeping' genes.

For example, Schroeder, A., O. Mueller, et al. (2006) describes a method that automatically selects features from signal measurements and constructs regression models based on a Bayesian learning technique. Feature spaces of different dimensionality are compared in the Bayesian framework, which allows selecting a final feature combination corresponding to models with high posterior probability. The approach was applied to a large collection of electrophoretic RNA measurements recorded with an Agilent 2100 bioanalyzer to develop an algorithm that describes RNA integrity. The resulting algorithm is a user-independent, automated and reliable procedure for standardization of RNA quality control that allows the calculation of an RNA integrity number (RIN) under certain conditions and/or for certain samples.

A method of using tumour RNA integrity to measure response to chemotherapy in cancer patients is disclosed in PCT/CA2008/001561 filed Sep. 5, 2008.

SUMMARY OF VARIOUS EMBODIMENTS

In one aspect, in at least one embodiment described herein, there is provided a method for performing an RNA Disruption Assay (RDA) for cellular RNA optionally in response to a cytotoxic treatment optionally a treatment for a proliferative disorder optionally a cancer treatment, optionally chemotherapy, adjuvant or radiation treatment. The method comprises obtaining at least one electropherogram dataset corresponding to a unique biological sample comprising cellular RNA optionally at a time point before, during or after the treatment; determining values for features from the at least one electropherogram dataset by using two identifying ranges to accommodate possible shifting of 18S and 28S peaks, detecting the 18S and 28S peaks, and calculating the features derived at least in part based on the located 18S and 28S peaks; and optionally determining an RDA score based on a combination of the values of the features.

In one aspect, in at least one embodiment described herein, there is provided a method for performing an RNA Disruption Assay (RDA) for cellular RNA response to a cytotoxic treatment optionally chemotherapy treatment and/or radiation treatment. The method comprises obtaining at least one electropherogram dataset corresponding to a unique biological sample comprising cellular RNA at a time point before, during or after the treatment; determining values for features from at least two shifted regions of the at least one electropherogram dataset, the shifting being due to the treatment; and optionally determining an RDA score based on a combination of the values of the features.

In another aspect, in at least one embodiment described herein, there is provided an assay comprising: quantifying the amount of RNA disruption in a biological sample comprising cellular RNA at a time point before, during or after cytotoxic treatment, optionally a cancer treatment, optionally chemotherapeutic, adjuvant and/or radiation treatment, using an RNA disruption assay (RDA) performed according to the method for performing RDA described herein; and determining if the amount of RNA disruption of the cellular RNA is increased or not increased.

In another aspect, in at least one embodiment described herein, there is provided an in vitro assay for determining sensitivity to a cytotoxic treatment optionally a cancer treatment e.g. chemosensitivity of cells to a chemotherapeutic treatment and/or optionally radiosensitivity of cells to a radiation treatment. The assay comprises quantifying the amount of RNA disruption in a biological sample comprising cell RNA at a time point before, during or after treatment using an RNA Disruption Assay (RDA) performed according to the method for performing RDA described herein; and comparing the quantified amount of RNA disruption with a threshold or reference value, and if the amount of RNA disruption is increased relative to the reference value, identifying the cell as sensitive (e.g. chemosensitive and/or radiosensitive) to the treatment and if not increased identifying the cells as resistant to the treatment.

In another aspect, in at least one embodiment described herein, there is provided an assay for determining if a subject is responding to a cytotoxic therapy, optionally a cancer therapy, optionally a chemotherapeutic drug and/or radiation treatment comprising: assaying a biological sample obtained from the subject before, during and/or after the subject has received the treatment e.g. chemotherapeutic and/or radiation treatment for the quantity of RNA disruption using an RNA Disruption Assay (RDA) performed according to the method for performing RDA described herein, wherein the subject is identified as responding to the treatment if the quantity of RNA disruption is increased relative to the threshold or reference value.

In another aspect, in at least one embodiment described herein, there is provided a method of treating a subject in need of cancer treatment comprising administering a cancer treatment, optionally a chemotherapeutic drug, adjuvant and/or radiation; determining if the subject is responding to the treatment according to the RDA method described herein; and continuing administration of the treatment if the subject is responsive; and/or altering and/or discontinuing administration of the treatment if the subject is not responsive.

In another aspect, in at least one embodiment described herein, there is provided a non-transitory computer readable medium comprising a plurality of instructions executable on a microprocessor of an apparatus for adapting the apparatus to implement a method for performing an RNA Disruption Assay (RDA) for cellular RNA optionally for a proliferative disorder optionally a cancer treatment, optionally chemotherapy, adjuvant and/or radiation treatment. The method comprises accessing at least one electropherogram dataset corresponding to a unique biological sample comprising cellular RNA at a time point before, during or after the treatment; determining values for features from the at least one electropherogram dataset by using two identifying regions to accommodate possible shifting of 18S and 28S peaks, detecting the 18S and 28S peaks, and calculating the features derived in part based on the located 18S and 28S peaks; and optionally determining an RDA score based on a combination of the values of the features.

In another aspect, in at least one embodiment described herein, there is provided an apparatus for performing an RNA Disruption Assay (RDA) for cellular RNA optionally a treatment for a proliferative disorder optionally a cancer treatment, optionally chemotherapy, adjuvant or radiation treatment. The apparatus comprises a data input to receive at least one electropherogram dataset corresponding to a unique biological sample comprising cellular RNA at a time point before, during or after the treatment; a processing unit coupled to the data input, the processing unit being configured to determine values for features from the at least one electropherogram dataset by using two identifying ranges to accommodate possible shifting of 18S and 28S peaks, detecting the 18S and 28S peaks, and calculating the features derived at least in part based on the located 18S and 28S peaks; and a data output coupled to the processing unit to convey an indication of the RDA score.

In another aspect, in at least one embodiment described herein, there is provided an apparatus for performing an RNA Disruption Assay (RDA) for cellular RNA optionally a treatment of a proliferative disorder optionally a cancer treatment, optionally chemotherapy, adjuvant or radiation treatment. The apparatus comprises means for obtaining at least one electropherogram dataset corresponding to a unique biological sample comprising cellular RNA at a time point before, during or after the treatment; means for determining values for features from the at least one electropherogram dataset by using two identifying ranges to accommodate possible shifting of 18S and 28S peaks, detecting the 18S and 28S peaks, and calculating the features derived at least in part based on the located 18S and 28S peaks; and means for determining an RDA score based on a combination of the values of the features.

In another aspect, in at least one embodiment described herein, there is provided a method for performing an RNA Disruption Assay (RDA) for cellular RNA. The method comprises obtaining at least one electropherogram dataset corresponding to a unique biological sample comprising the cellular RNA at a time point; defining an 18S peak and a 28S peak from the at least one electropherogram dataset; determining at least one parameter value for both the 18S peak and the 28S peak; redefining at least one of the 18S peak and the 28S peak when required according to one or more rules applied to the at least one parameter value; determining an 18S peak area and a 28S peak area; and determining an RDA score based on at least one of the 18S peak area and the 28S peak area.

In another aspect, in at least one embodiment described herein, there is provided a method for performing an RNA Disruption Assay (RDA) for cellular RNA. The method comprises obtaining at least one electropherogram dataset corresponding to a unique biological sample comprising the cellular RNA at a time point; defining an 18S peak and a 28S peak from the at least one electropherogram dataset; determining at least one parameter value for both the 18S peak and the 28S peak; and redefining at least one of the 18S peak and the 28S peak when required according to one or more rules applied to the at least one parameter value.

In another aspect, in at least one embodiment described herein, there is provided a non-transitory computer readable medium comprising a plurality of instructions executable on a microprocessor of an apparatus for adapting the apparatus to implement a method for performing an RNA Disruption Assay (RDA) for cellular RNA. The method comprises: obtaining at least one electropherogram dataset corresponding to a unique biological sample comprising the cellular RNA at a time point; defining an 18S peak and a 28S peak from the at least one electropherogram dataset; determining at least one parameter value for both the 18S peak and the 28S peak; and redefining at least one of the 18S peak and the 28S peak when required according to one or more rules applied to the at least one parameter value.

In another aspect, in at least one embodiment described herein, there is provided an apparatus for performing an RNA Disruption Assay (RDA) for cellular RNA. The apparatus comprises a data input to receive at least one electropherogram dataset corresponding to a unique biological sample comprising cellular RNA at a time point; a processing unit coupled to the data input, the processing unit being configured to define an 18S peak and a 28S peak from the at least one electropherogram dataset; determine at least one parameter value for both the 18S peak and the 28S peak; and redefine at least one of the 18S peak and the 28S peak when required according to one or more rules applied to the at least one parameter value; and a data output coupled to the processing unit to convey an indication of the RDA.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and in which.

DETAILED DESCRIPTION OF THE EMBODIMENTS

Figure 1:
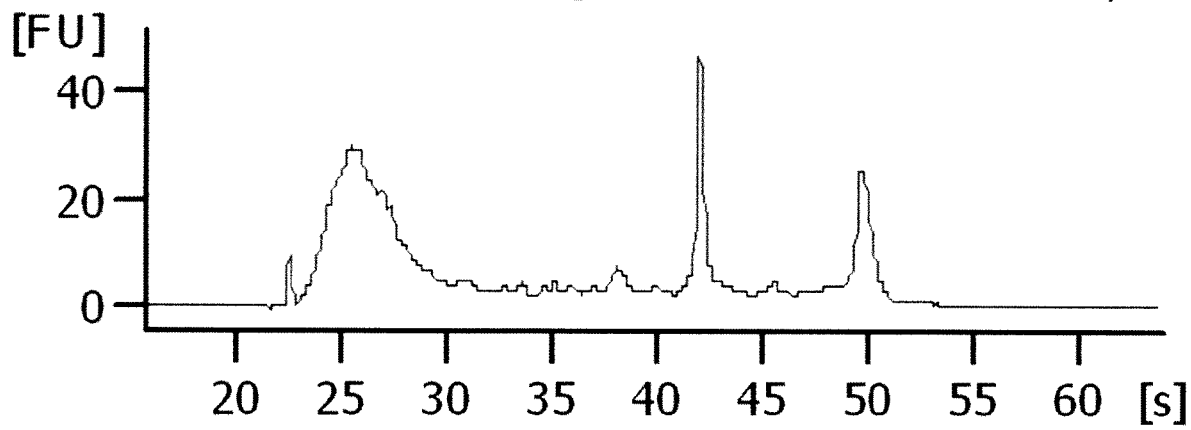
FIG. 1 is an illustration of an electropherogram trace of RNA isolated from a punch biopsy of a MCF-7 tumour xenograft that has been kept at room temperature in saline for 24 hours where autolytic degradation takes place.

Various assays, methods or apparatuses will be described below to provide an example of an embodiment of each claimed invention. No embodiment described below limits any claimed invention and any claimed invention may cover processes or apparatuses that differ from those described below. The claimed inventions are not limited to apparatuses or processes having all of the features of any one apparatus or process described below or to features common to multiple or all of the apparatuses or processes described below. It is possible that an apparatus or process described below is not an embodiment of any claimed invention. Any invention disclosed in an apparatus or process described below that is not claimed in this document may be the subject matter of another protective instrument, for example, a continuing patent application, and the applicants, inventors or owners do not intend to abandon, disclaim or dedicate to the public any such invention by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

I. DEFINITIONS

The term "coupled" used herein indicates that two elements can be directly coupled to one another or coupled to one another through one or more intermediate elements.

The term "autolytic RNA degradation" as used herein refers to RNA degradation taking place during autolytic cell destruction. Autolysis is initiated, for example, by the cells' lysosomes releasing digestive enzymes into the cytoplasm due to the cessation of active processes in the cell, and not due to an active physiologic or pathophysiologic process. Autolytic RNA degradation in a sample can be induced by removal of cells from physiologic environment for extended period of time (e.g. incubation in saline) and/or nonspecific cessation of physiologic processes e.g. heat treatment.

The term "RNA disruption" as used herein refers to discretely fragmented and/or degraded RNA that is signal induced in response to a cytotoxic treatment such as a drug treatment, e.g. chemotherapy, radiation treatment, and/or cytotoxic antibody treatment (e.g. Trastuzumab). Cytotoxic signal induced RNA disruption can include RNA degradation that has some features that resemble autolytic degradation, particularly for example during later stages.

The term "subject" as used herein refers to any member of the animal kingdom, preferably a human being including, for example, a subject that has or is suspected of having a proliferative disorder such as cancer.

The term "control" as used herein refers to a comparator such as intact RNA, a pretreatment sample(s) from a subject or group of individuals with a known outcome and/or a value corresponding to or derived from such samples. With respect to methods for assessing treatment outcome, the control can be a reference value such as a baseline amount or a median or average pretreatment amount of RNA degradation for a particular cell or cancerous tumour. The control can be a sample from a subject or subjects who are known as responding or not responding to a cytotoxic treatment such as a cancer treatment e.g. chemotherapeutic and/or radiation treatment or a value determinable from such samples, such as one or more threshold values above which or below which (depending on how the threshold or measurement is defined) identifies the likelihood that a sample has disrupted RNA, or that a subject or disease is responsive to the cytotoxic treatment e.g. that the tumour is responsive to a chemotherapeutic treatment. The control can also be more than one control, such as a series of threshold values that define clinical zones for a known outcome group of subjects, wherein each zone is associated with a likely response. Untreated cells (e.g. cells pretreatment) from many cells types or, for example, from pretreated tumour samples can have a high RNA integrity. Accordingly, the control can, for example, be a pretreatment value derived from one or more pretreatment samples. As described below, subjects in the MA22 study with mid-treatment tumour values above a threshold (e.g. which exhibited increased degradation) correlated with a pathologic complete response within the breast and axilla post-treatment.

The term "internal standard" as used herein means an RNA sample that is used as a normalizer for a particular assay. For example, when the assay comprises using an RNA chip, the internal standard can be the sample that is determined as having the smallest value for the measure: (intermediate area+low B area+low C area)/(28S area+18S area). The internal standard can be used to identify which samples are adjusted. The internal standard can be a subject sample and/or a control sample.

The term "baseline amount" as used herein refers to an amount of RNA degradation (e.g. RNA disruption and/or autocatalytic RNA degradation) in a sample such as a pretreatment sample that is used for comparison to a test sample (e.g. comparison to a cell population and/or tumour) taken at a later time point, for example during or after treatment e.g. during or after a treatment regimen comprising chemotherapy, cytotoxic antibody and/or radiation treatment. For example, in methods related to monitoring response to treatment, "base-line amount" can refer to a level of RNA degradation in a sample taken prior to a subsequent sample, e.g. a base-line sample is taken before treatment, the comparison to which provides an indication of response to treatment.

The term "amount" as used herein with respect to RNA degradation (e.g. disruption) refers to an amount (e.g. relative amount or absolute amount) of RNA degradation/disruption that is detectable or measurable in RNA isolated from a sample, for example, using an RDA assay described herein. For example, the amount can be expressed using an absolute value (e.g. an RDI value) or a relative amount such as 1.2, 1.3, 1.4, 1.5, 1.6, 1.7, 1.8, 1.9, 2.0, 2.2, 2.4, 2.6, 2.8, 3.0, 3.2, 3.4, 3.6, 3.8, 4.0, 4.2, 4.4, 4.6, 4.8, 5.0, 10, 15, 20, 25, 30, 40, 60, 80 and/or 100 times a control amount, where for example, the control amount is, for example, a pretreatment amount or, for example, a reference value corresponding to the average or median level in untreated or pretreatment samples. The amount can be compared to a threshold value which identifies subjects with a likelihood of responding to the treatment.

The term "threshold value" with respect to discriminating subject outcome also referred to as "cut-off" or "cut-off value" as used herein refers to a value which is derived from a population of samples with known outcomes and identifies a clinical zone boundary (e.g. RDA zone) for a selected specificity and/or sensitivity. Multiple threshold values defining multiple clinical zone boundaries can be employed. The zone boundaries define clinical zones and subjects having an RDA score (e.g. an RDI) falling within a RDA zone are identified as having an increased likelihood of responding or not responding to a particular cytotoxic treatment e.g. chemotherapeutic and/or radiation treatment, defined by the zone. For example, the threshold value can be the highest value associated with a panel of known outcome patients (e.g. 100% specificity) or a median level or other selected level, for example, as calculated according to one of the Examples described herein. A subject with an RDI score above the threshold value or falling within a zone specified as being below one threshold value or between two threshold values or above a second threshold value is predicted for example to be likely responding to the treatment, indeterminate or likely not responding to the treatment. The threshold value can be derived, for example, from a database of a plurality of samples.

The terms "18S" and "28S" generally refer to the 18S peak area and the 28S peak area, respectively, unless these terms are modified by other words such as peak or width or band (which can refer to the 18S and 28S bands separated on a gel). Accordingly, the terms "18S peak" and "28S peak" represent the heights of the 18S and 28S peaks respectively. Furthermore, the terms 18S width and 28S width represent the widths of the 18S and 28S peaks respectively. Once a peak is located, the peak width and the peak height are determined according to certain methods described herein. For example, the peak width may be defined by the subtraction of the starting time of the peak from the ending time of the peak. Another example is that the peak height may be defined as the absolute value of the highest point in a peak region or band.

The term "specificity" as used herein refers to the percentage of subjects that are responding to a treatment that are identified as not responding to the treatment based on a RNA disruption score that is, for example, at or below a control level and/or a cut-off level.

The term "sensitivity" as used herein refers to the percentage of subjects that are responsive that are identified as responding to the treatment based on a RNA disruption assay score, that is, for example, above a control amount and/or threshold value.

The term "sample" as used herein refers to 1) any biological fluid, cell or tissue sample from a subject (e.g. test subject) or cell line that comprises cellular RNA, optionally tumour tissue/cells and/or 2) RNA derived from such a sample. For example, the sample can be a biopsy, including a needle aspirate, such as a fine needle aspirate, a core biopsy, a brush biopsy and/or a laparoscopic biopsy. The sample can, for example, be a "post-treatment" sample wherein the sample is obtained after one or more cytotoxic, e.g. cancer treatments, or a "base-line sample" which is optionally pre-treatment or taken at an earlier time-point than the post-treatment sample, and is for example, used as a base line for assessing or monitoring response to a cytotoxic treatment. The tumour tissue/cells can be any tissue or cells, for example cancerous tissue or cells, for example ovarian cancer, prostate cancer, lung cancer, sarcomas, leukemia, lymphoma or multiple myeloma or colon cancer and/or any cancer for example cancers treatable by an anthracycline and/or taxane, including any subtype thereof including, for example, HER2+/−, ER+/−, PR+/−, topoisomerase+/− or triple negative breast cancer.

The term "RNA disruption assay score" or "RDA score" as used herein is a score or measure indicative of the extent of RNA degradation and/or likelihood of response to treatment, assessed on the basis of an RNA disruption assay described herein. The RDA score can for example be the output of a calculation based on electropherogram features described herein, for example represented as an RNA Disruption Index (RDI), which is described below, or can be a transformed scale, defined by clinical RDA zones based on cut-offs or thresholds, wherein each score or RDA zone is associated with a likelihood of a response for example associated with a likelihood of responsive to a treatment, for example defined by NPV and/or PPV. In an embodiment, a high or increased RNA disruption assay score (for example compared to a baseline sample or control) is indicative of high or increased RNA disruption. For example in such an embodiment, the higher the RNA disruption score, the greater the RNA disruption (and a decrease in RNA integrity). Any scale can be employed, for example 3, 10, or 600. A person skilled in the art would recognize that the scale could also be inverted (for example, by dividing the score into 1, e.g. 1/RNA score) such that the lower the RNA disruption score, the greater the RNA disruption.

The term "RDA zones" as used herein refers to clinical zones associated with treatment response outcome comprising a range of RNA disruption scores, for example RDI values. Each RDA zone is defined by one or two boundaries each boundary corresponding to a selected threshold (e.g. corresponding to a desired NPV or PPV). Subject RDA scores (optionally RDI values) that fall within the clinical zones that are associated with or are predictive of treatment response, for example pCR. In the Examples, 3 RNA disruption assay zones are used, RDA zone 1, RDA zone 2 and RDA zone 3, defined by selected NPV and/or PPVs. A person skilled in the art would readily realize that any number of zones can be used each with different selected thresholds.

The term RNA Disruption Index "RDI" as used herein is a value generated using RDA and can be a ratio of features defined herein of the output of LDA or quadratic discriminant analysis of features described herein. The RDI values determined from a group of known response outcome patients (e.g. that are determined to be associated with a particular NPV or PPV) can be used to define the thresholds boundary for RDA zones.

The term "RDA zone 1" as used herein refers to a range of RDA scores (e.g. RDI values) that have a negative predictive value (NPV) of at least 0.8, at least 0.85, at least 0.9, at least 0.95, at least 0.96, at least 0.97, at least 0.98 or greater. These numbers and the associated thresholds, are for example based on the pCR in the Ma-22 data set and RDA measurement at third cycle used in the Examples. In an example embodiment, RDA Zone 1 is equal to an RDI of equal or less than 10 calculated using the feature Intermediate Area/(28S+18S Areas). In other embodiments, other features or combination of features can be used. The "RDA zone 1" can be defined to include any set of scores by selecting the desired NPV.

The term "RDA zone 2" as used herein refers to a range of RDA scores (e.g. RDI values) falling between RDA zone 1 and 3, and can be considered an intermediate or indeterminate zone.

The term "RDA zone 3" as used herein refers to a range of RDA scores (e.g. RDI values) that have a positive predictive value (PPV) of at least 0.15, at least 0.16, at least 0.17, at least 0.18, at least 0.19, at least 0.2 or greater. These numbers and the associated thresholds are for example based on the pCR in the Ma-22 data set and RDA measurement at third cycle used in the Examples. The "RDA zone 3" can be defined to include any set of scores by selecting the desired PPV.

The term "response", "responding" or "responsive" as used herein refers to a cell such as a cancerous cell or tumor response to a cytotoxic treatment such as a chemotherapeutic and/or radiation treatment, where the cells for example cancer cells or a subset of cancer cells within a tumour respond to the treatment in terms of RNA disruption—e.g. in the context of a subject, the cells show significant treatment induced RNA degradation, and the subject has a positive treatment outcome, for example, reduction of tumour burden, disease stabilization, improved survival such as disease free survival and/or pathological complete response. In an embodiment, a subject who responds to a cytotoxic treatment with for example, one or more of a reduction of tumour burden, disease stabilization, improved survival such as disease free survival and/or pathological complete response, is considered, a "Responder" and/or a subject who does not for example, exhibit reduction in one or more of tumour burden, disease stabilization, improved survival such as disease free survival and/or pathological complete response is considered a "Non-Responder".

The term "resistant" as used herein in reference to a cell such as a cancerous cell or tumour, refers to a cell or tumour response to a cytotoxic treatment, where the cells, e.g. cancer cells or subset of cancer cells within the tumour show no or little response to the treatment in terms of RNA disruption and a negative treatment outcome, for example disease progression and/or a lack of treatment benefit for the subject having the cancerous tumour.

The term "decreased RNA concentration" as used herein means an RNA concentration that is at least 20%, at least 25%, at least 30%, at least 40%, at least 50%, at least 60%, at least 70%, at least 80% or at least 90% less than a control or corresponding reference value for example a pretreatment sample or for example a maximal value. RNA concentration can be determined by a number of methods including for example microcapillary electrophoresis, for example using for example an Agilent Bioanalyzer machine, an Experion® Capillary Electrophoresis System with its equivalent RNA Quality Index (RQI), Nanodrop® (Thermo Scientific, Inc.) or other equivalent systems, such as those manufactured by Applied Biosystems, Lumex, or Beckman Coulter Corporation or similar system. The RNA concentration can be based on UV absorbance, for example by assessing UV absorbance at 260 nm.

The term "low risk" as used in relation to progression refers to risk sufficiently less than average risk (e.g. decreased probability) calculated for a group of patients for example with the same cancer, treated similarly such that the patients would have high probability of survival with conservative therapy; and high risk of progression means greater than average risk (e.g. increased probability) compared to the low risk group of patients.

The term "stable RNA integrity" or "lack of RNA disruption" as used herein means RNA that is not degraded appreciably, for example as compared to an appropriate comparator sample or the expected RNA integrity for the cell type of tissue, for example, less than a 10% decrease in integrity or less than a 15% decrease in integrity.

The term "RNA isolating or stabilizing composition" as used herein refers to any composition that inhibits RNAse activity sufficiently and/or stabilizes RNA preventing RNA degradation.

The term "RNA integrity" as used herein means the degree of intactness of the RNA following extraction or isolation from the cell or tissue e.g. whether the isolated RNA is degraded (e.g. disrupted and/or autolytically degraded). High RNA integrity is commonly taken as meaning little to no degradation, for example less than a 30%, less than 25%, less than 20% or less than 10% decrease from a maximal RNA integrity and/or control sample or the retention of capacity to amplify mRNAs of interest following extraction or isolation. Low integrity RNA is, for example, RNA that exhibits greater than 20%, greater than 25%, greater than 30%, greater than 35%, greater than 40%, greater than 45%, greater than 50%, greater than 55%, greater than 60%, greater than 65%, greater than 70%, or greater than 75% decrease from maximal and/or a control sample or decreased capacity to amplify mRNAs of interest when they are known to be present in controls in RNA following extraction or isolation. RNA integrity can also be represented as an absolute number. For example, one RNA integrity scale assigns a number from 1 to 600 wherein an increasing score is associated with greater RNA disruption/ degradation. For example, a sample that comprises a score of 500 comprises more RNA degradation than a sample scoring 400.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, reversal of disease, amelioration or palliation of the disease state, and remission (whether partial or total), whether detectable or undetectable. "Treatment" can also mean prolonging survival as compared to expected survival if not receiving treatment.

The term "signal induced cytotoxic treatment" as used herein means any agent or radiation that can induce cell death that is used in the treatment of disease for example cancer, including for example, traditional and non-traditional chemotherapy (e.g. targeted therapies), radiation treatment, hormonal treatment (e.g. for responsive cancers) and combinations thereof. Such agents include but are not limited to microtubule stabilizing agents such as Docetaxel and paclitaxel, DNA synthesis inhibitors such Epirubicin, inhibitors of Her2 Receptor such as Trastuzumab, DNA cross-linking agents such as Mafosfamide, carboplatin and cisplatin, VEGFA inhibitors such as Bevacizumab, Receptor Tyrosine Kinase inhibitors such as Sunitinib and Toceranib, Bisphosphonates such as Zoledronic acid, Thymidylate synthase inhibitors such as 5-fluorouracil.

The term "radiation" in relation to a treatment means any energy, photon or particle, applied to a tumour, including for example ionizing radiation.

The term "dose" as used herein in reference to radiation refers to an individual radiation exposure either administered at each time within a schedule or the total amount of radiation exposure within a schedule. With respect to a chemotherapy treatment, a dose means an amount of an individual drug either administered at each time within a schedule or the total amount of each drug administered within a schedule or the total amount of drug administered during a course of chemotherapy.

The term "changing cancer treatment" or "altering cancer treatment" as used herein includes for example one or more of changing the dosage level of the radiation, discontinuing the treatment, adding a chemotherapeutic agent(s) to the treatment or changing to an alternate cancer treatment such as a drug therapy or surgery.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

In understanding the scope of the present disclosure, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

In understanding the scope of the present disclosure, the term "consisting" and its derivatives, as used herein, are intended to be close ended terms that specify the presence of stated features, elements, components, groups, integers, and/or steps, and also exclude the presence of other unstated features, elements, components, groups, integers and/or steps.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." Further, it is to be understood that "a," "an," and "the" include plural referents unless the content clearly dictates otherwise. The term "about" means plus or minus 0.1 to 50%, 5-50%, or 10-40%, preferably 10-20%, more preferably 10% or 15%, of the number to which reference is being made.

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

II. ASSAYS, METHODS AND PRODUCTS

PCT application PCT/CA2008/001561 filed Sep. 5, 2008, incorporated herein by reference in its entirety teaches, for example, a method of monitoring response to chemotherapy in patients with locally advanced breast cancer by monitoring the ability of the chemotherapy agents to induce degradation of RNA as measured, for example, by the RNA Integrity Value (RIN) (Schroeder, Mueller et al. 2006) as well as the ratio of 28S:18S ribosomal RNA. Using data from a national clinical trial (CAN-NCIC-CTG-MA.22; hereinafter "MA22"), it was demonstrated that tumour RIN values fell significantly in some breast cancer patients upon treatment with epirubicin/docetaxel chemotherapy and that low tumour RIN values mid-treatment could be significantly correlated with high drug dose levels for the regimen (p=0.05) (Parissenti, Chapman et al. 2010). They also were able to show a correlation between low mid-treatment tumour RIN values and a pathologic complete response within the breast and axilla post-treatment.

The MA22 RNA electropherogram data was examined to determine components of the electropherogram correlating with clinical response. It became evident that the Agilent Bioanalyzer software misidentified either the 28S peak or the 18S peak on electropherograms in >20% of the samples. For example, in at least some of these samples, a small portion of the tip of a peak was identified as the whole peak. However, The Agilent 2100 Bioanalyzer software (Agilent Expert) (Mueller 2004; Vespucci 2005) was able to correctly identify the 28S and 18S peaks on electropherograms of intact RNA which are identifiable by eye. However, in samples with disrupted RNA, electropherogram peaks were misidentified by Agilent RIN software although the correct peaks remained in appropriate locations visually on the electropherogram. The Agilent method which generates RIN values, hereafter referred to as the RIN algorithm, was based on RNA samples which were either intact or had undergone complete autolytic degradation and had few "partially degraded" samples (Schroeder, Mueller et al. 2006). Methods such as the Agilent method are generally for the purpose of assessing autolytic degradation.

Importantly, the current RIN algorithm's misidentification of the 28S and 18S peaks resulted in aberrant 28S:18S ratios (often having a "0" value) or RIN values that were designated N/A (see for example FIGS. 18A-18F).

It is disclosed herein that cytotoxic treatment such as chemotherapy and/or radiation therapy induced RNA disruption comprises different profile features from autolytically degraded RNA. For example, FIG. 1 shows an electropherogram trace of a tumour sample in saline soaked gauze for 24 hours where autolytic degradation takes place. A large peak of small fragments is visible at approximately the 26 second mark of the trace. There is also a loss of the 28S peak.

Figure 2:
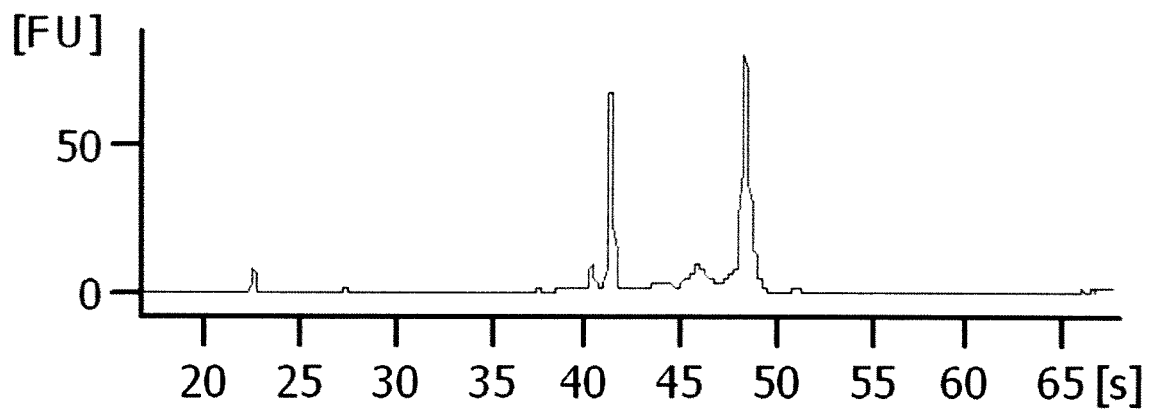
FIG. 2 is an illustration of an electropherogram trace of RNA isolated from human A2780 ovarian cancer cells that have been treated for 24 hours at 37° C. with the chemotherapeutic agent docetaxel (10 µM in medium diluted 1 in 2 with phosphate buffered saline (50% media)
Figure 3:
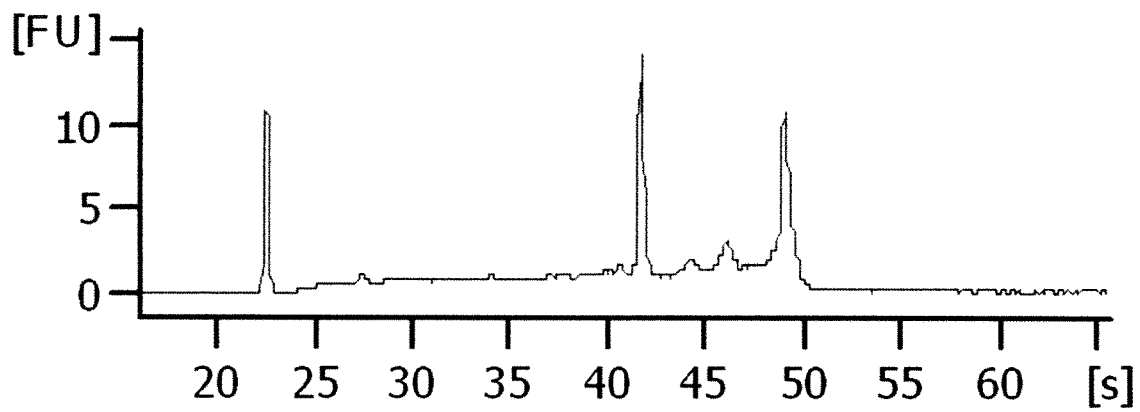
FIG. 3 is an illustration of an electropherogram trace of RNA isolated from A2780 cells treated for 24 hours at 37° C. with the chemotherapeutic epirubicin (20 µM in 50% media)
Figure 9A:
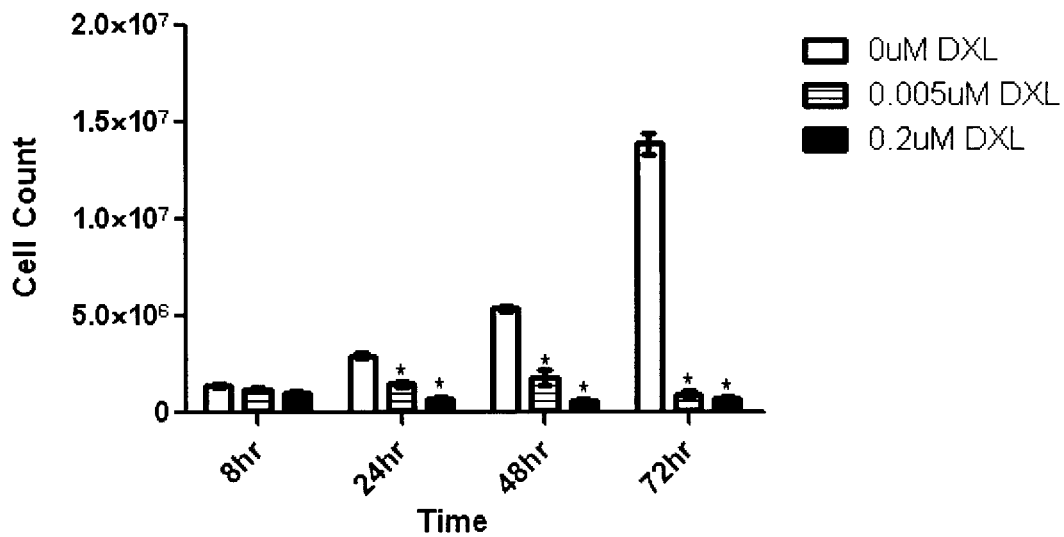
FIG. 9A is a graph demonstrating the number of A2780 ovarian cancer cells in culture after treatment with different concentrations of docetaxel for different time periods.
Figure 9B:
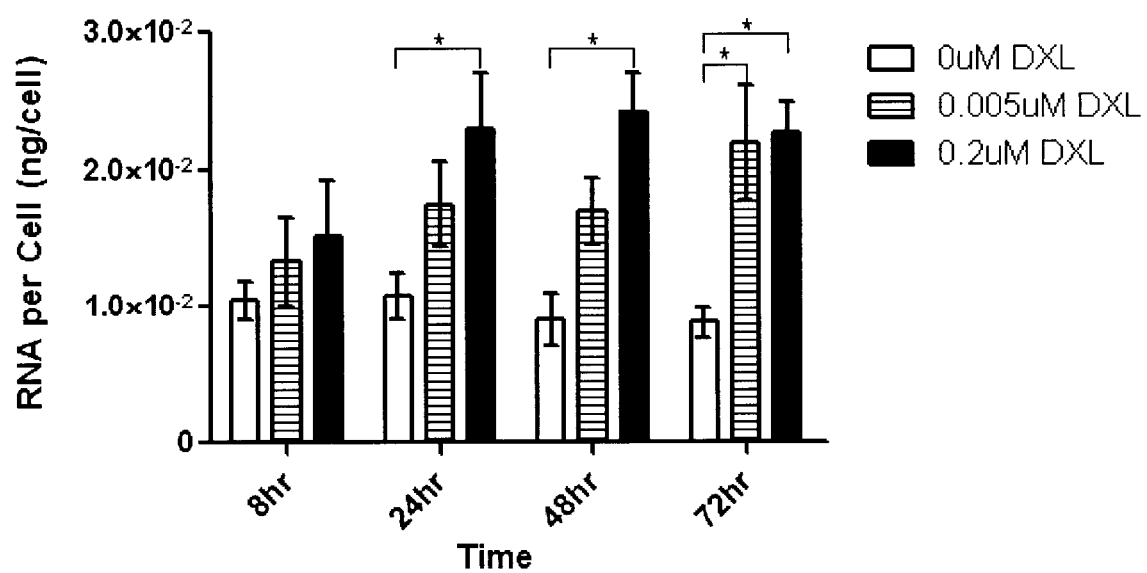
FIG. 9B is a graph of the amount of RNA per cell for A2780 ovarian cancer cells treated with different concentrations of docetaxel for different time periods.
Figure 9C:
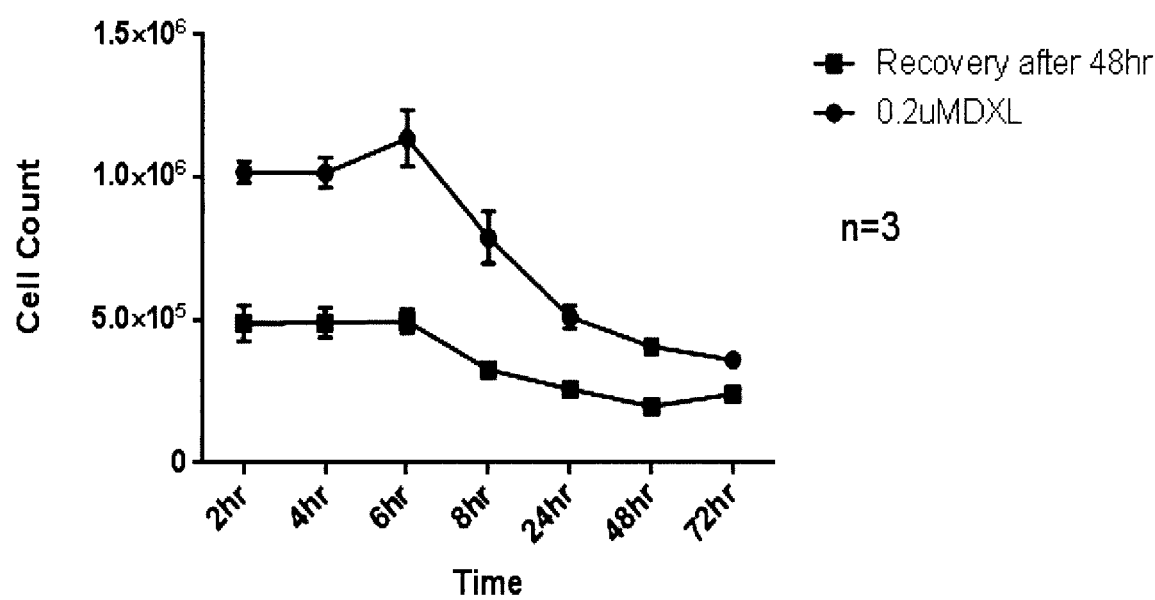
FIG. 9C is a graph plotting cell counts for cells treated with 0.2 micromolar docetaxel at different time points.
Figure 9D:
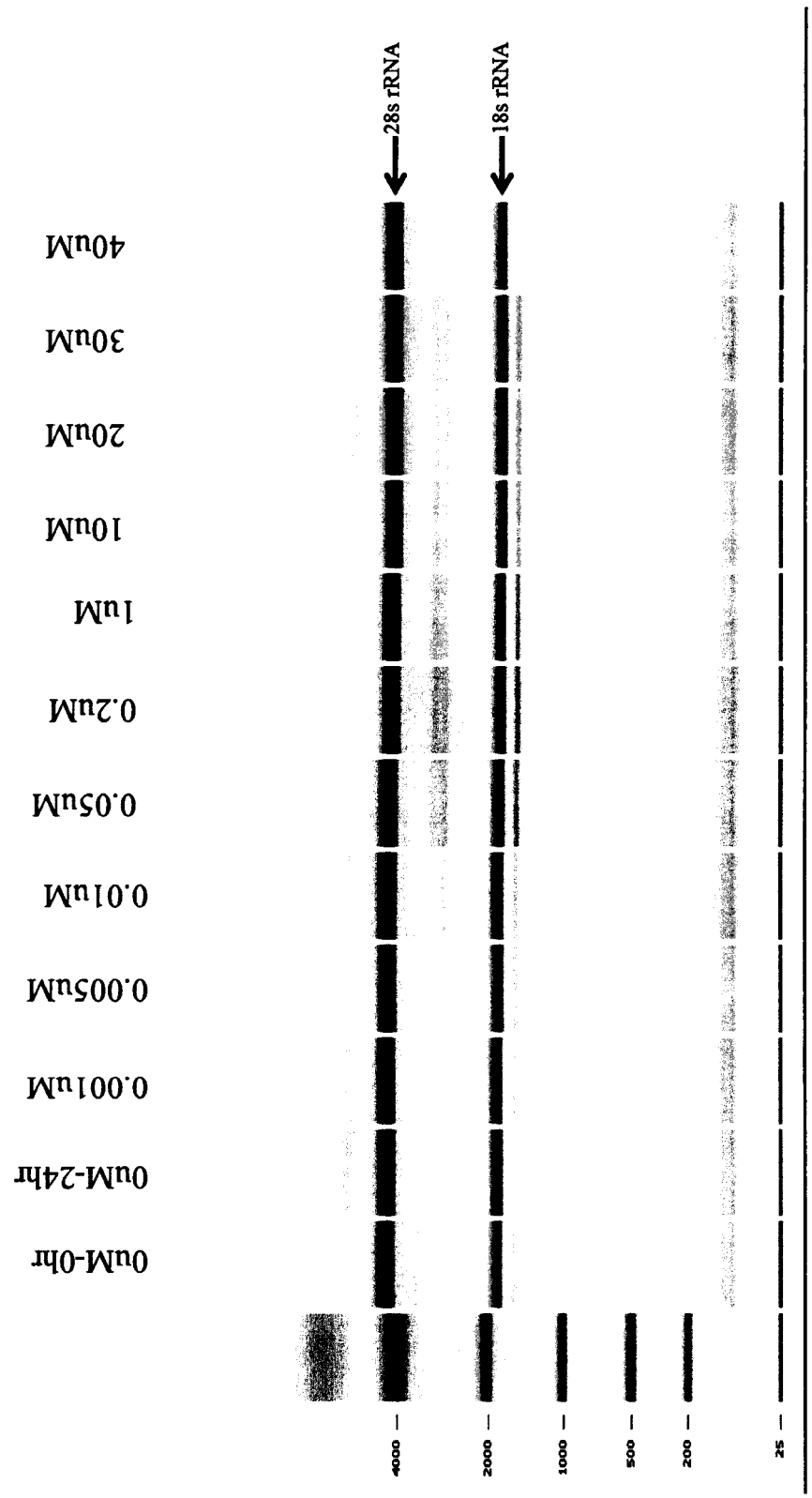
FIG. 9D is an image of a gel of electrophoretically separated A2780 ovarian cancer cell RNA samples treated with different concentrations of docetaxel for 24 hours.
Figure 9E:
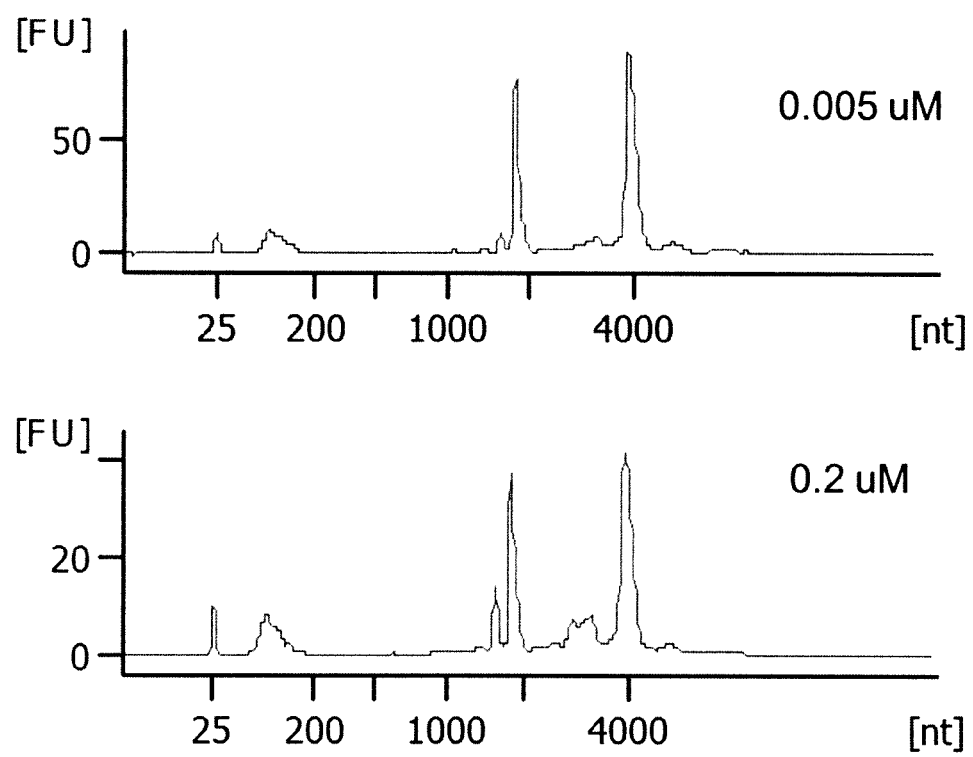
FIG. 9E is an illustration of an electropherogram trace corresponding to 0.005 micromolar and 0.2 micromolar lanes of FIG. 9D.

Cells treated with chemotherapeutic drugs show a different pattern of RNA disruption. For example, FIG. 2 shows human ovarian cancer cell line A2780 treated with chemotherapeutic docetaxel and shows an intermediate peak and a peak adjacent to the 18S peak. FIG. 3 shows A2780 cells treated with chemotherapeutic epirubicin. The electropherogram shows intermediate bands between the 18S and 28S peaks. FIG. 9D shows an image of a gel of RNA from A2780 cells treated with increasing concentrations of chemotherapeutic docetaxel. Additional bands are visible in cells treated with 0.05 uM docetaxel. FIG. 9E shown an electropherogram of the 0.005 and 0.2 uM time-points with the x axis being the size of the nucleotides. The electropherogram of the 0.2 uM time-point shows intermediate bands between the 18S and 28S peaks. In addition, the 28S and 18S peaks are shifted relative to those of FIG. 1 which shows autolytic RNA degradation.

It was also identified that the peaks misidentified using the RIN algorithm were found in RNA samples which had large "intermediate banding" peaks located between the 28S peak and 18S peak (see the examples in FIGS. 18A-F and FIG. 19).

A similar pattern is seen with radiation treatment. Additional bands are also visible in cells treated with radiation.

Accordingly, an aspect of the disclosure includes assays, methods and apparatuses for determining if a cancer patient is responsive to a chemotherapeutic drug. Generally, the method comprises determining features that are obtained from at least two of four different shifted regions of the electropherogram due to cytotoxic treatment: the shifted 28S peak, the shifted 18S peak, at least one peak in the "intermediate banding" region where the intermediate banding region is between the shifted 18S peak and the shifted 28S peak, and at least one peak in the "low banding" region where the low banding region is below the shifted 18S peak. For example, a scale of 0 to 100 units (the scale is described in more detail with regards to FIG. 5B) may be selected which includes all RNA migrating between 9.5 and 42.8 seconds under the condition of a Caliper Nano chip run on an Agilent 2100 Bioanalyzer.

Figure 4:
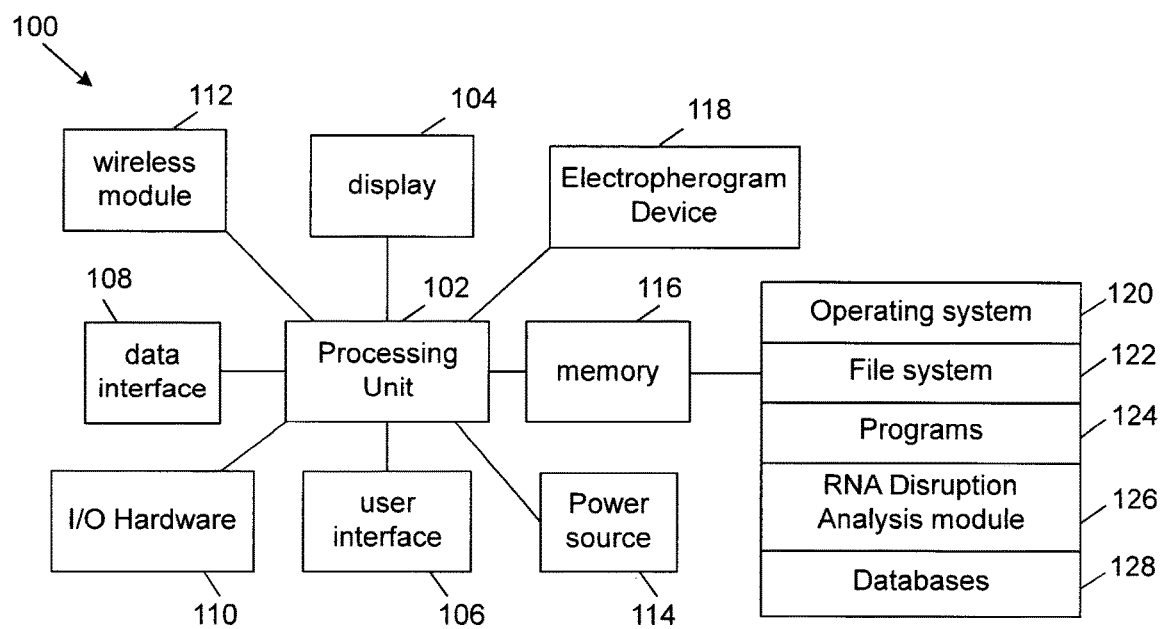
FIG. 4 is a block diagram of an example embodiment of an apparatus that can be used to assess RNA disruption.

Referring now to FIG. 4, shown therein is a block diagram of an example embodiment of an apparatus 100 that can be used to assess RNA disruption. The apparatus 100 is configured to perform a method to assess the electropherogram of RNA samples such as cancer RNA samples after the cancer samples have been subjected to a chemotherapeutic drug and/or radiation. The assessment results in a RNA Disruption Assay (RDA) score that incorporates various features based on the electropherogram data as described herein. A high RDA score is associated, for example, with positive treatment response such as subsequent pCR, while a low RDA score indicates that patients are unlikely to receive long term chemotherapy and/or radiation benefit. The methods described herein detect peaks and abnormal peaks in the electropherogram with increased resolution and increased robustness to help assess the effectiveness of chemotherapy and/or radiation treatment. Accordingly, the application of the method described herein depends on accurate recording of fluorescent intensities during the separation of RNA molecules but is independent of commercial software used to analyze peaks in the electropherogram data.

In general, the apparatus 100 comprises at least one processing unit 102, a display 104, a user interface 106, data interface 108, Input/Output (I/O) hardware 110, a wireless module 112, a power source 114, a memory 116, and an electropherogram device 118. The memory 116 comprises software code for implementing an operating system 120, a file system 122, various programs 124 including an RNA disruption analysis module 126 and at least one database 128. The apparatus 10 can be a standalone device or can incorporate a desktop computer, a laptop, a mobile device, a smart phone, a cell phone, a tablet, a personal digital assistant, and the like.

There can be various alternative embodiments for the apparatus 100 in which one or more of the components are not used. For example, in some embodiments the wireless module 112 is optional. Some embodiments may use either the wireless module 112 or the data interface 108. Furthermore, in some embodiments, the electropherogram device 118 is not included as the electropherogram data may be obtained and sent, for example, via a data communication network or wireless communication, or otherwise provided to the apparatus 100, for example, via a CD, a USB drive, a USB key and the like. In these cases, the electropherogram data is typically available in a data file that can be in a spreadsheet format or other numeric format that provides a time series of fluorescence intensity for one or more samples. In these cases, a medical professional, medical institution or a research institution can obtain the electropherogram data and provide this data for analysis by the apparatus 100. For example, there can be situations in which a second institution has the apparatus 100, receives the electropherogram data, analyzes the electropherogram data using the apparatus 100 and then sends the results to the entity which originally provided the electropherogram data.

The processing unit 102 controls the operation of the apparatus 100 and can be any suitable processor depending on the configuration of the apparatus 100 as is known by those skilled in the art. In some embodiments, the processing unit 102 can be implemented using an Application Specific Integrated Circuit (ASIC), a programmable logic array, or a collection of discrete analog and discrete circuits.

The display 104 can be any suitable display that provides visual information depending on the configuration of the apparatus 100. For instance, the display 104 can be a cathode ray tube, flat-screen monitor and the like if the apparatus 100 is a computer. In other cases, the display 104 can be a display suitable for a laptop, tablet or handheld device such as an LCD-based display and the like.

The user interface 106 can include at least one of a graphical user interface, a mouse, a keyboard, a touch screen, a thumbwheel, a track-pad, a track-ball, a card-reader, voice recognition software and the like again depending on the particular implementation of the apparatus 100. In some cases, some of these components can be integrated with one another.

The data interface 108 can be any interface that allows the apparatus 100 to communicate with other devices or computers. In some cases, the data interface 108 can include at least one of a serial port, a parallel port, or a USB port that provides USB connectivity. The data interface 108 can also include at least one of an Internet or local area network connection through Ethernet, Firewire or modem connections or through a digital subscriber line. Various combinations of these elements can be incorporated within the data interface 108.

The I/O hardware 110 can include at least one of a microphone, a CD-ROM drive, a CD-ROM read/write drive, a speaker and a printer. The wireless module 112 can be a radio that communicates utilizing CDMA, GSM, GPRS or Bluetooth protocol according to appropriate standards such as IEEE 802.11a, 802.11b, or 802.11g. The power source 114 can be any suitable power source that provides power to the apparatus 100 such as a power adaptor or a rechargeable battery pack depending on the implementation of the apparatus 100 as is known by those skilled in the art.

The memory 116 can include RAM and flash memory elements as well as other storage elements such as disk drives and hard drives. The memory 116 is used to store an operating system 120, a file system 122 and programs 124 as is commonly known by those skilled in the art. For instance, the operating system 120 and the file system 122 provide various basic operational processes for the apparatus 100. The programs 124 include various user programs so that a user can interact with the apparatus 100 including viewing, analyzing and reporting data as well as possibly sending and receiving messages depending on the implementation of the apparatus 100.

The memory 116 also stores an RNA Disruption analysis module 126 and one or more databases 128. The RNA Disruption analysis module 126 can determine RNA Disruption values for samples obtained from a patient that is receiving a form of chemotherapy and/or radiation according to various features and methods that are described in more detail with respect to FIGS. 5A, and 5B or 12A. In some embodiments, the RNA Disruption analysis module 126 can be implemented generally by the processing unit 102 which can be a processor that is programmed with firmware or that runs executable code, or is implemented by discrete circuit components, depending on the implementation of the apparatus 100.

In general, the processing unit 102 is configured to determine values for features from at least two shifted regions of the at least one electropherogram dataset and to determine an RDA score based on a combination of the values of the features. Accordingly, the processing unit 102, in its various alternative implementations, can acts as means for determining values for features from at least two shifted regions of the at least one electropherogram dataset and means for determining an RDA score based on a combination of the values of the features. The shifting is due to the treatment by the cytotoxic treatment e.g. chemotherapy and/or radiation.

The processing unit 102 is coupled to a data input to receive at least one electropherogram dataset corresponding to a unique biological sample comprising cellular RNA, such as cancerous tumour RNA, at various time points including at least one of during or after the treatment. In some cases, the electropherogram dataset can correspond to (i.e. is derived from) a unique biological sample that has not undergone treatment. In some embodiments, at least one of the electropherogram device 18, the data interface 108, the wireless module 112, the I/O hardware 110, the memory 116 and other suitable devices can acts as the data input or as means for obtaining at least one electropherogram dataset. The processing unit 102 is also coupled to a data output to convey an indication of the RDA score such as an RDI score, an RDA zone, or any other relevant analytical RNA data for at least one subject. In some embodiments, at least one of the display 104, wireless module 112, data interface 108, memory 116, and other suitable devices can act as the data output.

The databases 128 can be used to store data for samples that are assessed with the RNA Disruption analysis module 126. The databases 128 can also store other information required for the operation of the programs 124 or the operating system 120 such as dynamically linked libraries and the like.

The electropherogram device 118 is configured to produce an electropherogram of a sample. In general, the electropherogram device 118 employs a gel having a certain porosity in order to fractionate the RNA of the sample by size and charge of the particles. Fluorescence information related to the fractionated RNA is then obtained to produce an electropherogram trace for the sample. The electropherogram trace is then digitized to form an electropherogram dataset. The electropherogram device 118 can be implemented in a variety of ways. For example, in some embodiments, the electropherogram device 118 is an Agilent 2100 BioAnalyzer that employs Agilent RNA 6000 Nano kits and Caliper Technology's RNA Nanochips.

The apparatus 100 comprises at least one user interface and the processing unit 102 communicates with at least one of these user interfaces to receive electropherogram data as well as other information such as information on the individual from which the electropherogram was derived. This data can be received through the data interface 108, the I/O hardware 110, the wireless module 112, the memory 116 or the electropherogram device 118 depending on the particular implementation of the apparatus 100 and the type of data. The processing unit 102 can communicate with either one of these elements as well as the display 104 or the I/O hardware 110 in order to output the RDA score. For instance, the apparatus 100 can output the RDA score to a user of the apparatus 100. In addition, users of the apparatus 100 can communicate the resulting RDA score via a network connection to a remote system for storage and/or further analysis by other medical personnel. This communication can also include email communication in some embodiments.

In an alternative embodiment, the apparatus 100 can be a computer that acts as a web server and provides content for a web site. One of the webpages on the website can be a webpage that provides one or more RDA scores from samples as described herein. In this case, a user can interact with the webpage to provide the electropherogram data (e.g. by uploading the data) and the apparatus 100 can analyze the electropherogram data and display the RDA score on the web page and/or email the RDA score to the user and/or provide the RDA score for download by the user. Alternatively, the electropherogram data can be sent to the web server in an email communication, and the web server can analyze the electropherogram data to determine the RDA score and then send this information to a predefined destination, via email communication.

Figure 5A:
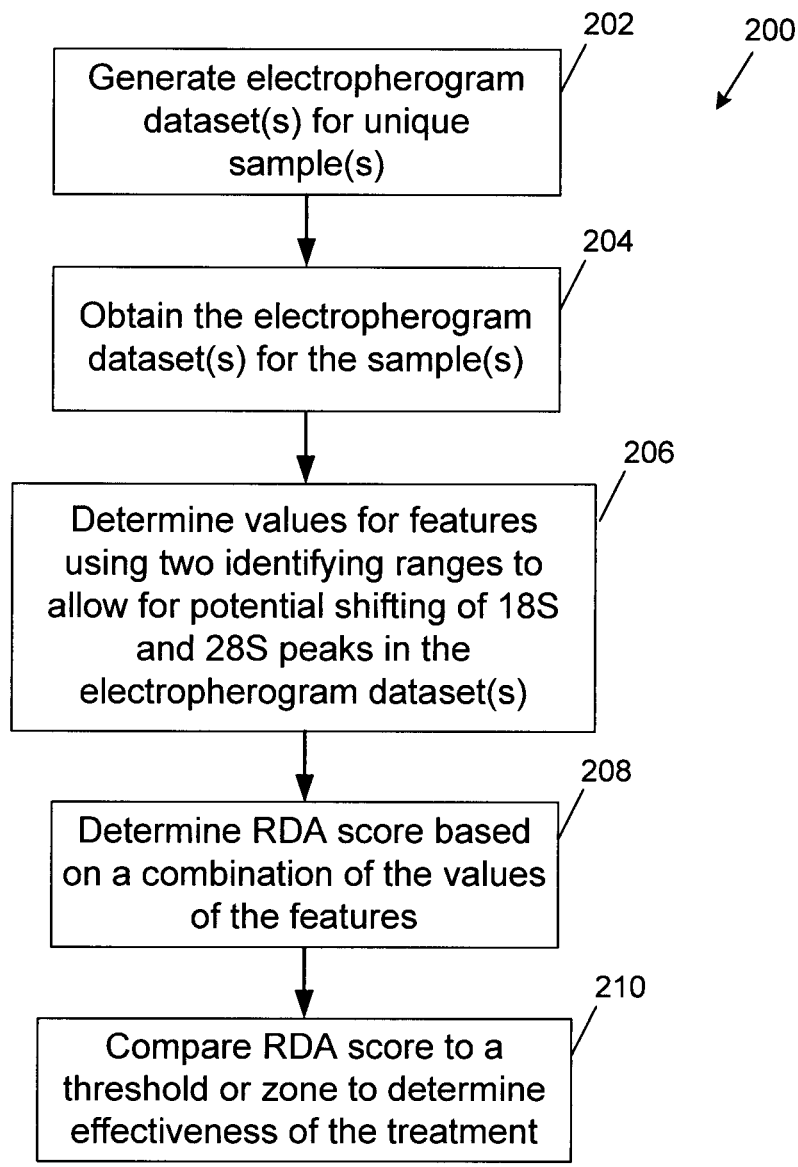
FIG. 5A is a flowchart of an example embodiment of a method that can be employed to assess RNA disruption.

Referring now to FIG. 5A, shown therein is a flowchart of an example embodiment of a method 200 that can be employed to assess RNA disruption. The method 200 is generally performed by the processing unit 102 in concert with additional elements of the apparatus 100, when required, in order to determine an RNA disruption assay score for electropherogram data that has been obtained from at least one sample at the same point in time.

Accordingly, an aspect of the present disclosure includes a method for performing an RNA Disruption Assay (RDA) for cellular RNA in response to a cytotoxic treatment, wherein the method comprises:

obtaining at least one electropherogram dataset corresponding to a unique biological sample comprising cellular RNA at a time point, during the course of treatment or after completion of the treatment;

determining values for features from at least two shifted regions of the at least one electropherogram dataset, the shifting being due to the treatment; and determining an RDA score based on a combination of the values of the features.

At 202, electropherogram data is generated for a sample. This may include generating several electropherogram datasets each from a unique biological sample that is taken from a patient or test subject (or if in vitro harvested) at a certain point in time, such as during or after cytotoxic treatment, for example, which may also be referred to as pre-therapy, mid-therapy and post-therapy respectively (also pre-treatment, mid-treatment and post-treatment) where therapy is defined as a series of chemotherapeutic and/or radiation administrations (e.g. injections, exposures) that are performed over a certain period of time such as minutes, days or weeks. In general, an electropherogram dataset is a digitized version of electropherogram traces that are generated for a sample. The electropherogram dataset is an array of numbers that are processed to generate an RDA score. In some embodiments, the electropherogram dataset can be in a spreadsheet format such as a Comma Value Separated (CVS) data file or an EXCEL data file format. In some embodiments, 202 of method 200 can be optional if the electropherogram data is produced by another entity and is then sent to another location for analysis at which case the method 200 starts at 204.

At 204, at least one electropherogram dataset(s) is obtained for a unique biological sample. The number of dataset(s) that are obtained depend on the features that are used to determine the RDA score. For example, some features can be used to determine the RDA score that require values from only one electropherogram dataset generated from one sample. However, some features can be used to determine the RDA score that require several electropherogram datasets generated from several unique biological samples, such as two or three datasets obtained from two or three unique biological samples, for example. In either case, the electropherogram dataset is typically obtained from a storage device such as a memory element 116, a CD-ROM, a USB key, a portable hard drive, from a database, from a network element, or from data that is uploaded over the Internet.

Figure 12A:
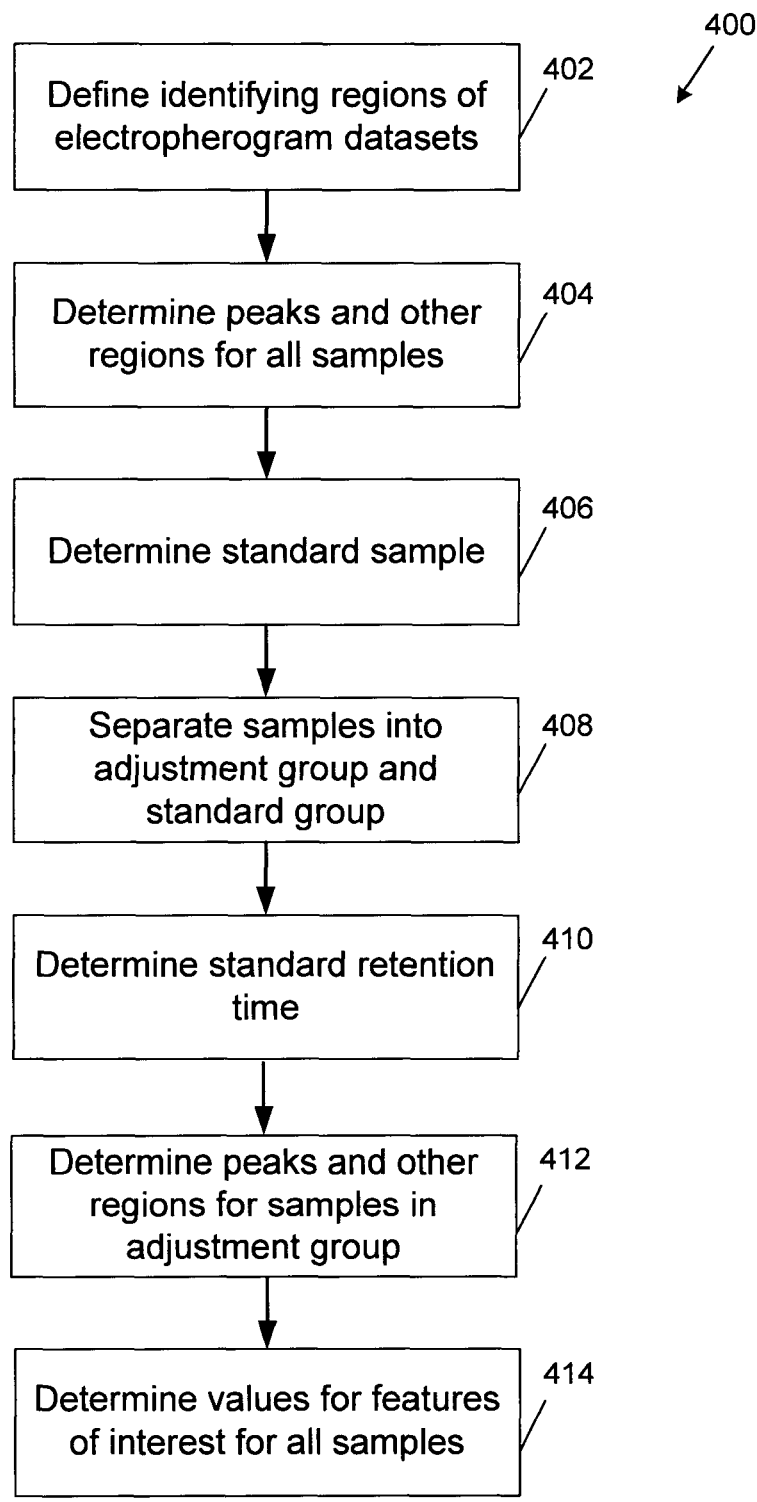
FIG. 12A is a flowchart of another example embodiment of a method that can be employed to determine features related to the 18S peak and the 28S peak in the 18S and 28S shifted regions respectively.

At 206, values are determined for features using two identifying ranges to allow for potential shifting of at least one of the 18S peak and 28S peak in the electropherogram dataset(s). For example, the identifying regions may be at least two shifted regions of the electropherogram dataset(s). The shifted regions that are analyzed in order to determine the values for the features include at least two of a shifted 18S region, a shifted 28S region, an intermediate banding region and a low banding region. The intermediate banding region is defined as the region between the 28S and 18S peaks. The low banding region includes all banding below the 18S peak but does not include the marker region. FIG. 5C is an example electropherogram in which these various peaks and regions are illustrated. The 28S and 18S peaks are defined to be within specific x axis (i.e. the time axis) ranges and can contain multiple maxima. However, an alternative method can be used for the identification of the 18S and 28S peaks and is described below in more detail with respect to FIG. 12A. In this case, the identifying ranges are two broad regions that are defined (e.g. having a certain size) in order to locate the 18S and 28S peaks regardless of whether these peaks are shifted or otherwise distributed in the electropherogram dataset(s). Regardless of whether the method of FIG. 5B or the method of FIG. 12A is used, various features can be defined based on these regions and/or peaks. For example, the features can include one or more of the area of an 18S peak, the area of a 28S peak, the area of an intermediate banding region, the area of a low banding region, the area of one or more band sub-regions, and the total area. The total area is the sum of the area of the 18S peak, the 28S peak, the intermediate banding region and the low banding region. Other features can include one or more of the width of the 18S peak and the width of the 28S peak. The area of these peaks and regions can be calculated in general using well-known mathematical techniques such as the trapezoidal rule for numerical integration (Atkinson, 1989). However, the starting points of these peaks and regions are different due to the chemotherapeutic effect on the samples. Accordingly, in some cases, additional rules have to be used, in order to correctly determine the values of these features.

Another example embodiment of an improved method for the identification of the 18S and 28S peaks and the calculation of certain features associated with these peaks or neighboring regions that can be used in act 206 of method 200 is described with respect to FIG. 12A. The low banding region can also be divided into the "low C", "low B" and "low A" sub-regions or banding regions as demonstrated in FIG. 12B for use in some methods described herein. It has been found that the low A banding region may contain RNA due to autolytic degradation as well as due to other effects and that the low C banding region is an important region in assessing the effect on RNA due to various external stimuli such as cytotoxic treatments, for example. It has also been found that in response to certain drugs, the RNA starts to spread to the low C banding region, then to the low B banding region and then to the low A banding region.

At 208, an RDA score is determined based on a combination of the values for various features. These combinations can include the ratios of some of these features. In some cases, only one electropherogram dataset from one sample is used to determine an RDA score. In other cases, several electropherogram datasets from several unique biological samples obtained at the same time are used to determine an RDA score. In these latter cases, the values can be combined using a mathematical function such as the minimum function or the maximum function.

Features can also be based on other components of the shifted regions of the electropherogram such as one or more of a peak height, a peak width and a peak position. For example, in one embodiment, it may be possible for the combination of features to be based on the 18S and 28S peak widths to discriminate between Responders and Non-Responders.

In one embodiment, the combination of features comprises a ratio of the 28S peak area in the shifted 28S region to the 18S peak area in the shifted 18S region, which can be represented by the expressions "28S/18S" or "28S:18S".

In one embodiment, the combination of features comprises a ratio of the 28S peak area in the shifted 28S region to the total area, which can be represented by the expression "28S/total area".

In one embodiment, the combination of features comprises a ratio of the 18S peak area in the shifted 18S region to the total area, which can be represented by the expression "18S/total area".

In one embodiment, the combination of features comprises a ratio of the intermediate banding region area to the total area, which can be represented by the expression "intermediate area/total area".

In one embodiment, the combination of features comprises a ratio of the low banding region area to total area, which can be represented by the expression "low banding area/total area".

In one embodiment, the combination of features comprises a ratio of the intermediate banding region area to the addition of the 18S peak area in the shifted 18S region and the 28S peak area in the shifted 28S region, which can be represented by the expression "intermediate banding area/(18S+28S)".

In one embodiment, the combination of features comprises a ratio of the low banding region area to the addition of the 18S peak area in the shifted 18S region and the 28S peak area in the shifted 28S region, which can be represented by the expression "low banding area/(18S+28S)".

In one embodiment, the combination of features comprises a ratio of the low C banding region area to the sum of the 18S peak area in the shifted 18S region and the 28S peak area in the shifted 28S region, which can be represented by the expression "low C/(18S+28S)". It should be noted that 18S and 28S can be reversed in any of these expression such as 28S+18S and it would not change the meaning of the expression.

In one embodiment, the combination of features comprises a ratio of the intermediate banding region area to the 18S peak area in the shifted 18S region, which can be represented by the expression "intermediate banding area/18S".

In one embodiment, the combination of features comprises a ratio of the low banding region area to the 18S peak area in the shifted 18S region, which can be represented by the expression "low banding area/18S".

In one embodiment, the combination of features comprises a ratio of the intermediate banding region area to the 28S peak area in the shifted 28S region, which can be represented by the expression "intermediate banding area/28S".

In one embodiment, the combination of features comprises a ratio of the low banding region area to the 28S peak area in the shifted 28S region, which can be represented by the expression "low banding area/28S".

In one embodiment, the combination of features comprises a ratio of the addition of low banding region area and intermediate banding region area to the addition of the 18S peak area in the shifted 18S region and the 28S peak area in the shifted 28S region, which can be represented by the expression "(low banding area+intermediate banding area)/(18S+28S)".

In one embodiment, the combination of features comprises a maximum ratio determined from at least two electropherogram datasets. The ratio is defined as the intermediate banding region area divided by a sum of the 18S peak area in the shifted 18S region and the 28S peak area in the shifted 28S region. This can be represented by the expression "maximum intermediate banding area/(18S+28S)". In this case, as with other calculations that use the maximum function with particular features that follow below, the ratios of intermediate banding area/(18S+28S) are calculated for two or more electropherogram datasets (derived from two or more unique biological samples at the same time point), the maximum of these ratios is calculated and then the logarithm is calculated. For example, two or more electropherogram datasets can be derived from two or more biopsies taken at a time point and/or a biopsy that is divided into two or more samples.

In one embodiment, the combination of features comprises a minimum ratio determined from at least two electropherogram datasets. The ratio is defined as the intermediate banding region area divided by a sum of the 18S peak area in the shifted 18S region and the 28S peak area in the shifted 28S region. This can be represented by the expression "minimum intermediate banding area/(18S+28S)". In this case, as with other calculations that use the minimum function with particular features that follow below, the ratios of intermediate banding area/(18S+28S) are calculated for two or more electropherogram datasets (derived from two or more unique biological samples at the same time point) and the minimum of these ratios are is calculated.

In one embodiment, the combination of features comprises a maximum ratio determined from at least two electropherogram datasets. The ratio is defined as the intermediate banding region area divided by the total area. This can be represented by the expression "maximum intermediate banding area/total area".

In one embodiment, the combination of features comprises a minimum ratio determined from at least two electropherogram datasets. The ratio is defined as the low banding region area divided by the total area. This can be represented by the expression "minimum low banding area/total area".

In one embodiment, the combination of features comprises a ratio of low banding region area divided by the total area and a maximum of a second ratio determined from at least two electropherogram datasets, the second ratio being the intermediate banding area divided by the total area. These combinations of features can be represented by the expressions "low banding area/total area" and "maximum intermediate banding area/total area", respectively.

In one embodiment, the combination of features comprises a maximum ratio determined from at least two electropherogram datasets. The ratio is defined as the 28S peak area divided by the total area. This can be represented by the expression "maximum 28S/total area".

In one embodiment, the combination of features comprises a minimum ratio determined from at least two electropherogram datasets. The ratio is defined as the 28S peak area divided by the total area. This can be represented by the expression "minimum 28S/total area".

In one embodiment, the combination of features comprises a maximum ratio determined from at least two electropherogram datasets. The ratio is defined as the 18S peak area divided by the total area. This can be represented by the expression "maximum 18S/total area".

In one embodiment, the combination of features comprises a minimum ratio determined from at least two electropherogram datasets. The ratio is defined as the 18S peak area divided by the total area. This can be represented by the expression "minimum 18S/total area".

In one embodiment, the combination of features comprises a maximum ratio determined from at least two electropherogram datasets. The ratio is defined as the intermediate area divided by the 28S peak area in the shifted 28S region. This can be represented by the expression "maximum intermediate/28S".

In one embodiment, the combination of features comprises a minimum ratio determined from at least two electropherogram datasets. The ratio is defined as the intermediate area divided by the 28S peak area in the shifted 28S region. This can be represented by the expression "minimum intermediate/28S area".

It should be noted that in each of these feature combinations described above, either method 300 or method 400 (described in FIG. 12A) can be used to define the 18S and 28S peaks and the other regions. If method 400 is used than rather than using shifted regions, broader regions are used to locate the 18S and 28S peaks.

At 210, the RDA score can be compared to a threshold to determine the effectiveness of the treatment. The threshold can be a scalar value determined based on conducting ROC analysis on a database of various experimental results to identify responders which can be done by selecting a threshold value to accomplish a high Positive Predictive Value (PPV) and a low false positive rate. The analysis can also be conducted to identify non-responders by selecting a threshold value so that the non-responders can be identified with a high Negative Predictive Value (NPV) and a low false negative rate. Accordingly, the goal is to have a threshold for high PPV and a threshold with high NPV and to minimize the distance between the PPV and NPV threshold values. In some embodiments, several thresholds can be used to define several RDA zones which relate to different types of expected treatment results such as increased likelihood of a complete response, a partial response and no response (see FIG. 7A and/or FIG. 14A for examples of the RDA zones).

In an alternative embodiment, rather than comparing the RDA score to a threshold value, the RDA score may be compared to a threshold curve which may be linear or non-linear or a threshold three dimensional region. In this case, the threshold line, threshold curve or threshold plane can be determined using LDA or QDA as is described with respect to FIGS. 15B-15D.

Figure 5B:
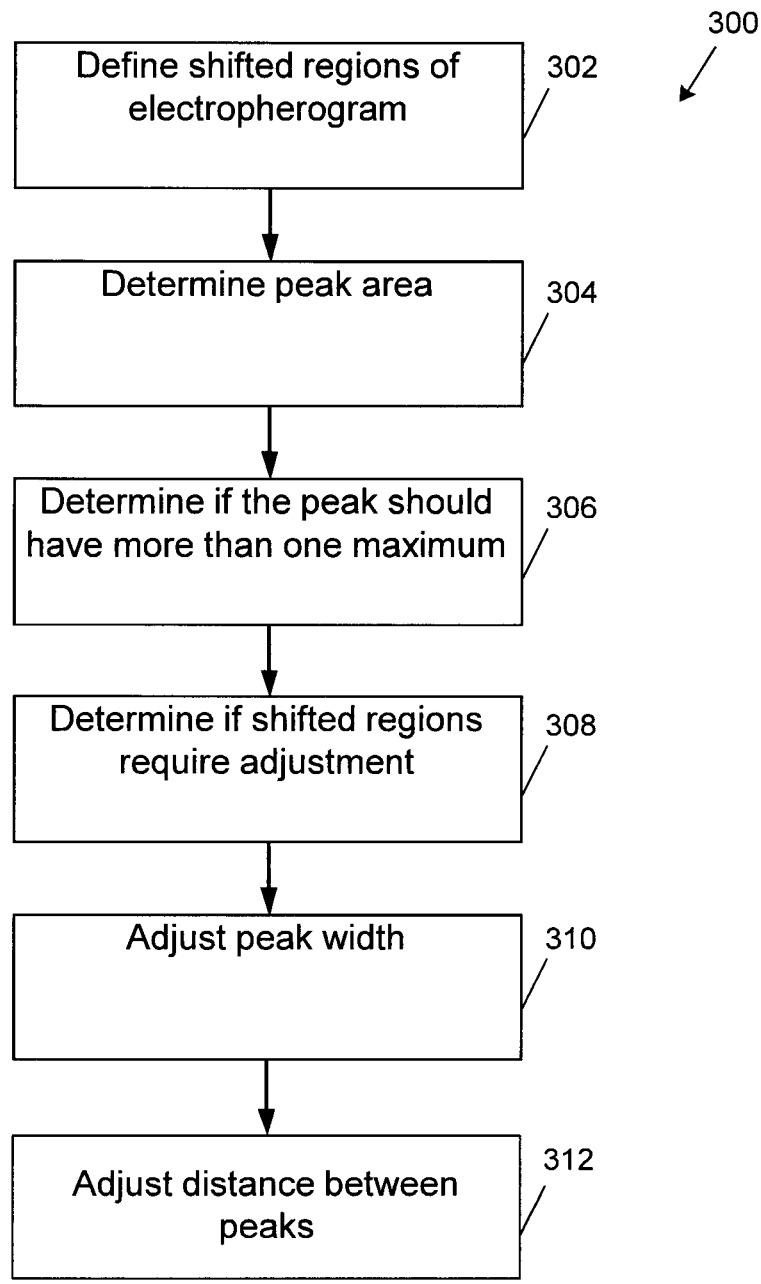
FIG. 5B is a flowchart of an example embodiment of a method that can be employed to determine features related to 18S and 28S peaks in the 18S and 28S shifted regions respectively.
Figure 5C:
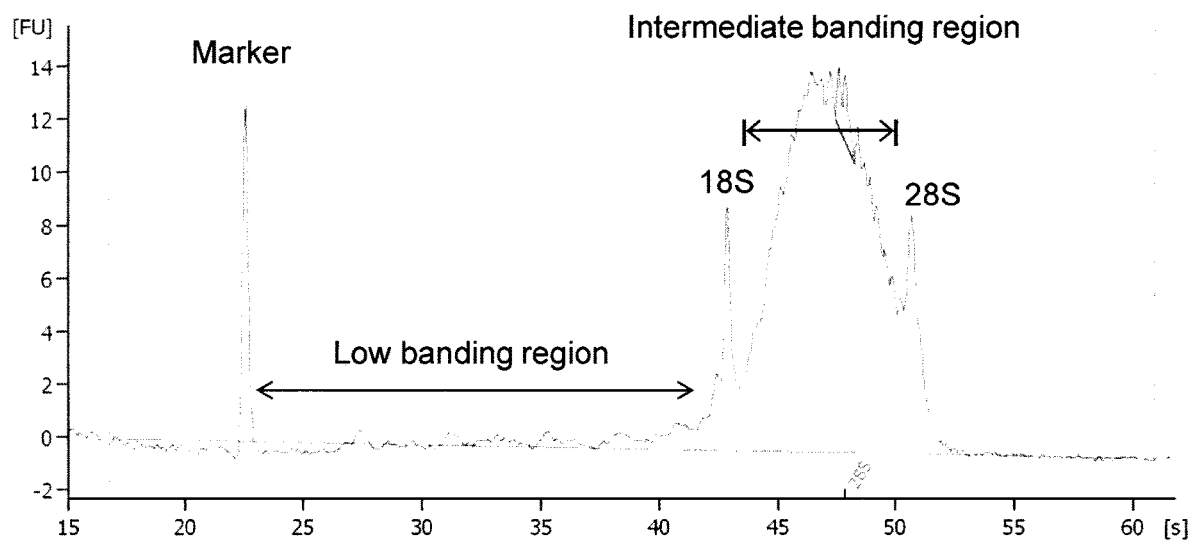
FIG. 5C is a graph of an example electropherogram that defines the 18S peak, 28S peak, intermediate banding region, low banding region and the marker region.

Referring now to FIG. 5B, shown therein is a flowchart of an example embodiment of a method 300 that can be employed to determine features related to 18S and 28S peaks in the 18S and 28S shifted regions respectively (another method is described with respect to FIG. 12A). While these peaks are distinguishable from other peaks and have certain sizes, one or more rules can be used to increase the accuracy of the determination of these peaks and their resulting areas. However, not all of the following rules need to be applied. For example, when there are strong 18S and 28S peaks and little or no intermediate banding, then steps 310 and 312 may not have to be performed.

At 302, boundaries for the shifted regions of the electropherogram are defined due to the effects of chemotherapy, or some other treatment regimen or effect, on the sample in order to properly determine the 18S and 28S peaks. After iterating through a number of experimental results, about 95% of the 18S peaks were found in the range of 39.5 to 43.5 seconds (i.e. shifted 18S region) and those of the 28S peaks were in the range of 47.5 to 53.5 seconds (i.e. shifted 28S region); this analysis can be repeated for other treatment regiments. Accordingly, the boundary conditions for the shifted 18S and 28S regions were changed from the range of 38.5 to 46.5 seconds and the range of 43 to 53.5 seconds to the range of 39.5 to 43.5 seconds and the range of 47.5 to 53.5 seconds respectively. It should be noted that these ranges can change depending on different processing techniques such as that described with respect to FIG. 12A, for example. If the time axis (e.g. x axis) of the electropherogram datasets is converted to a scale of 0 to 100 units, then the boundary conditions for the shifted 18S region become 40.9 to 50.4 and the boundary conditions for the shifted 28S region become 58.1 to 69.5. The conversion includes mapping the end of the marker region as the 0 unit and a time point in the area of about 60 to 65 seconds, such as 63 seconds, for example, as the 100 unit. This resulted in 18S and 28S peaks being defined by more stringent conditions.

Most peaks were identified correctly using these shifted 18S and 28S regions. This may involve searching for all of the peak candidates first, and then choosing the one with largest area as the 18S peak or the 28S peak. Candidate peaks whose width is not within about 0.6 to 7.6 units for the 18S peak and not within about 0.8 to 10.5 units for the 28S peak, respectively, may be excluded from the candidate peak set, so that they will not be chosen as the 18S peak or the 28S peak. It has been found that the probability of misidentifying the 28S peak is much larger than that of misidentifying the 18S peak. Accordingly, one may determine the 18S peak first. Also, when identifying the 28S peaks, those 28S peak candidates whose distance to the 18S peak is greater than a distance threshold will be excluded from the peak candidates set so that they will not be chosen as the 28S peak.

At 304, the peak area is determined for a peak, such as the 18S and the 28S peaks, for example. To make this determination, the idea of a local minimum (Stewart, 2008) can be used to define the peak area. The local minimum of a function is the smallest value that the function takes at a point within a given neighborhood. Once the peak of 18S or 28S is known, the two local minimums closest to the peak can be found. The point corresponding to the local minimum on the left side of the peak (within the shifted region) can be defined as the starting position of the peak, and the point corresponding to the local minimum on the right side of the peak (within the shifted region) can be defined as the ending position of the peak. The peak area is defined as the area between these two local minimums. Accordingly, a peak area for a given peak is defined by an area between two local minimum values on either side of the peak in the given shifted region where the peak has one maximum value.

However, the peak can also be defined to have more than one maximum value in certain cases as is described below. At 306, it is determined if the peak should have more than one maximum value (i.e. more than one peak) depending on the area of the peak. This adjustment is used since many of the errors which were found with the RIN method were due to multiple maxima within the 28S and 18S peaks (see FIG. 18). The existence of multiple peaks or multiple values in a peak can be determined in several ways. By analyzing experimental data, if it was found that the value of a peak area was smaller than a threshold value, then the peak was allowed to comprise more than one maximum value. In other words, if the calculated area doesn't match the corresponding peak, i.e. the peak area is very small when the peak is actually large, then the peak is defined to be multi-peaked. For example, the peak could have two maximum values. In one example embodiment, the threshold is 0.2 FU·seconds. This condition successfully corrected for most of the previously improperly detected examples of the RIN method.

At 308, boundaries of the shifted 18S and 28S regions are adjusted if needed depending on the areas of these peaks with respect to each other. For example, if an 18S peak area in the shifted 18S region divided by total area multiplied by 100 (which is represented by 18S %) is less than about 8 times the 28S peak area in the shifted 28S region divided by total area multiplied by 100 (which is represented by 28S %), the shifted 18S region is defined to be the range of 42.8 to 51.4 units (where the time axis is converted to a scale of 0 to 100), i.e. the bounds of the shifted 18S region were extended from 42.8 to 50.4 units to about 42.8 to 51.4 units.

In a similar fashion, if the 28S peak area in the shifted 28S region divided by total area multiplied by 100 (i.e. 28S %) is less than about 8 times an 18S peak area in the shifted 18S region divided by total area multiplied by 100 (i.e. 18S %), the shifted 28S region is defined to be the range of about 52.3 to 69.5 units (where the time axis is converted to a scale of 0 to 100), i.e. the bounds of the shifted 28S region were extended from about 58.1 to 69.5 units to about 52.3 to 69.5 units.

At 310, the peak widths are adjusted if needed, i.e. if the widths are defined to be too large based on the position of the starting and ending position of a peak and a study of experimental results. Accordingly, after the peak widths of 18S and 28S were calculated they were subsequently adjusted if the width was outside a width range such that the width of the 18S peak should be within 0.6 to 7.6 units and the width of the 28S should be within 0.8 to 10.5 units when the time axis is converted to a scale of 0 to 100.

At 312, the distance between the peaks is adjusted if they are calculated such that they are too far apart to enhance the definition of the 18S and 28S peaks. Accordingly, a location of at least one of the 18S and 28S peaks is adjusted by picking a different candidate peak if the distance between the 18S and 28S peaks is greater than a distance threshold. For example, in some embodiments, the distance between an ending position of an 18S peak and a starting position of a 28S peak is defined to be less than about 17.1 units apart.

Accordingly, another aspect of the disclosure is a method for performing an RNA Disruption Assay (RDA) for cellular RNA, wherein the method comprises: obtaining at least one electropherogram dataset corresponding to a unique biological sample comprising the cellular RNA at a time point; defining an 18S peak and a 28S peak from the at least one electropherogram dataset; determining at least one parameter value for both the 18S peak and the 28S peak; and redefining at least one of the 18S peak and the 28S peak when required according to one or more rules applied to the at least one parameter value. In at least some cases, the method can further include determining an 18S peak area and a 28S peak area; and determining an RDA score based on at least one of the 18S peak area and the 28S peak area.

In some embodiments, the at least one parameter value comprises at least one of a peak area, a peak width and a peak location.

The one or more rules comprises at least one of determining if at least one of the 18S peak and the 28S peak have more than one maximum value based on peak area, determining if boundaries where the 18S peak and the 28S peak are located require adjustment depending on comparing the areas of the 28S peak and 18S peak to one another, adjusting widths of the 18S peak and the 28S peak to be in a certain width range, and adjusting a location of at least one of the 18S peak and the 28S peak if a distance between the 18S peak and 28S peak is greater than a distance threshold. In some cases, the two rules of adjusting widths of the 18S peak and the 28S peak to be in a certain width range, and adjusting a location of at least one of the 18S peak and the 28S peak if a distance between the 18S peak and 28S peak is greater than a distance threshold are optional.

Once the 18S and 28S peaks are defined according to the method 200, other values can be determined such as the intermediate area, low banding area, etc.

It should be noted that in each of these feature combinations described below, either method 300 or method 400 (described in FIG. 12A) can be used to define the 18S and 28S peaks and the other regions. If method 400 is used than rather than using shifted regions, broader regions are used to locate the 18S and 28S peaks.

In one embodiment, the combination of features comprises a ratio of the intermediate area to the sum of the 28S peak area in the shifted 28S region and the 18S peak area in the shifted 18S region, which can be represented by the expression "Intermediate/(28S+18S)".

In one embodiment, the combination of features comprises a ratio of the sum of the low C banding region area and intermediate area to the sum of the 28S peak area in the shifted 28S region and the 18S peak area in the shifted 18S region, which can be represented by the expression "Intermediate+low C/(28S+18S)".

In one embodiment, the combination of features comprises a ratio of the sum of the low C banding region area and the intermediate area to the sum of the 28S peak area in the shifted 28S region and the 18S peak area in the shifted 18S peak region, which can be represented by the expression "(low C+Intermediate)/(28S+18S)".

In one embodiment, the combination of features comprises a maximum ratio determined from at least two electropherogram datasets. The ratio is defined as the intermediate area divided by the sum of the 18S and 28S peak areas in the shifted 18S and 28S regions respectively. This can be represented by the expression "maximum intermediate/(28S+18S)".

In some embodiments, the apparatus 100 and the computer readable medium can be configured to implement methods 200 and 300 or methods 200 and 400 or methods 200, 300 and 400 where method 400 is described with respect to FIG. 12A.

The step of obtaining the at least one electropherogram dataset comprises in an embodiment: separating the cellular RNA by electrophoresis; detecting one or more species of the separated cellular RNA; plotting the electropherogram and obtaining the at least one electropherogram dataset from the electropherogram plot.

Electrophoresis for separating RNA is a commonly used technique. For example, gels containing fluorescent dyes can be employed to detect separated RNA species. Automated microfluidics based electrophoresis methods and systems such as the Experion automated electrophoresis system (Bio Rad Laboratories, Inc.) and the Agilent 2100 Bioanalyzer (Agilent Technologic, Inc.) have been developed which can be used to separate RNA species. These systems use very small amounts of RNA and conduct microcapillary electrophoresis in channels of microchips.

Accordingly, the gel electrophoresis is microcapillary electrophoresis. In another embodiment, the microcapillary electrophoresis comprises using an RNA chip for electrophoretically separating the RNA.

Detection of the separated cellular RNA is performed, for example, using RNA dyes such as fluorescent dyes which bind the RNA. The RNA dyes can be added to the electrophoresis gel permitting detection of the RNA by detecting the dye signal.

Cellular RNA for use in the assay can be, for example, isolated from a biological sample (including any biological sample comprising cancer cells including for example a sample comprising cells of a cell line, human tissue or animal tissue) using techniques known in the art. For example, cells and/or a biopsy can be re-suspended/lysed in a RNA isolating or stabilizing solution such as RNAzol™ (Sigmal/Aldrich Co.), RNAlater™ (Qiagen Laboratories), RNA Stable™ (Biomatrica Co.), RNA Protect Cell Reagent™ (Qiagen Laboratories) and RNA isolated using one or more commercially available kits (according to manufacturer's directions), including, but not limited to, RNeasy™ (Qiagen Laboratories), miRNeasy™. (Qiagen Laboratories), RNAzol™ (Sigma/Aldrich Co.), Total RNA Isolation Kit (Norgen Biotek Co. and Agilent Technologies, Inc.), Purelink™ (Invitrogen Labs), 5 PRIME PerfectPure™, andGeneJET (Thermo Scientific) kits.

As mentioned, changes in RNA disruption can be used to monitor response to cytotoxic treatment. For example, FIGS. 6A-6K, 13, 14A-D, 15A-15D and others demonstrate that RDA can be used to discriminate subjects receiving chemotherapy with an increased likelihood of pCR from non-responders (i.e. non-pCR responders) as well identify patients in an intermediate RDA zone. Changes in RNA disruption are also seen with radiation (e.g. see FIGS. 10, 11A and 11B). Without wishing to be bound to theory, RNA disruption in a tumour cell may take place before cell death and/or before changes in cellularity, particularly during early stages of treatment. Accordingly, the RDA is suitable for assessing subject response to a cytotoxic treatment, such as a chemotherapy treatment.

Another aspect of the disclosure includes an assay comprising:

quantifying the amount of RNA disruption in a biological sample comprising cellular tumour RNA at a time point during or after cytotoxic treatment such as, but not limited to, chemotherapeutic treatment, radiation treatment, and cytotoxic adjuvant treatment, for example, using an RNA disruption assay (RDA) as described herein to determine an RDA score; and determining if the amount of RNA disruption of the cellular RNA is increased or not increased.

As mentioned this can involve determining whether a subject falls within an RDA zone. For example, FIGS. 7A and 14A, which are log-log plots, show that responders and non-responders can be separated by RDA zones.

In an embodiment, the RDA zone information may be transmitted to the subject, optionally through a medical professional.

The tumour cell RNA can be from, for example, a tumour cell line, or can be from a tumour cell sample from a subject such as a biopsy.

In one embodiment, the tumour cell RNA assessed is from an untreated sample (e.g. untreated tumour cells in vitro) or is from a subject at a time point before treatment (e.g. pre-therapy).

Reports of tumour samples showing aberrant 28S/18S ratios have been reported.

For example, abnormal 28S:18S ratios have been reported in untreated tumour tissue (Skrypina, et al. 2003). It has been suggested that this loss in 28S is due to preferential cleavage within GC-rich regions (Johnson, Sendler, Lalancette, Hauser, Diamond, & Krawetz, 2011).

In one embodiment, the cellular RNA is isolated from a normal cell. For example, the present method and assays can be used to assay normal cell response to cytotoxic drugs such as, but not limited to, chemotherapeutics, for example, to assess drug toxicity on non-cancer cells.

In one embodiment, the determining step comprises comparing the quantified amount of RNA disruption in the biological sample with a control such as a threshold or reference value. In an embodiment, the reference value corresponds to a pretreatment value.

In an embodiment, the increase is relative to a control or an expected pretreatment score.

A pretreatment sample comprising for example cancerous tumour cell RNA can comprise relatively little or no RNA disruption. For example, the RNA integrity will be stable.

For example, untreated breast cancer tumour biopsies assessed for RNA disruption using the methods described herein are typically identified as falling within zone 1. RNA degradation can be scored in some embodiments without relation to a comparator (e.g. using an absolute scale). In some embodiments, threshold values can be used. Thresholds values for example, which define a zone can be used to classify the subject. Accordingly a determination of an RDA score that falls for example within zone 2 or 3 is indicative that the sample contained disrupted RNA even in the absence of a comparator sample on the basis of the expected untreated amount of RNA disruption. Accordingly, the determining step can comprise comparing to a priori determined value or an expected value for the tumour type.

In another embodiment, the RNA disruption assay (RDA) is for measuring cancer treatment, e.g. chemotherapy and/or radiation, induced RNA disruption. Assays employing the RDA can be used to identify which subjects and/or tumours respond to a chemotherapy and/or radiation treatment.

Accordingly in another embodiment, the assay further comprises identifying the tumour as responsive to a cancer treatment, optionally a chemotherapeutic and/or radiation treatment, if the amount of RNA disruption (e.g. the RDA score) is increased relative to the reference or threshold value.

In another embodiment, the biological sample corresponds to cells, such as cancerous tumour cells, treated in vitro or in vivo.

Figure 9F:
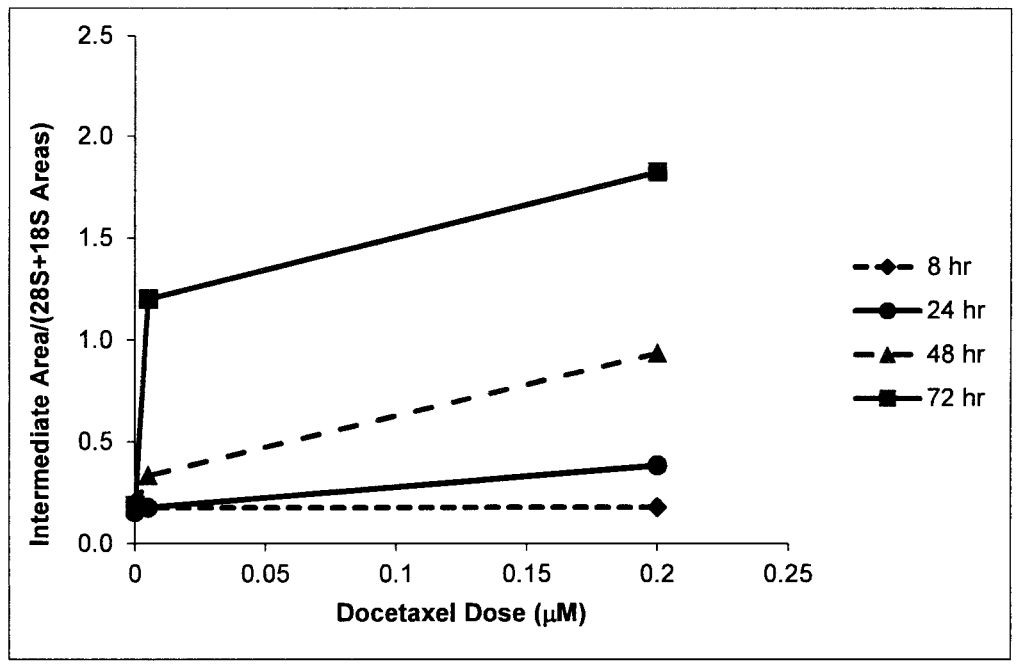
FIG. 9F is a graph of the intermediate area/(28S+18S) calculated from the trace of FIG. 9E.
Figure 9G:
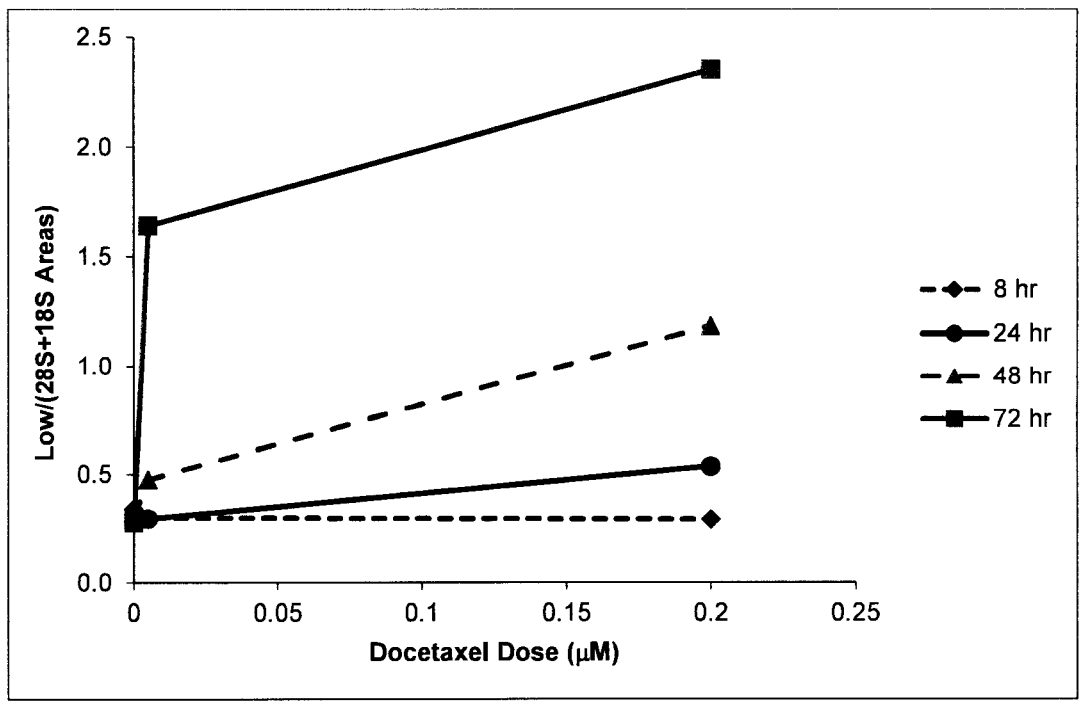
FIG. 9G is a graph of the Low Area/(28S+18S) calculated from the trace of FIG. 9E.
Figure 9H:
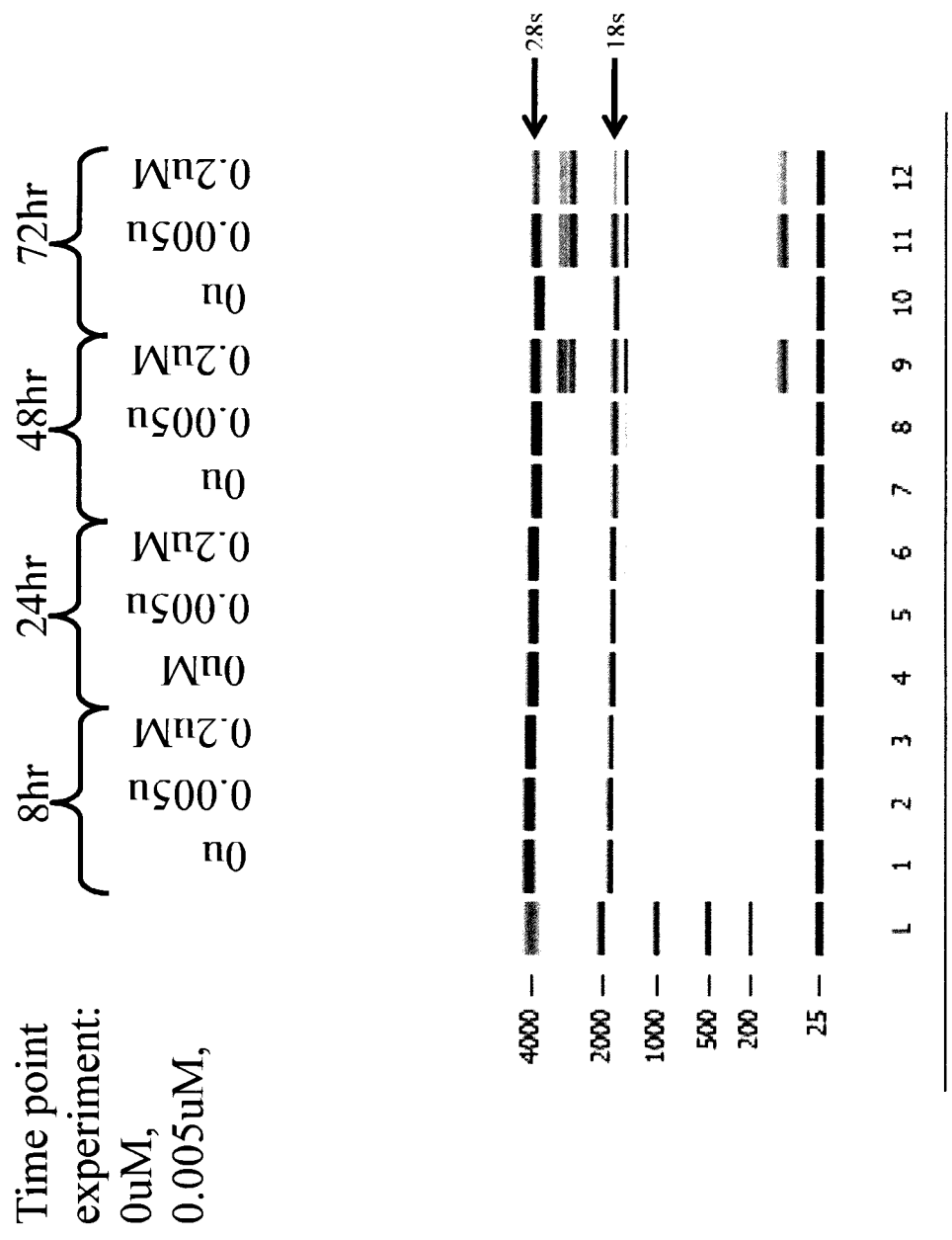
FIG. 9H is an image of a gel of electrophoretically separated A2780 ovarian cancer cell RNA samples of cells treated with different concentrations of docetaxel for different time periods.
Figure 9I:
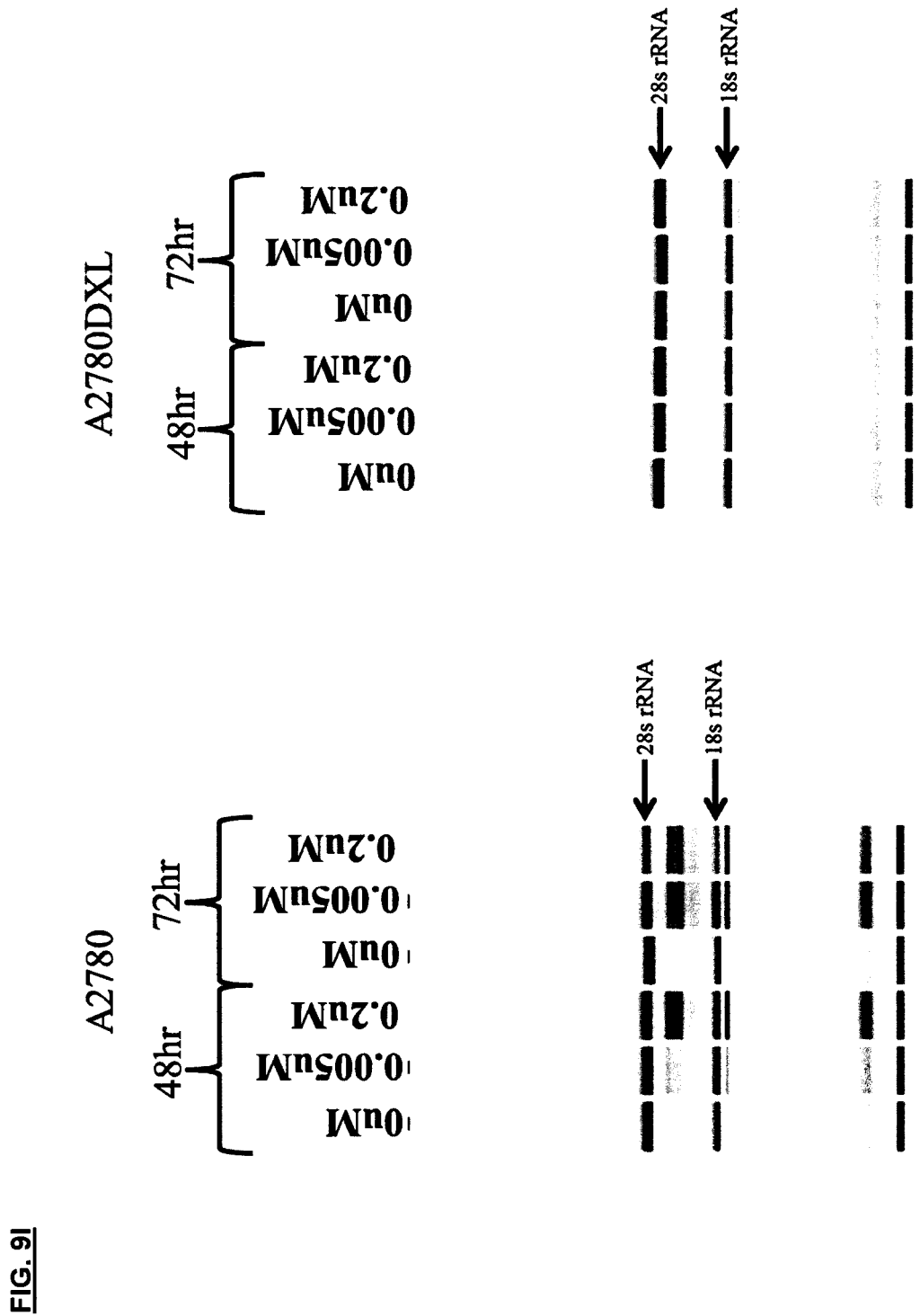
FIG. 9I is a series of images of gels of electrophoretically separated A2780 sensitive and resistant cell RNA samples.

FIG. 9I shows that sensitive A2780 cells show RNA disruption whereas resistant A2780 cells do not.

Also provided in one embodiment described herein, is an in vitro assay for determining sensitivity of a cancerous tumour cell or a normal cell to a cancer treatment such as a chemotherapeutic and/or radiation treatment, the assay comprising:

treating a cell or cell population with a chemotherapeutic and/or with radiation;

quantifying the amount of RNA disruption in a biological sample comprising cellular RNA at a time point during or after treating the cell or cell population with the chemotherapeutic and/or radiation using an RNA Disruption Assay (RDA) as described herein optionally to determine an RDA score; and comparing the quantified amount of RNA disruption with a threshold or reference value, and if the amount of RNA disruption is increased relative to the reference value, identifying the cell as sensitive to the chemotherapeutic and/or radiation treatment and if not increased (e.g. if not increased significantly) identifying the cell as resistant to the treatment.

In one embodiment, the RNA disruption is expressed as an RDA score. The RDA score is reflection of the amount of RNA disruption in the sample, with increased RDA score reflecting increased RNA disruption.

As mentioned, the assays can be used to determine the likelihood that a subject will or is responding to a cancer treatment and/or their risk of progression.

Accordingly a further embodiment comprises an assay for determining if a subject is responding to a cancer treatment comprising: assaying a biological sample obtained from the subject during and/or after the subject has received a cancer treatment, optionally chemotherapy and/or radiation therapy for the quantity of RNA disruption using an RNA Disruption Assay (RDA) performed according to a method described herein, wherein the subject is identified as responding to the treatment if the amount of RNA disruption (e.g. the RDA score) is increased relative to the threshold or reference value.

In one embodiment, the responsiveness is indicative of treatment outcome, and an increased amount of RNA disruption relative to a threshold or reference value (indicative of increased chemotherapy induced RNA disruption) is predictive of a positive treatment outcome and a lack of RNA disruption relative to a threshold or reference value (e.g. indicative of little or no chemotherapy induced disruption) is predictive of negative treatment response (e.g. lack of long-term benefit).

In another embodiment, the positive treatment outcome is pathologic complete response following treatment, partial response, reduced risk of disease progression, stable disease or increased overall survival.

In one embodiment, the cancerous tumour sample assessed is obtained from a subject during and/or after the treatment, and/or the time point is, during and/or after the treatment.

In one embodiment, the methods or assays described herein are used to monitor treatment response. For example, a subsequent sample is compared to a previous sample such as a baseline sample or value. In another embodiment, the assay and methods described herein are employed in a clinical trial to assess and/or monitor which subjects are responding to the treatment. For example, subjects can be assigned treatments optionally based on expression analysis.

Biopsies can be taken, during and/or post treatment, and the RDA can be used to predict response, such as, for example, to predict if a subject is likely to benefit from remaining on a treatment (e.g. is a responder) or is likely to benefit from switching treatments thereby monitoring treatment response, adequate dosage etc. For subjects not responding according to the RDA, a subset can be switched to a new treatment. The outcome of patients that were switched can be compared to those that remained on the treatment predicted to be ineffective according to RDA score.

Accordingly in an embodiment, the method or assay further comprises selecting non-responders and randomizing participation in two or more arms of a clinical trial.

In yet another embodiment, the method or assay further comprises selecting responders and randomizing participation in two or more arms of a clinical trial.

In another aspect, the disclosure includes a method for selecting subjects for a multi-arm clinical trial, the method comprising:
predicting if the subject receiving a cytotoxic treatment such as chemotherapeutic and/or radiation treatment is responding or not responding to the treatment according to a method for determining an RDA score described herein;
randomizing non-responders to two or more treatment arms; and
optionally randomizing responders to two or more treatment arms.

A further aspect includes a method for predicting the efficacy of a cytotoxic treatment, such as a chemotherapy and/or radiation treatment, comprising:
stratifying a subject group into at least 2 subgroups;
treating the subjects of each subgroup with the chemotherapy treatment for a suitable time;
determining an RDA score for each subject according to the method described herein; and
predicting the treatment to be efficacious if the subjects have an RDA score above a threshold or reference value and predicting the treatment not to be efficacious if the subjects have an RDA score below a threshold or reference value.

Also provided is a method for predicting the efficacy of a chemotherapy treatment for a subject, comprising:
treating the subject with chemotherapy treatment for a suitable time; and
determining an RDA score according to the method described herein; wherein a treatment is predicted to be efficacious for the subject if the subject has an RDA score above a threshold or reference value and predicted not to be efficacious for the subject if the subject has an RDA score below a threshold or reference value.

If a subject is identified as not responding to a cytotoxic treatment, the subject's treatment can be altered or changed. For example, the treatment dose administered can be increased, radiation and/or a chemotherapeutic agent can be added to the regimen or the treatment can be discontinued and/or a different cytotherapy regimen initiated. The methods and assays can also be used to monitor response to the altered treatment. Other treatment modalities can also be employed if a subject is not responding to a cytotoxic, e.g. chemotherapy treatment such as radiation treatment or surgery.

Cytotoxic treatments such as chemotherapy and radiation are often administered in cycles wherein the cycle can comprise administration of 1, 2 or more doses per period, for example, per day, per week, per two week period. Protocols have been established for different drugs and different cancers. A treatment regimen can consist of 1, 2, 3, 4, 5, 6 or more cycles. Accordingly, in an embodiment, the RNA sample is at a time point after a first cycle. In another embodiment, the RNA sample that is assessed is obtained from a subject mid-treatment, and/or the time point is mid-treatment (e.g. for a 6 cycle treatment regimen, the RNA sample assessed is obtained from a subject and/or the time point is after 2, 3, or 4 cycles).

In one embodiment, the biological sample is obtained after the subject has received a first cycle of cytotoxic treatment for example a first cycle of a chemotherapeutic or radiation treatment. In another embodiment, the biological sample is obtained from the subject after the subject has received 2, 3, 4 or more cycles of the treatment. In yet another embodiment, the biological sample is obtained from the subject after completion of the treatment regimen.

In an embodiment, the biological sample is a biopsy such as a fine needle aspirate. In another embodiment the biological sample comprises a population of cancer cells isolated from the subject.

More than one biological sample can be assessed. For example, where multiple samples are taken at a time point and/or at the same time, for example, 2 or more fine needle aspirate biopsies, each sample can be assessed separately and the congruity of the samples can be assessed to determine any heterogeneity in treatment response.

In an embodiment, the RDA score indicative of responsiveness and/or positive treatment outcome correlates to a decrease in RNA integrity (e.g. increase of RNA disruption) of at least by 20%, at least 30%, at least 40%, at least 50%, at least 60%, at least 70%, at least 80% or at least 90%.

In an embodiment, the peaks are not shifted. However, the method is still applied according to the methods described herein.

In one embodiment, the methods and assays described herein are applied with non-tumour RNA samples, for example normal cells that are sensitive to a drug for example chemosensitive to a chemotherapeutic and/or radiosensitive to radiation therapy.

Without wishing to be bound by theory, it is believed that RNA disruption is a process that affects stable cells in an intermediate or non-acute response. Accordingly, the methods, assays, and products may be applicable to any cell type undergoing stimulation induced cytotoxicity e.g. RNA disruption.

It has been demonstrated that the total RNA of Jurkat T leukemia cell line was susceptible to chemical attack by doxorubicin (Fimognari et al 2009).

The assays can be applied to any tumour type and/or subtype. For example, the cancerous tumour can be a breast cancer, lung cancer, a sarcoma, prostate cancer, colon cancer or ovarian cancer including any subtype thereof. In certain embodiments, the methods and assays are applied to blood cancers such as leukemias, multiple myeloma or lymphomas. In an embodiment, the cancer is a cancer treatable by an anthracycline and/or a taxane and/or radiation. For example, prostate cancer is a cancer that can be treated by docetaxel and lung cancer and sarcomas can also be treated by anthracyclines and/or taxanes. Anthracyclines include for example doxorubicin, daunorubicin, epirubicin, idarubicin, valrubicin and mitoxantrone. Taxanes for example include paclitaxel, docetaxel, larotaxel, Abraxane, docoxahexaenoic acid-linked paclitaxel, paclitaxel polyglumex, Ortataxel, Genexol, liposomal-encapsulated paclitaxel, and paclitaxel in a Vitamin E emulsion.

Figure 10A:
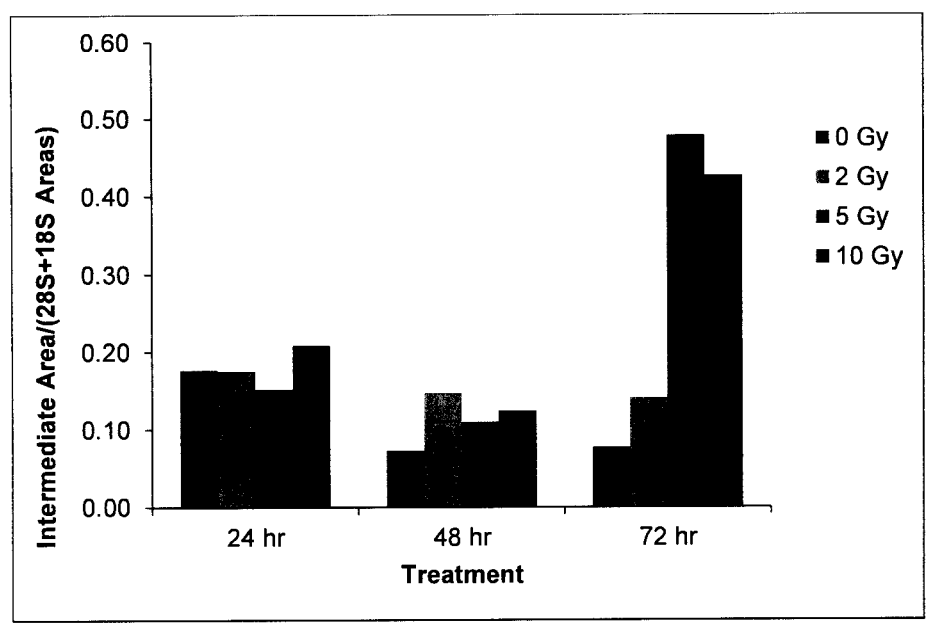
FIG. 10A is a graph of the intermediate area/(28S+18S) calculated for A2780 ovarian cancer cells treated with radiation for different time periods.
Figure 10B:
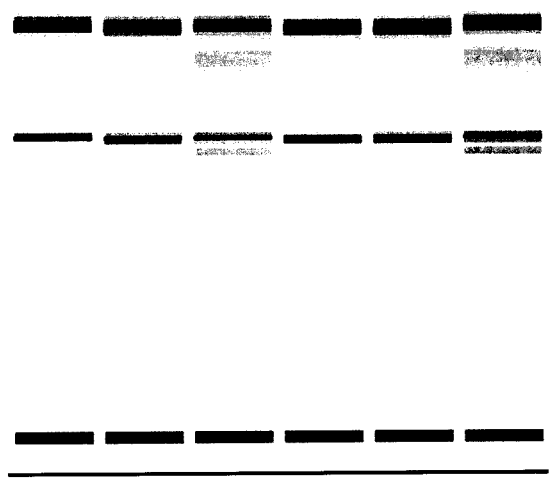
FIG. 10B is an image of a gel of electrophoretically separated A2780 ovarian cancer cell RNA samples of cells treated with radiation for different doses and time periods.
Figure 11A:
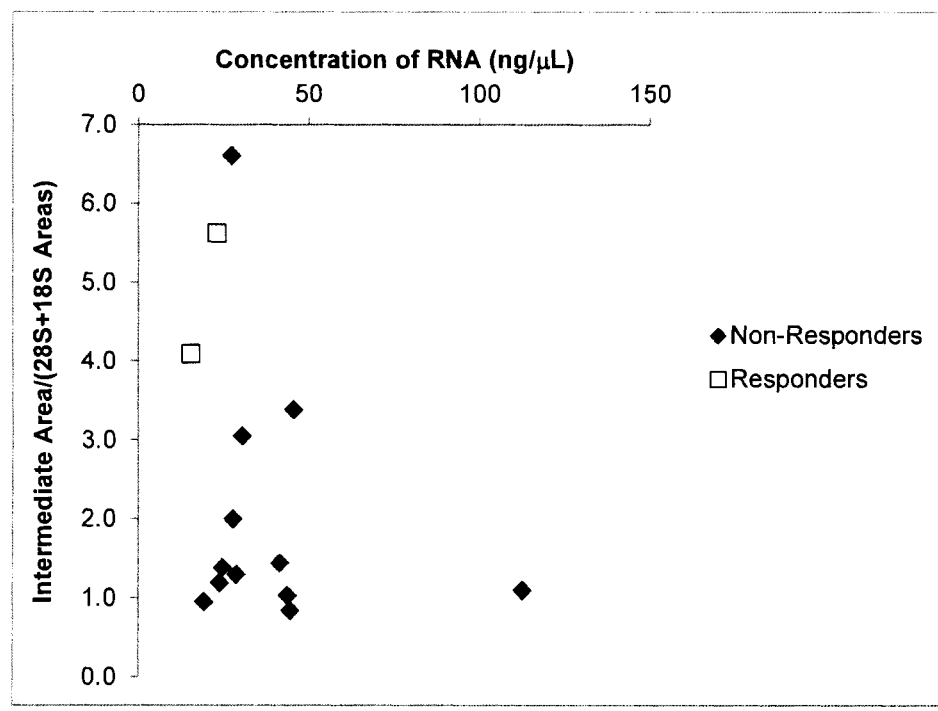
FIG. 11A is a graph of the intermediate area/(28S+18S) versus concentration calculated for patients treated with FEC, radiation and docetaxel.
Figure 11B:
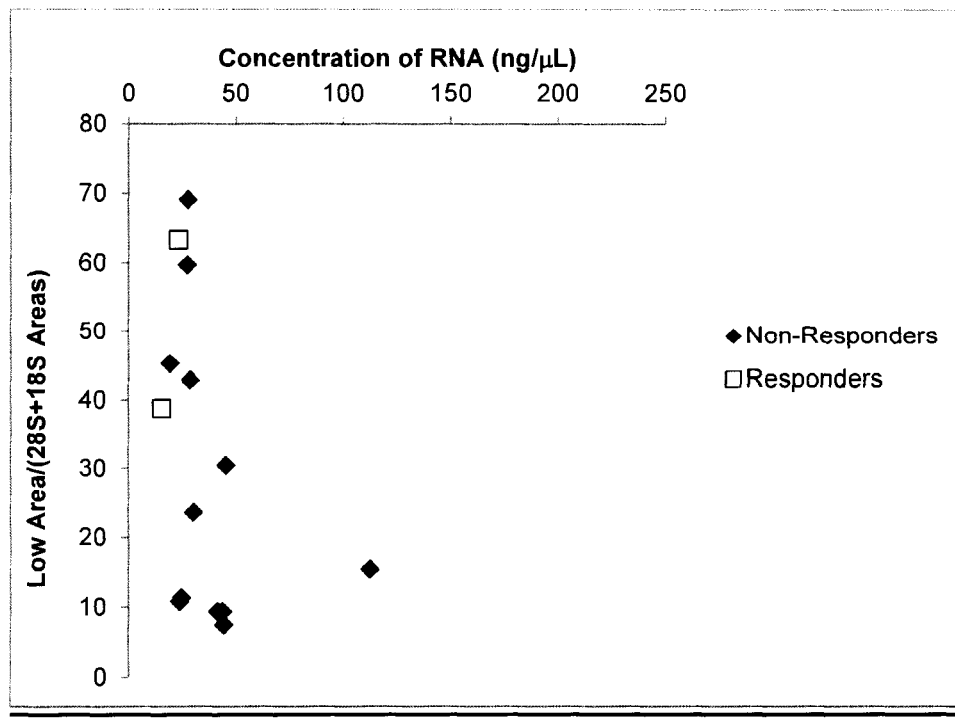
FIG. 11B is a graph of the low Area/(28S+18S) for patients treated with FEC, radiation and docetaxel.

As demonstrated for example in FIG. 10, cancer cells demonstrate RNA disruption in response to radiation treatment. FIGS. 11A and 11B provide a description of analyses where patients received chemotherapy and radiation therapy.

In an embodiment, the subject or cells have received 1, 2, 3, 4, 5, 6 or more doses of radiation. In an embodiment, the cells and/or subject are treated with a dose of a chemotherapeutic agent prior to or concurrent with radiation treatment.

The MA22 dataset for example, included samples with differing ER, PR, Her2, topoisomerase status. As demonstrated in the Examples section, the method and assays described herein are applicable independent of ER, PR, Her2, topoisomerase status. The methods have been used to assess breast cancer samples that vary in ER, PR and Her2 status including triple negative samples.

In one embodiment, the cancerous tumour is selected from breast cancer, prostate cancer, colon cancer and ovarian cancer or any subtype thereof.

In an embodiment, the cancerous tumour is selected from leukemia, lymphoma or multiple myeloma and/or any cancer treatable by an anthracycline and/or taxane.

In one embodiment, the cancerous tumour is breast cancer.

In another embodiment, the breast cancer is HER2+ positive breast cancer.

A further aspect includes a method of treating a subject with cancer in need thereof comprising:

administering a cytotoxic treatment optionally a chemotherapeutic and/or radiation treatment;

determining if the subject is responding to the treatment according to a method disclosed herein; and continuing administration of the treatment if the subject is responding and/or discontinuing administration of the treatment is the subject is not responding.

In an embodiment, the cytotoxic treatment dose, e.g. chemotherapeutic dose, is increased, for example wherein a subject sample includes an intermediate level of RNA disruption, for example RDA zone 2. As subjects who fall within RDA zone 3, are more likely to be pathological complete responders, a subject whose RDA score does not fall within RDA zone may benefit from increased treatment dose.

In an embodiment, the chemotherapeutic treatment is selected from microtubule stabilizing agents such as Docetaxel and paclitaxel, DNA synthesis inhibitors such Epirubicin, inhibitors of Her2 Receptor such as Trastuzumab, DNA cross-linking agents such as Mafosfamide, carboplatin and cisplatin, VEGFA inhibitors such as Bevacizumab, Receptor Tyrosine Kinase inhibitors such as Sunitinib and Toceranib, Bisphosphonates such as Zoledronic acid, and Thymidylate synthase inhibitors such as 5-fluorouracil.

In one embodiment, the chemotherapeutic treatment is selected from taxanes, anthracyclines, and vinca alkaloids such as vinblastine, alkylating agents such as cisplatin and nucleoside analogs such as 5-FU and combinations thereof. In an embodiment, the chemotherapeutic treatment comprises a drug selected from docetaxel, paclitaxel, epirubicin, doxorubicin, vinblastine and cisplatin and/or combinations thereof. In an embodiment, the taxane is selected from paclitaxel, docetaxel, larotaxel, Abraxane, docoxahexaenoic acid-linked paclitaxel, paclitaxel polyglumex, Ortataxel, Genexol, liposomal-encapsulated paclitaxel, and paclitaxel in a Vitamin E emulsion.

Breast cancer can be treated, for example, with taxanes, anthracyclines or, for example, paclitaxel, docetaxel, docetaxel and epirubicin and combinations thereof.

Ovarian cancer can be treated, for example, with taxanes, anthracyclines, and vinca alkaloids such as vinblastine, alkylating agents such as cisplatin and nucleoside analogs such as 5-FU and combinations thereof.

In an embodiment, the RNA integrity is determined for total RNA. In another embodiment, the RNA integrity is determined for ribosomal RNA. Ribosomal RNA includes, for example, 28S, 18S, 5.8S and 5S rRNA.

The methods, assays and products described herein can also be used to assess autolytic degradation. For example, autolytic degradation can be assessed by determining the Area of LowA/Total Area. Measurement of this feature using xenograft tumours incubated with saline for increasing lengths of time, demonstrates that autolytic degradation can be measured more often and may be measured more accurately than what is possible using BioAgilent's RIN software. For example, using the ratio of Low A Area/Total Area, a more precise mapping of the extent of autolytic degradation may be measured.

At least some of the elements of the methods that are described herein that are implemented via software may be written in a high-level procedural language such as object oriented programming or a scripting language. Accordingly, the program code may be written in C, C++, SQL or any other suitable programming language and may comprise modules or classes, as is known to those skilled in object oriented programming. At least some of the elements of the methods described herein that are implemented via software may be written in assembly language, machine language or firmware as needed. In either case, the program code can be stored on a storage media or on a computer readable medium that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner in order to perform at least one of the methods described herein.

Furthermore, at least some of the methods described herein are capable of being distributed in a computer program product comprising a computer readable medium that bears computer usable instructions for one or more processors. The computer readable medium may be provided in various non-transitory forms and other forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer-useable instructions may also be in various forms, including compiled and non-compiled code.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure.

EXAMPLES

Example 1

The media used in these experiments contained 5% FBS; 50% media is media diluted in PBS (1:1).

RNA was isolated from a core biopsy of a MCF-7 tumour xenograft that has been kept at room temperature in saline for 24 hours where autolytic degradation takes place and separated using an Agilent 2100 Bioanalyzer.

RNA was isolated from ovarian cancer cell line A2780 cells which had been treated with 10 μM docetaxel in 50% media or 20 μM epirubicin, each in 50% media. Cells were treated with the chemotherapeutic for 24 hours at 37° C. Isolated RNA was separated by microcapillary electrophoresis using the Agilent 2100 Bioanalyzer.

FIGS. 1-3 show electropherogram traces of the MCF-7 tumour RNA kept at room temperature with saline resulting autolytic RNA degradation (FIG. 1) and A2780 tumour cell RNA treated with chemotherapy drugs docetaxel and epirubicin (FIG. 2 and FIG. 3 respectively).

Xenograft tumour kept in saline for 24 hours shows a large peak of small fragments at approximately the 26 second mark of the trace (FIG. 1). There is also a loss of area of the 28S peak. Cancer cells treated with chemotherapeutic drugs show a different pattern of RNA disruption. For example, FIG. 2 which shows human ovarian cancer cell line A2780 treated with chemotherapeutic docetaxel, shows an intermediate peak and a peak adjacent to the 18S peak. FIG. 3 shows A2780 cells treated with chemotherapeutic epirubicin. The electropherogram shows intermediate bands between the 18S and 28S peaks. In addition, the location of the detected 28S and 18S peaks are shifted relative to the 18S and 28S peaks compared to intact RNA and autocatalytic RNA degradation.

Figure 8A:
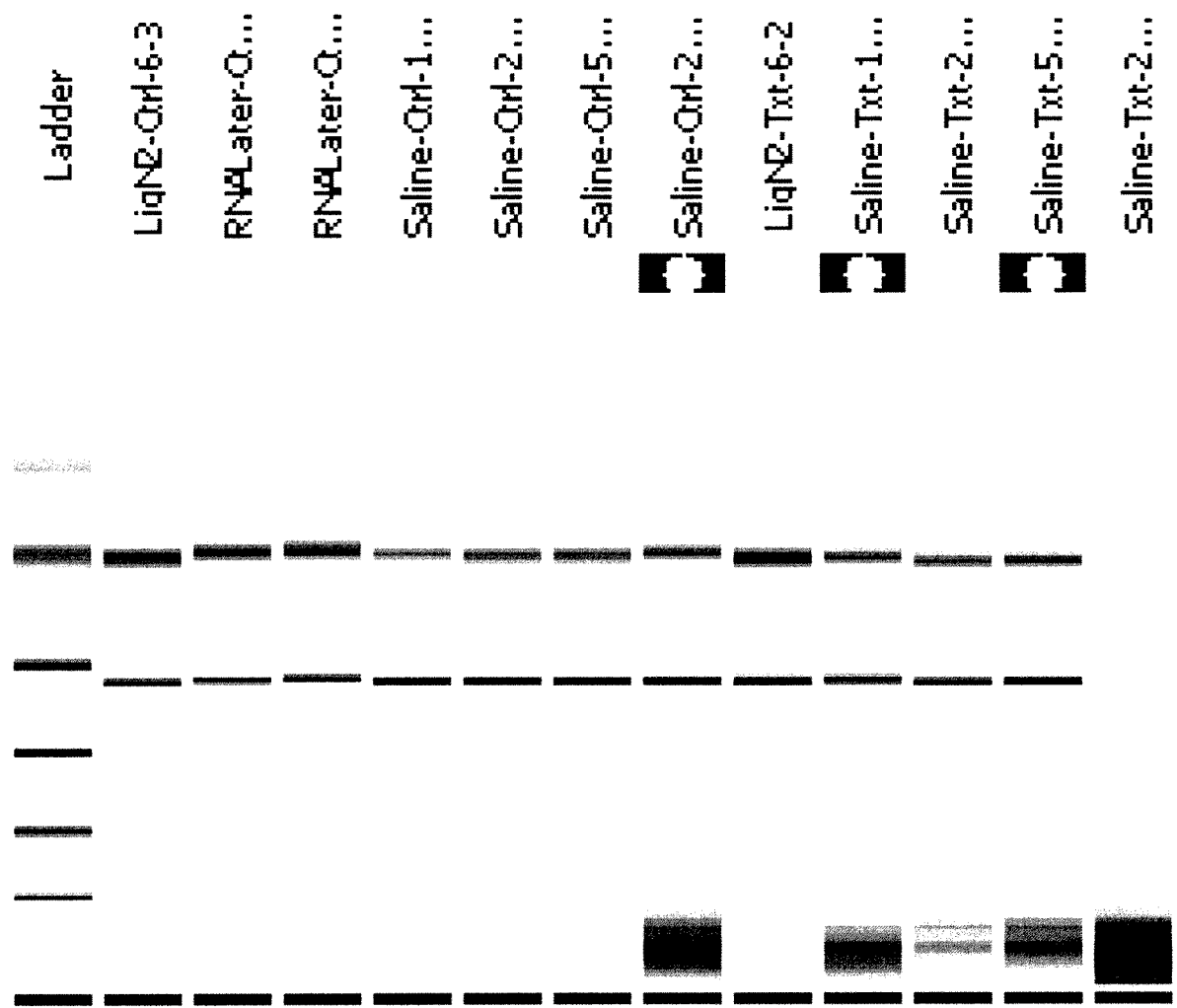
FIG. 8A is an image of a gel of electrophoretically separated xenograft tumour RNA samples.
Figures 8B, 8C:
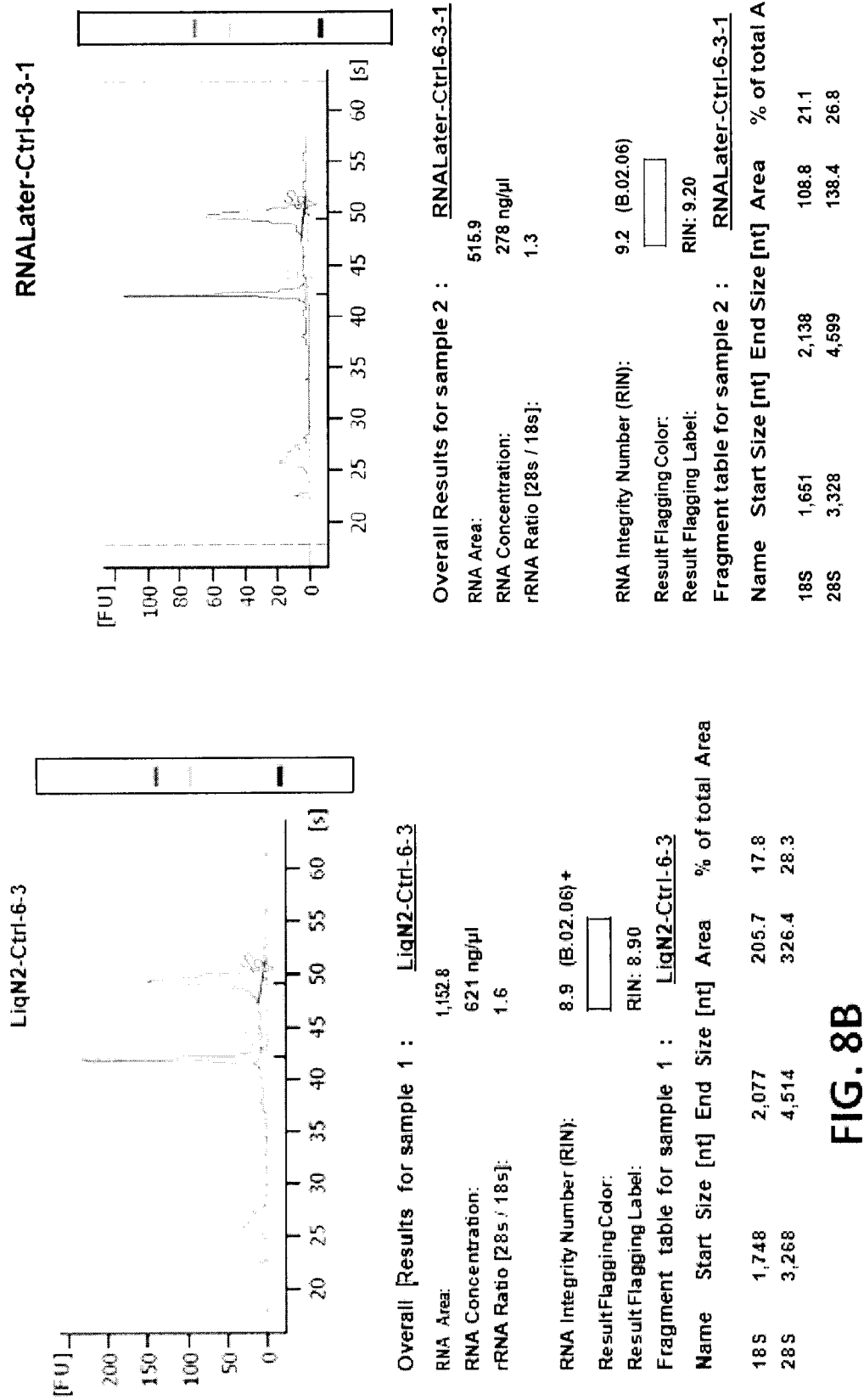
FIG. 8B is an illustration of an electropherogram trace of lane 1 of the gel of FIG. 8A.
FIG. 8C is an illustration of an electropherogram trace corresponding to lane 2 of the gel of FIG. 8A.
Figures 8D, 8E:
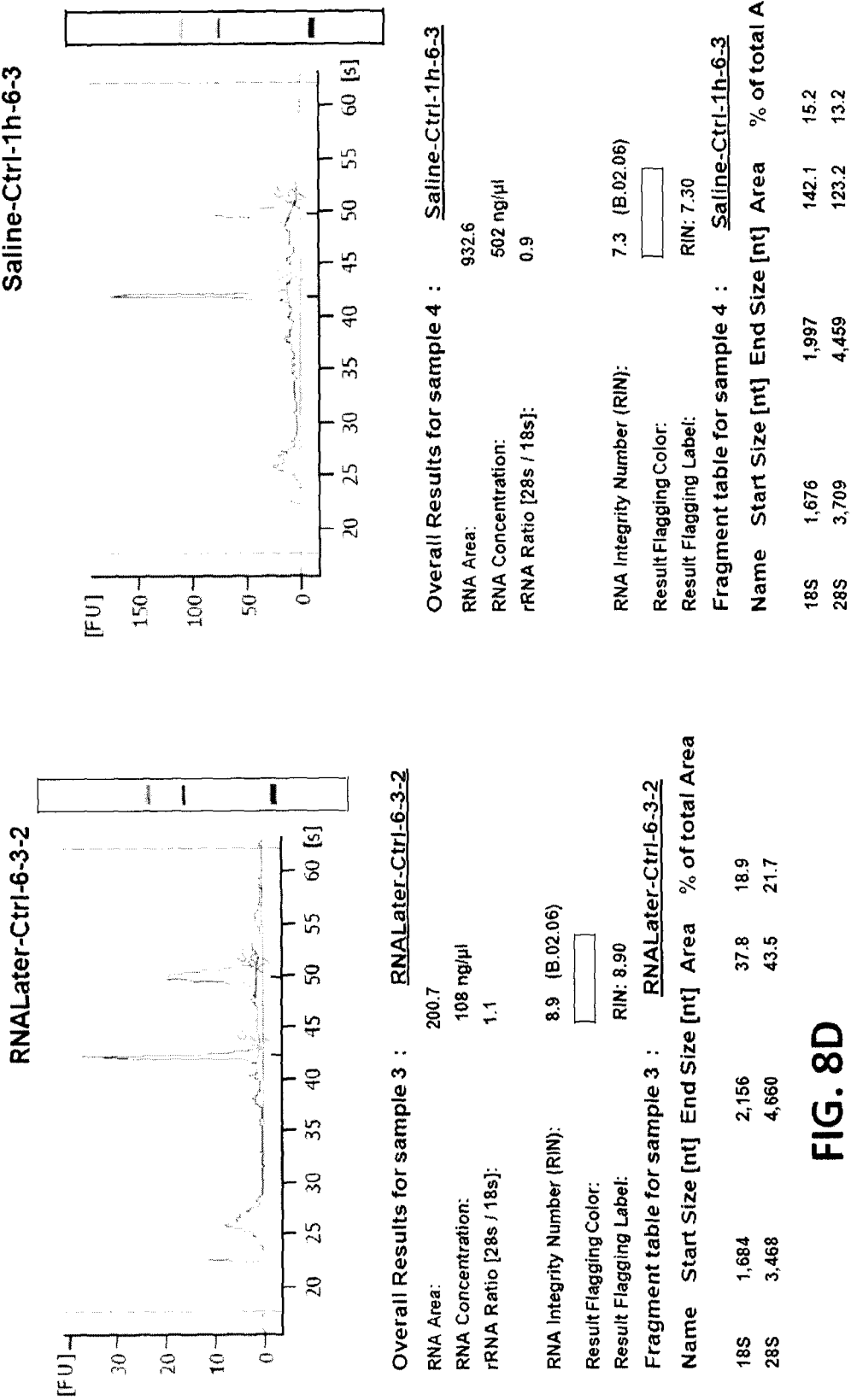
FIG. 8D is an illustration of an electropherogram trace corresponding to lane 3 of the gel of FIG. 8A.
FIG. 8E is an illustration of an electropherogram trace corresponding to lane 4 of the gel of FIG. 8A.
Figures 8F, 8G:
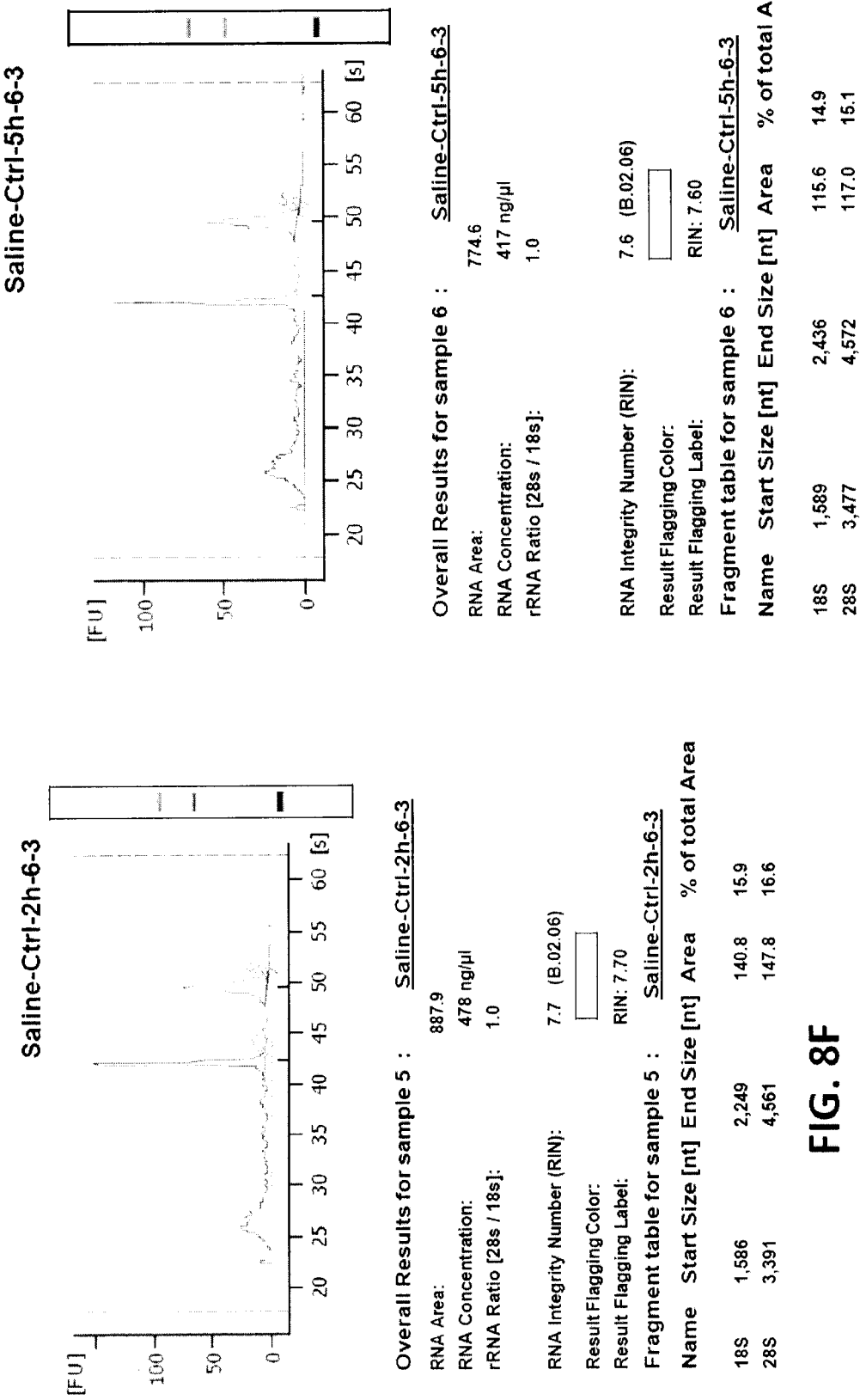
FIG. 8F is an illustration of an electropherogram trace corresponding to lane 5 of the gel of FIG. 8A.
FIG. 8G is an illustration of an electropherogram trace corresponding to lane 6 of the gel of FIG. 8A.
Figures 8H, 8I:
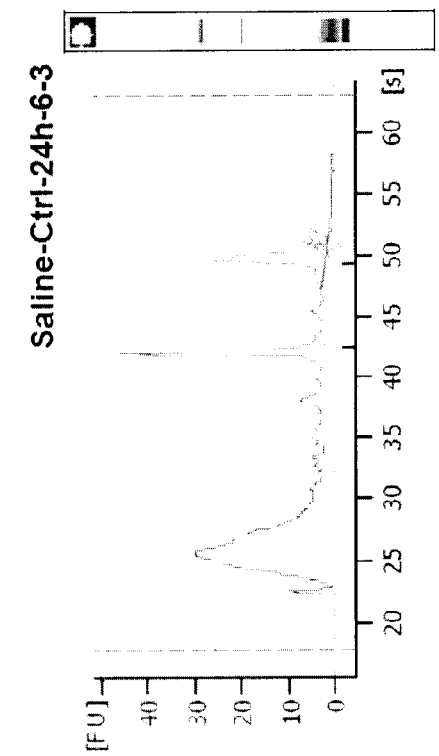
FIG. 8H is an illustration of an electropherogram trace corresponding to lane 7 of the gel of FIG. 8A.
FIG. 8I is an illustration of an electropherogram trace corresponding to lane 8 of the gel of FIG. 8A.
Figure 8J:
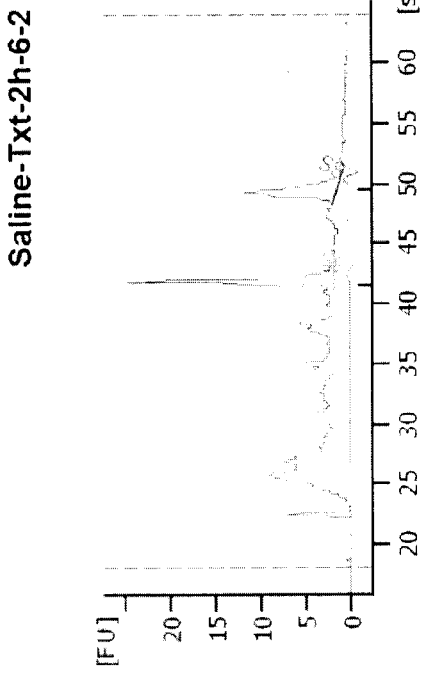
FIG. 8J is an illustration of an electropherogram trace corresponding to lane 9 of the gel of FIG. 8A.
Figure 8K:
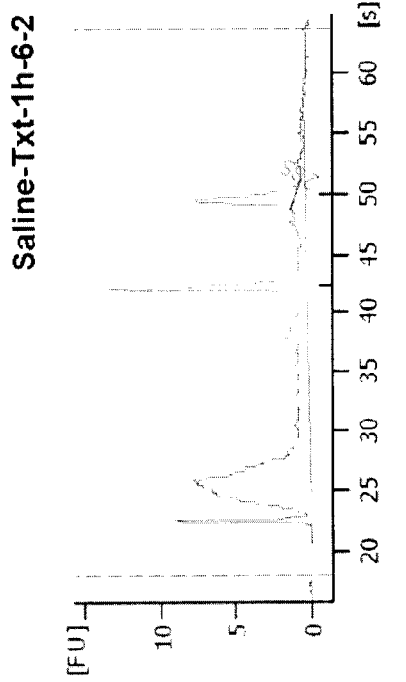
FIG. 8K is an illustration of an electropherogram trace corresponding to lane 10 of the gel of FIG. 8A.
Figures 8L, 8M:
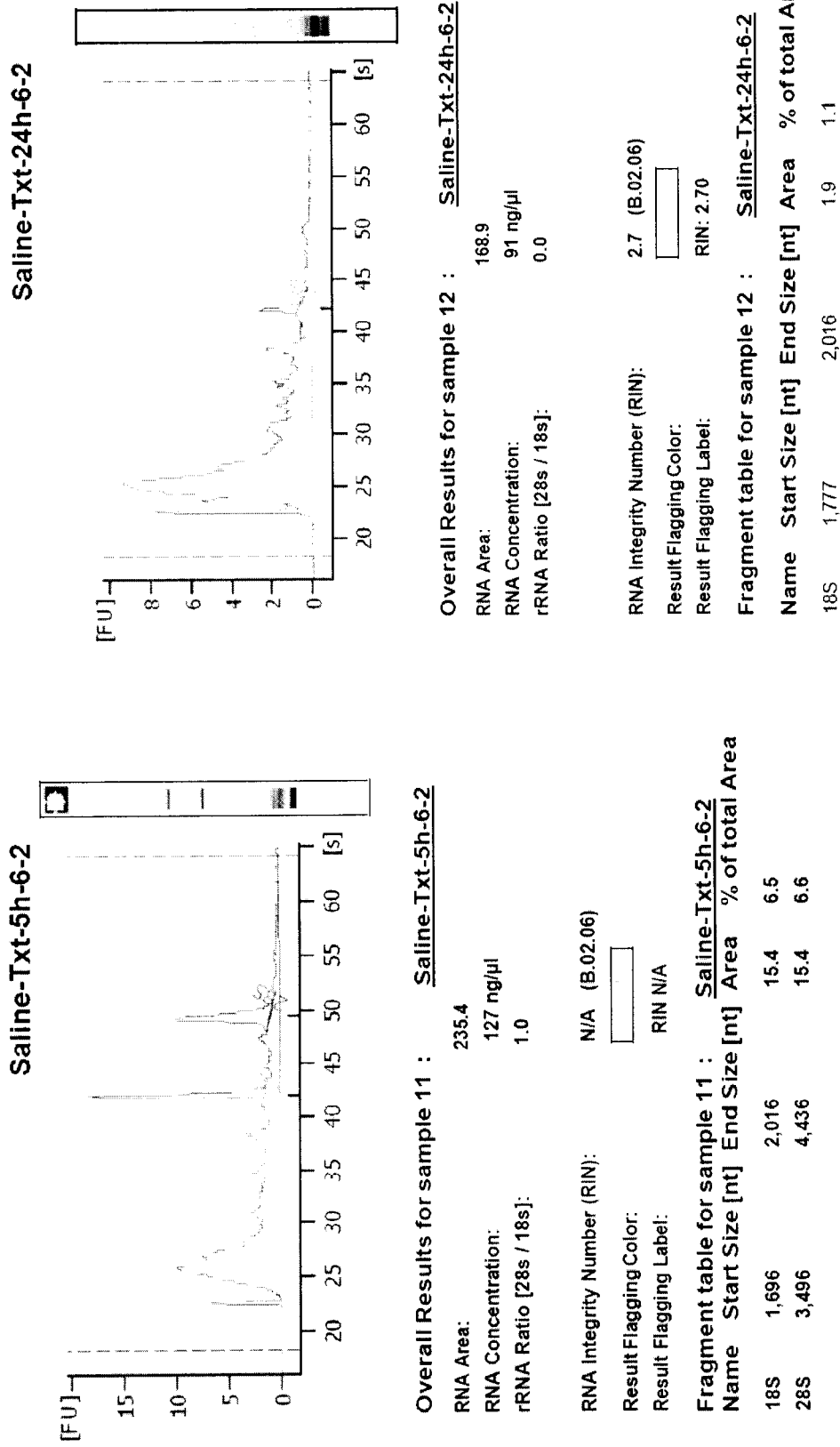
FIG. 8L is an illustration of an electropherogram trace corresponding to lane 11 of the gel of FIG. 8A.
FIG. 8M is an illustration of an electropherogram trace corresponding to lane 12 of the gel of FIG. 8A.

RNA isolated from xenograft tumours stored in liquid nitrogen, RNALater™ solution or left in saline for 1 h, 2 h, 5 h and 24 h to induce autocatalytic degradation was analyzed by measuring an RNA Integrity Number (RIN) using Agilent 2100 Bioanalyzer. FIGS. 8B-8M shows that the 28S and 18S peaks are not misidentified by this software in RNA samples with autolytic degradation (samples 4-7 and 9-12 of FIG. 8A). Circles above the gel lanes indicate that an RIN number could be calculated (FIG. 8A). Circles encapsulated by squares indicate samples for which an RIN number could not be calculated. Control samples were untreated xenograft tumours (1-7). Treated samples (8-12) were given docetaxel.

Example 2

The MA22 RNA electropherogram data was examined to determine which components of the electropherogram best correlated with clinical response. It became evident that the Agilent Bioanalyzer software misidentified either the 28S peak or the 18S peak on electropherograms in >20% of the samples. In these samples, a small portion of the tip of a peak was identified as the whole peak. The Agilent 2100 Bioanalyzer software (Agilent Expert) (Mueller 2004; Vespucci 2005) was able to correctly identify the 28S and 18S peaks on electropherograms of intact RNA which are identifiable by eye. However, in samples with disrupted RNA, electropherogram peaks were misidentified by Agilent RIN software although the correct peaks remained in appropriate locations visually on the electropherogram. The Agilent method which generates RIN values, hereafter referred to as the RIN algorithm, was based on RNA samples which were either intact or had undergone complete autolytic degradation and had few "partially degraded" samples (Schroeder, Mueller et al. 2006).

Accordingly, methods were used to determine an RDA score herein, as described with respect to FIGS. 5A and 5B, which are different from the methods used to calculate RIN. The output RDA scores were subjected to Receiver Operating Characteristic (ROC) analysis to generate an ROC curve from which the Area under the Curve (AUC) was calculated (Hurley 2011). The ROC curve was then used to determine the utility in discriminating Responders from Non-Responders using certain features of the electropherogram (as measured by a pathological complete response post-treatment).

Assessment of RNA Quality and Concentration Using an Agilent 2100 BioAnalyzer with Agilent RNA 6000 Nano Kits and Caliper Technology's RNA Nanochips:

The procedure used for assessing the quantity and integrity (also referred to as RNA quality) of the above RNA preparations involved capillary electrophoresis on an Agilent 2100 Bioanalyzer (Agilent Technologies, Mississauga, ON) using a protocol described in detail in the Agilent RNA 6000 Nano Kit Guide available on the Agilent Technologies website (Agilent Publication Part Number: G2938-90035).

The protocol document includes a detailed description on setting up the assay equipment, preparing and running the RNA Nanochips, and analysis of the capillary electrophoretic data using the Agilent 21000 Bioanalyzer and its associated "Expert software". The document includes "Essential Measurement Practices" to be followed. RNA 6000 "Nanochips" and associated solutions are obtained in RNA 6000 Nano kits that can be purchased from Agilent Technologies (Mississauga, ON). RNA Nanochips are manufactured by Caliper Life Sciences (Hopkinton, Mass.). The sizes of the rRNAs, and the concentration of RNA in a given sample are determined by extrapolation from a standard curve of reference RNAs provided in the RNA 6000 NANO kits. Data from the Bioanalyzer runs were stored as PDF and XAD files. The Agilent 2100 Expert software was used to obtain all data from the capillary electrophoresis runs, including the size of RNAs and the RNA integrity/ quality and quantity for a given RNA preparation. Raw data from each electropherogram was then exported from the XAD files into EXCEL files which contain the raw electropherogram data at time intervals of 0.05 s.

Peak Identification Code

Based on the methods described herein, the current error rate for peak misidentification is 3% for chemotherapy treated samples.

Results of Area and Ratio Calculations

The error rate for the correct identification of 28S and 18S peaks fell from 25% to 3% using the described method. Included as errors were 28S and 18S peaks that were merged into the "intermediate banding" region resulting in small values for the area under the peak. Including only the mid-identification of the 28S and 18S peaks in electropherograms in which the RNA ran aberrantly gave an error rate of 1%. All ratio values of "0" were eliminated using this method and samples that were assigned RIN values of N/A by the Agilent Bioanalyzer were then quantifiable.

TABLE 1

Error Types within MA22 Electropherograms
Type of Error

Peak before 28S
All peaks shifted
Large amount of lower banding with absence of 18S and 28S
Large intermediate peak with absence of 28S and 18S
Large intermediate peak with merged 28S and 18S Samples used to assess RDA were taken after the third cycle of chemotherapy. The analysis of pre-therapy samples found that RNA integrity/quality and quantity were generally high and could not discriminate between Responders and non-Responders. In vitro studies and treatment of tumours in xenograft mouse models suggest that assessment of RNA disruption could demonstrate an effect as early as after the first cycle of chemotherapy.

The ratio of 28S:18S was calculated based on new area values. In intact RNA the accepted maximum value of 28S:18S is 2.0 (Sambrook, Fritsch, & Maniatis, 1989). This ratio has been shown to change in aging (Mori, Mizuno et al. 1978) (Payao, Smith, Winter, & Bertolucci, 1998), in diseases such as Alzheimer's (da Silva, Payao, Borsatto, Bertolucci, & Smith, 2000) and atherosclerosis (Martinet, De Meyer, Herman, & Kockx, 2004).

Previous work has indicated that during autolytic RNA degradation the height of the 28S peak decreases more rapidly than the height of the 18S peak (Schroeder, et al., 2006). However, in chemotherapy disrupted RNA, this ratio can decrease indicative of a preferential loss of 28S and was also found to increase indicating an increased rate of fragmentation of the 18S peak compared with the 28S peak. This ratio may be useful to discriminate between intact and chemotherapy disrupted RNA but would require two cutoff values such that values greater than approximately 2.5 or less than approximately 1.3 are indicative of chemotherapy disrupted RNA. An increased ratio is not typically found with autolytic degradation.

Abnormal 28S:18S ratios have been found in other systems such as connective tissue and tumour tissue (Skrypina et al. 2003) as well as in pure spermatozoal fractions in which 28S depletion results in a significantly lower ratio (median 0.11) than that described for somatic cells (Cappallo-Obermann, Schulze et al. 2011). It has been suggested that this loss in 28S is due to preferential cleavage within GC-rich regions (Johnson, Sendler, Lalancette, Hauser, Diamond, & Krawetz, 2011).

Figure 6A:
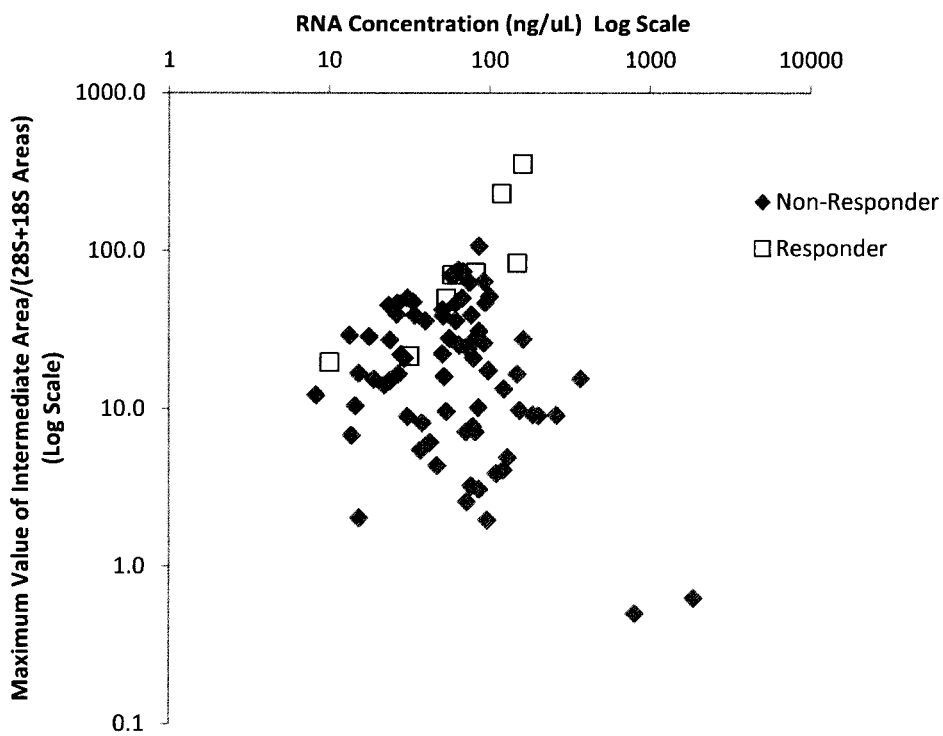
FIG. 6A is a log-log graph of the feature of log (Maximum Intermediate/(28S+18S)) versus log RNA concentration.

The area of the intermediate banding region was measured and ratios calculated to normalize to the total area (i.e. intermediate/total area) and to determine how the area of intermediate banding region compares with the area of the 28S and 18S peaks (i.e. intermediate/(28S+18S)). The area in the low banding region (below the 18S peak) was also calculated. Other ratios were also calculated including intermediate/28S, intermediate/18S, (low+intermediate)/(28S+18S) and low banding region/total area. Minimum and maximum ratios were determined for several electropherograms of samples that were taken at the same time and graphed against concentration, an example of which is shown in FIG. 6A. Accordingly, if a feature uses the term maximum or minimum then this means that a ratio was calculated for each electropherogram dataset and then the maximum or minimum of these ratios was calculated as the case may be.

In the ratios of the features that follow below, the term "intermediate" means the area in the intermediate region, the term "28S" means the area of the 28S peak, the term "18S" means the area of the 18S peak, the term "low banding" means the area of the low banding region and the term "total area" means the sum of the areas of the low banding region, the 18S peak, the intermediate region and the 28S peak. The term concentration (for the graphs in FIGS. 6A-6D and FIGS. 6F-6K) means the concentration of the RNA in the samples from which the electropherogram was generated. In the cases where the maximum or minimum was taken of a ratio, the concentration used in the plot was that of the electropherogram dataset that had the maximum or minimum value for the ratio.

Figure 6B:
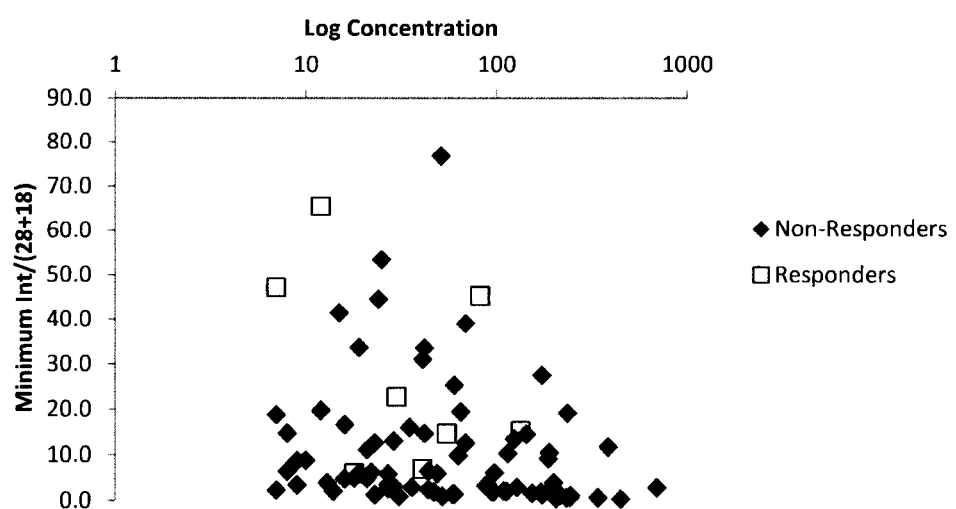
FIG. 6B is a semi-log graph of the feature of Minimum Intermediate/(28S+18S) versus log RNA concentration for a sample study.

The AUC value for the feature of maximum intermediate/(28S+18S) was 0.81 and the AUC value for the ratio of minimum intermediate/(28+18) was 0.75 indicating that both of these ratios are able to discriminate between Responders and Non-Responders. The AUC was the area under the ROC curve. The ROC curve was obtained by applying thresholds to the RDA score that was generated based on the indicated feature. A log-log graph of the first combination of features versus log concentration is shown in FIG. 6A and a semi-log graph of the second combination of features versus log concentration is shown in FIG. 6B.

Figure 6C:
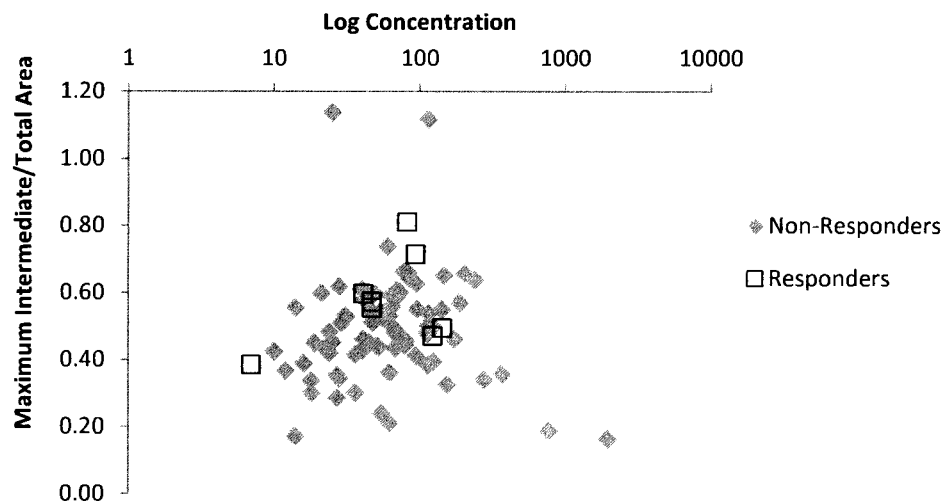
FIG. 6C is a semi-log graph of the feature of Maximum Intermediate/Total Area versus log RNA concentration for a sample study.

The AUC value for the feature of maximum intermediate/total area was 0.71 and the AUC value for the ratio of minimum intermediate/total area the AUC was 0.56. A semi-log graph of the feature of maximum intermediate/total area versus log concentration is shown in FIG. 6C.

Figure 6D:
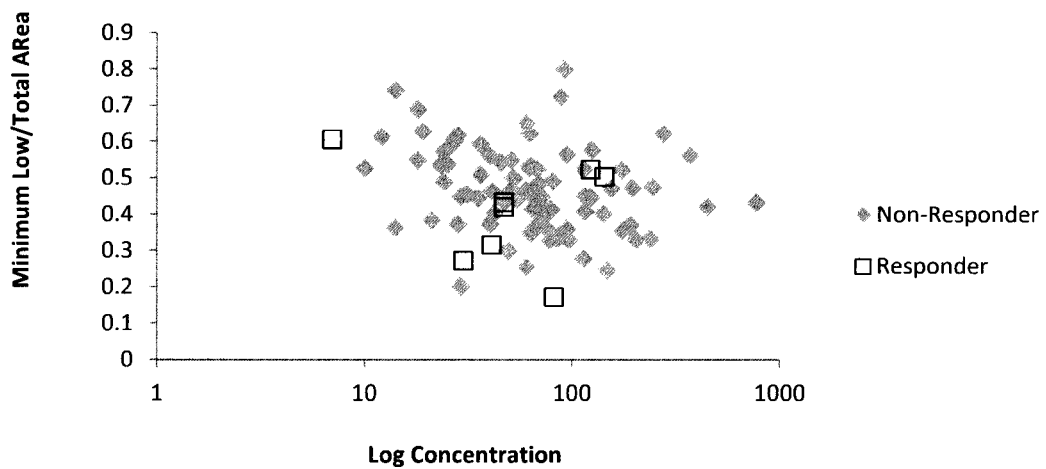
FIG. 6D is a semi-log graph of the feature of Minimum Value Low Banding/Total Area versus log RNA concentration for a sample study.
Figure 6E:
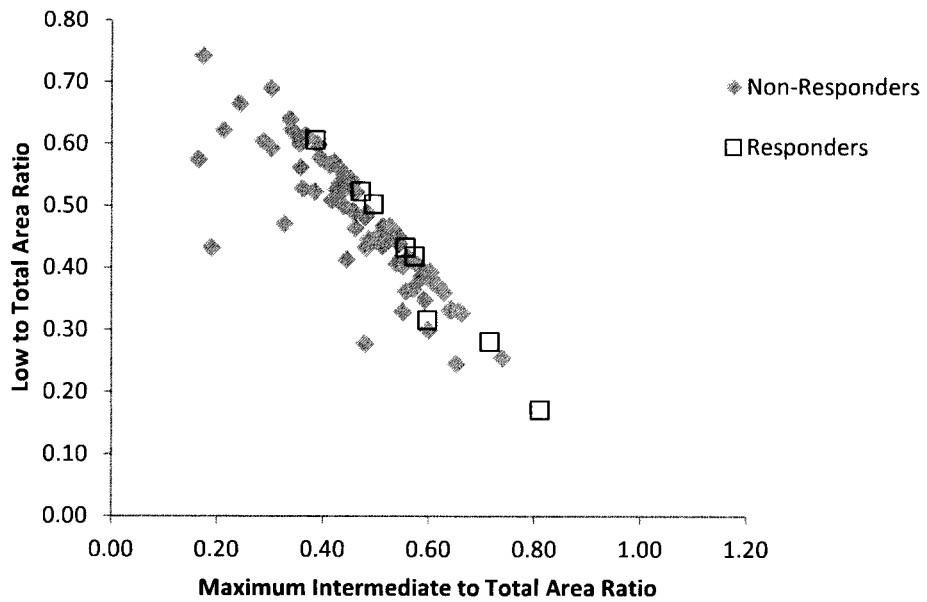
FIG. 6E is a graph of the feature Low to Total Area ratio versus Maximum Intermediate to Total Area ratio for a sample study.

The AUC value for the feature of minimum Low Banding/Total Area was 0.63; however the AUC value for the feature of maximum Low Banding/Total Area value was 0.50. A semi-log graph of the feature of minimum low banding/total area versus log concentration is shown in FIG. 6D. The feature of low banding/Total area may be a useful feature in combination with other components as shown in FIG. 6E.

Figure 6F:
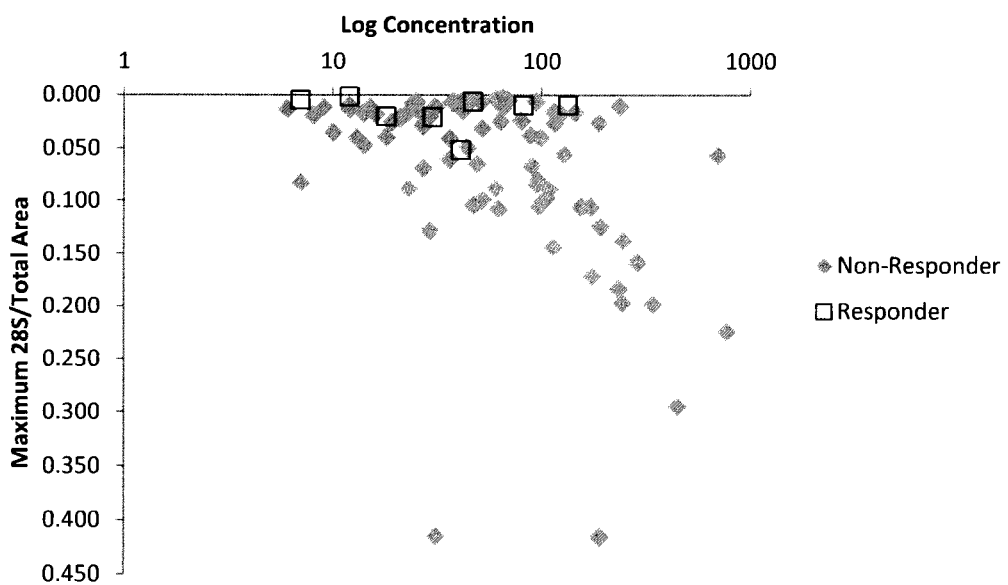
FIG. 6F is a semi-log graph of the feature of Maximum 28S/Total Area versus log RNA concentration for a sample study.
Figure 6G:
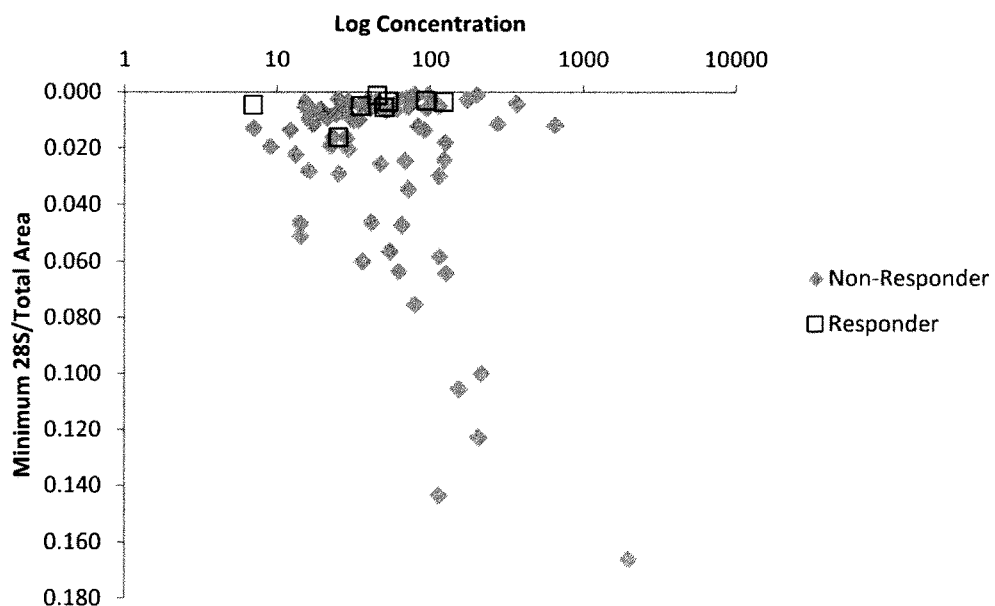
FIG. 6G is a semi-log graph of the feature of Minimum 28S/Total Area versus log RNA concentration for a sample study.
Figure 6H:
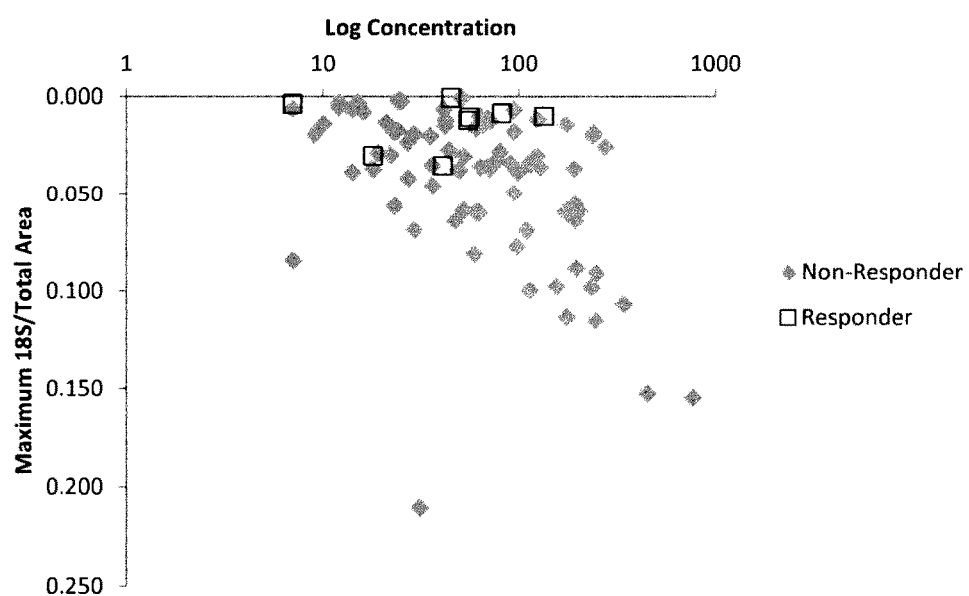
FIG. 6H is a semi-log graph of the feature of Maximum 18S/Total Area versus log RNA concentration for a sample study.
Figure 6I:
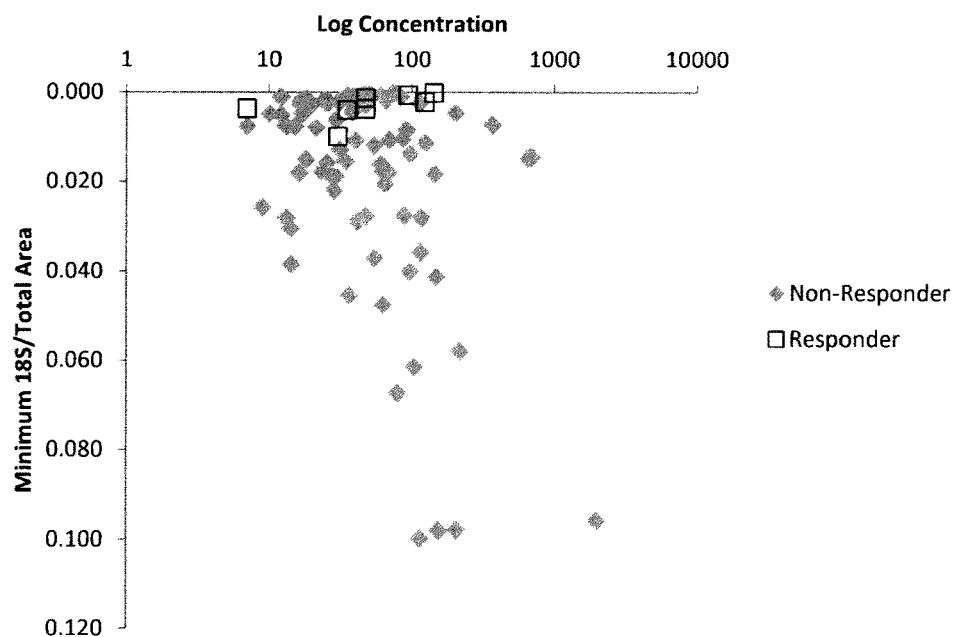
FIG. 6I is a semi-log graph of the feature of Minimum 18S/Total Area versus log RNA concentration for a sample study.

Ratios were also generated for the area of the 28S peak over (i.e. with respect to or divided by) total area (28S/total area) and the area of the 18S peak over total area (18S/total area). The features of maximum and minimum ratios of 28S/total area were graphed against log concentration on semi-log graphs as shown in FIGS. 6F-6G, respectively. The features of maximum and minimum ratios of 18S/total area were graphed against log concentration on semi-log graphs as shown in FIGS. 6H-6I, respectively.

The AUC value for the feature of maximum 28S/Total Area was 0.69. The AUC value for the feature of minimum 28S/Total Area was 0.62. The AUC value for the feature of maximum 18S/Total Area was 0.76. The AUC value for the feature of minimum 18S/Total Area was 0.68. This suggests that these features may be useful components to separate Responders from Non-Responders.

Figure 6J:
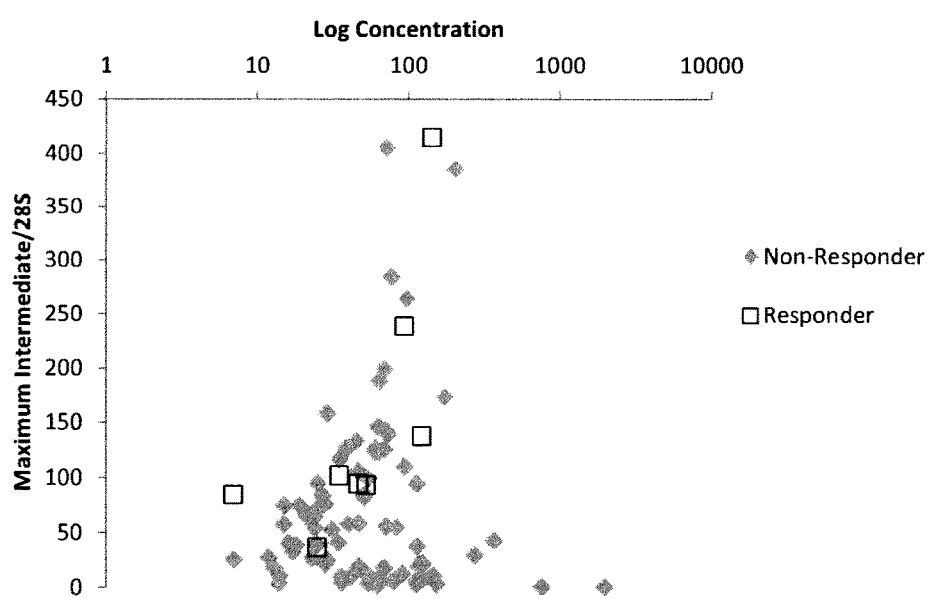
FIG. 6J is a semi-log graph of the feature of Maximum Intermediate/28S versus log RNA concentration for a sample study.
Figure 6K:
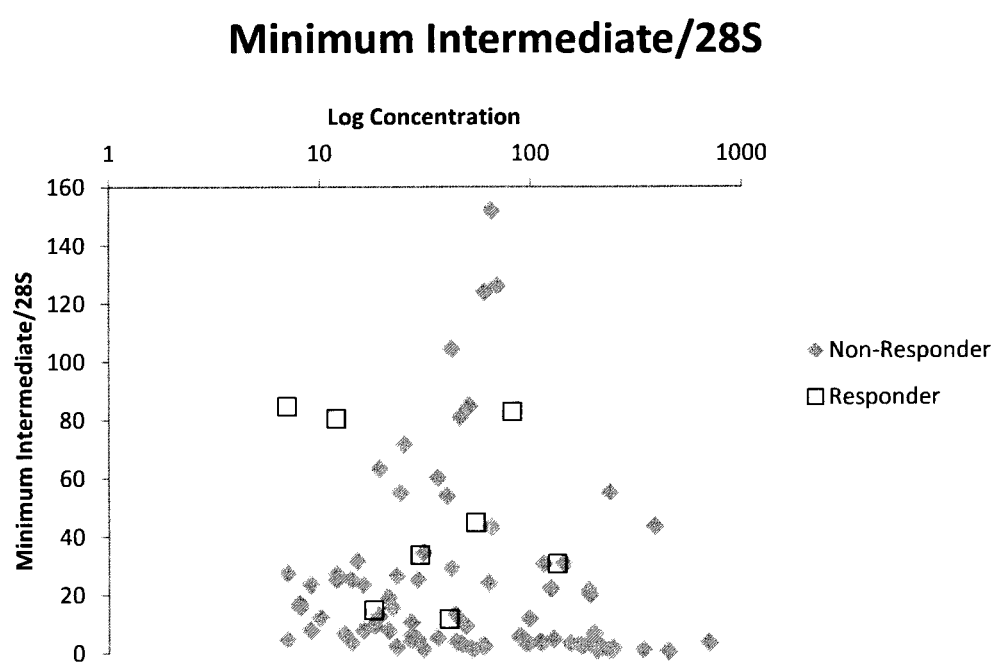
FIG. 6K is a semi-log graph of the feature of Minimum Intermediate/28S versus log RNA concentration for a sample study.

The features of maximum and minimum ratios of Intermediate/28S are shown in FIGS. 6J-6K.

The 18S and 28S peak widths were calculated for the MA22 dataset and assessed for their ability to discriminate between Responders and Non-Responders. The accuracy (e.g. (the number of data whose true labels equal to their predicted labels)/(the total number of data)) as determined by linear discriminant analysis of using this combination of features to generate the RDA score was 0.6 and had an AUC of 0.67.

RNA Disruption Vs RNA Autolytic Degradation

Distinguishing between the fragmentation effect of drugs and autolytic degradation may be possible using A) changes in electropherogram graphical baseline (i.e. measure of the base between the peaks), B) appearance of low molecular weight banding, C) low RNA concentration and/or D) measuring loss of 28S compared with 18S peaks.

Discussion

As reported herein the electropherograms of autolytic RNA degradation can differ from chemotherapy induced RNA disruption. Existing tools for analyzing RNA degradation have not been directed to assessing non-autolytic degradation. Accurate analysis of the RNA electropherograms is key to determining the extent of disruption in tumour RNA samples that have been treated with chemotherapy. The disclosed peak identification method provides the ability to fully analyze an increased number of samples since samples that were previously marked an RIN of N/A by the Agilent Bioanalyzer were assessed and area values generated using the methods described herein. Features associated with rRNA disruption by chemotherapy are listed in TABLE 2.

TABLE 2

Features Associated with rRNA Disruption by Chemotherapy

| Feature | Effect |
|---|---|
| 28S peak | Loss of area, peak height, peak width |
| 18S peak | Loss of area, peak height, peak width |
| 28S:18S ratio | Increase or decrease |
| Intermediate banding | Area, peak height, discrete banding? |
| Low banding | Area, peak height, discrete banding |

The maximum ratio of 28S to 18S has been commonly assigned the value of 2.0; and a fall in this ratio has been ascribed to degradation (e.g. less than 1.8). In the study of Example 2, it was found that in samples with disrupted RNA, the 28S:18S ratio either decreased, or in some cases increased. In both cases, strong intermediate banding was present. The extent of fragmentation of the 28S differed from the fragmentation occurring in the 18S rRNA.

The intermediate banding region appears to be an important component in the RNA electropherogram when determining the extent of fragmentation of RNA (e.g. RNA disruption). The appearance of banding in the intermediate region along with 28S and/or 18S bands that make up smaller proportions of the total area indicate a disruption of RNA.

Example 3

The need for a prognostic biomarker to assess long term breast cancer chemotherapy efficacy is well established. The RNA Disruption Assay (RDA) is a novel prognostic test for women undergoing neoadjuvant chemotherapy that enables assessment of drug efficacy during treatment. RDA was developed from the findings of a clinical trial for women with locally advanced breast cancer (CAN-NCIC-CTG MA-22). Varying doses of docetaxel and epirubicin were given at two weekly (dose dense) or three weekly intervals. Tumours were biopsied in duplicate at 3 time points; pre-therapy, mid-therapy and post-therapy. Trial endpoints included clinical response, pathological complete response (pCR), disease-free survival and overall survival.

Methods:

RDA is based on analysis of RNA electropherograms generated to assess RNA integrity/quality. At mid-therapy, patients with tumours responding to treatment exhibited a dramatic reduction in RNA quality (RNA disruption). A method to provide an RDA score was then developed by combining various features of the electropherogram to discriminate between those patients who subsequently exhibited pCR and those that did not. This method generates an RDA score that indicates the degree of RNA disruption. A high RDA score is associated with subsequent pCR, while a low RDA score indicates that patients are unlikely to receive long term chemotherapy benefit. For this example, the RDA score was based on the maximum value for the ratio of the area of the intermediate region to the sum or the areas of the 28S and 18S peaks (i.e. intermediate/(28S+18S)).

Figure 7A:
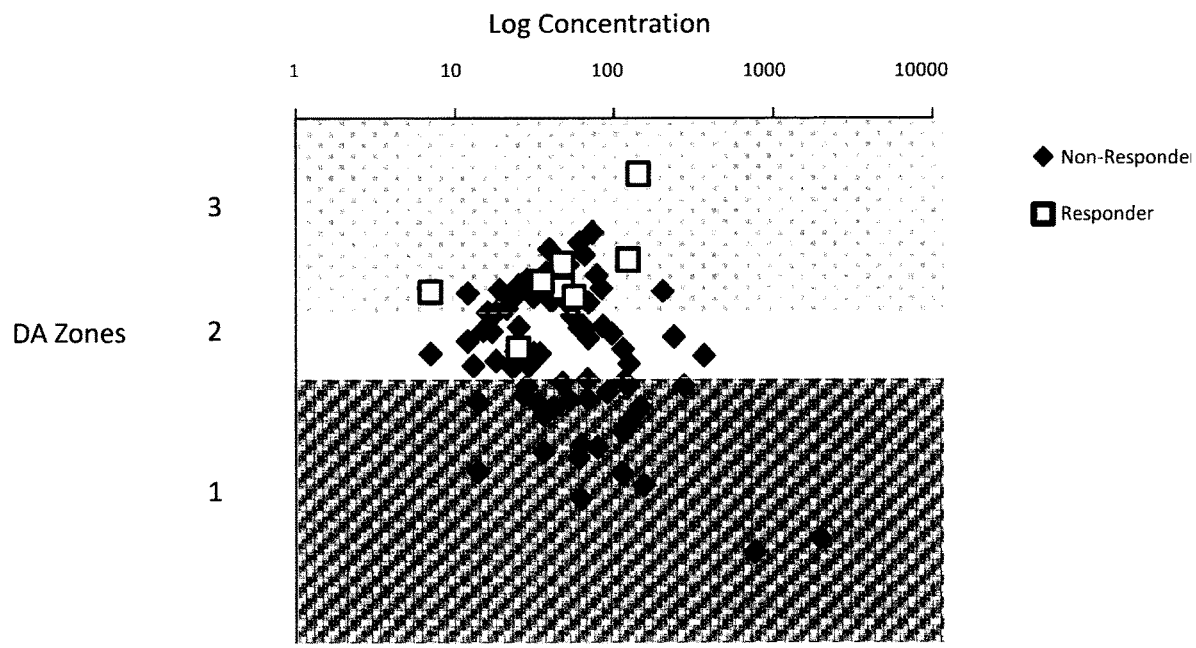
FIG. 7A is a graph of patient distribution in RDA zones.
Figure 7B:
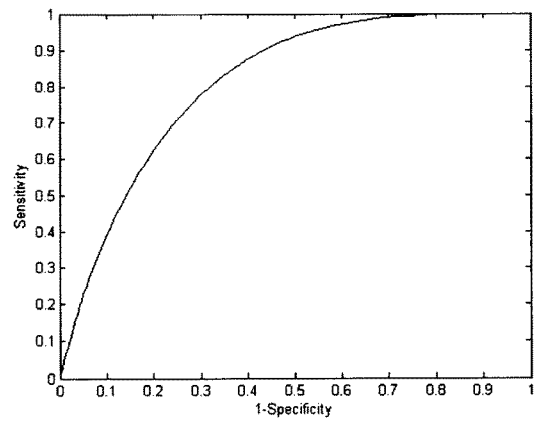
FIG. 7B is an ROC curve corresponding to FIG. 6A.

Results:

When applied to patients in the MA-22 study (partial patient details available in Parissenti et al. 2010 and PCT/CA2008/001561; 35 additional patients have been analyzed for a total of 85 patients and in some cases 3 samples per subject were analyzed; PPV AND NPV numbers described herein are based on the full data set) after the $3^{rd}$ or $4^{th}$ cycle of chemotherapy, the RDA score (e.g. based on the ratio of the Intermediate Area/(28S+18S Areas)) made the following predictions. Of the 85 patients studied, it predicted 32% to be non-responders. This prediction had a negative predictive value of 0.99 with a 95% confidence limit of 0.98-1.0 and a false negative rate of 2%. Of patients achieving pCR, RDA predicted 87% of having an increased chance of responding. This prediction had a positive predictive value of 0.19 reflecting that some patients had a drug effect but did not achieve a pCR. FIG. 7A illustrates the RDA Zones and identified responders and non-responders and FIG. 7B illustrates the ROC curve. The number of responders is also tabulated below in TABLE 3.

For example, selecting a threshold of 10.2 for the RDA score, the negative prediction value for mid treatment responders is 0.99. This means that a tumour sample having an RDA of >10, for example, can be predicted to be non-responsive to the chemotherapy treatment with greater than 99% confidence.

The average standard deviation for samples measured in triplicate and using RDI based on the ratio of Intermediate Area/(28S+18S Areas) was 41. This was for mid-therapy samples and is expected as tumours can be highly heterogeneous.

TABLE 3

MA22 Patient Response

| Clinical Response | Complete Pathologic Response pCR | | RDA |
|---|---|---|---|
| Complete: 17 patients | 6 Patients | 7 Patients | Zone 3 |
| | | | 25 Patients No pCR |
| | | | 7 pCR |
| Partial: 64 Patients | 2 Patients | 1 Patient | Zone 2 |
| | | | 25 Patients No pCR |
| | | | 1 pCR |
| No response: 4 Patients | | | Zone 1 |
| | | | 27 Patients No pCR |

Conclusions:

Use of RDA in clinical practice will enable identification of patients unlikely to respond to breast cancer chemotherapy. Patients with an RDA score that indicates no long term chemotherapy benefit can then avoid the toxic side-effects of chemotherapy and can be switched to an alternate treatment, which may provide a better clinical outcome as well as health care cost savings.

Example 4

The methods and assays described herein can be used for assessing the benefit of changing therapy for non-responders. Changing chemotherapy protocols midstream on the basis of patient response may result in improved overall survival as well as improved disease free survival rates.

Predicting ultimate response rapidly, for example, after one or two cycles of a chemotherapy treatment, could provide useful information for maximizing clinical benefit and/or minimizing toxicity.

To assess this, patients are treated with one or more different chemotherapy drugs. Core biopsies are taken from the patients at one or more times of before, during and/or after treatment. The biopsies are analyzed using an RNA degradation assay. Responders and non-responders predicted based on the RDA assay are identified. Non-responders are randomized into two or more groups. For example, subjects can be maintained on their same treatment or receive adjuvant or other treatment (e.g. e.g. adjuvant, different drug or other therapy such as surgery or radiation). Outcomes for the predicted "non-responder" groups are compared to assess accuracy of prediction and to assess whether altering treatment (e.g. adjuvant, different drug or other therapy such as surgery or radiation) results in improved outcome.

Additional markers can be analyzed pre, mid and/or post treatment.

Example 5

Subjects with ER/PR+/HER2− negative and triple negative tumours are assigned a therapy based on, for example, molecular profiling. For example, an arm could receive neo-adjuvant hormonal treatment and a second arm neo-adjuvant chemotherapy A.

Responders and non-responders are predicted using an RNA disruption assay method. Non-responders can be randomized to receive different or additional treatment. For example, non-responders in the first arm would either continue on the hormonal treatment or receive chemotherapy or hormonal therapy plus an adjuvant therapy; and non-responders in the second arm would either continue to receive chemotherapy A or receive chemotherapy B and/or surgery.

The outcomes such as disease free survival for all patients and also patients switching therapy would be compared to patients continuing therapy.

Example 6

Cells were plated and treated with docetaxel concentrations ranging from 0.001-40 µM for 24 to 72 hours to assess the effect on cell number, RNA content, and integrity (measured using a Bioanalyzer 2100 from Agilent Technologies, Inc.).

A2780 cells were treated for up to 72 hours with docetaxel at 0.005 uM and 0.2 uM. Cell counts were measured at each time-point. Cell numbers remained constant for concentrations of docetaxel greater than or equal to 0.005 uM (FIG. 9A). The use of the asterix (*) in FIGS. 9A and 9B refers to whether the differences between the drug-treated samples and the drug-free control are considered statistically significant (in a two-way ANOVA with Bonferroni post test to determine significance).

A2780 cells treated for up to 72 hours with docetaxel at 0.005 uM and 0.2 uM, were analyzed for the amount of RNA per cell. RNA was isolated and electophoretically separated using an Agilent Bioanalyzer. The amount of RNA per cell was calculated and shown to increase in a time-dependent and dose-dependent manner. The results are shown in FIG. 9B.

A Recovery Assay was next carried out to determine if A2780 cells could recover from treatment with 0.2 uM docetaxel. A2780 cells were treated with 0.2 uM docetaxel for up to 72 hours and then washed and replated in drug-free media. No resumption of cell proliferation was seen under these conditions (FIG. 9C).

Electrophoretic separation of A2780 cell RNA from cells treated with docetaxel for 24 hours at concentrations ranging from 0 to 40 uM, demonstrate the appearance of bands in the intermediate region and the low banding region. RNA was isolated and electrophoretically separated on an Agilent Bioanalyzer. As shown in FIG. 9D bands appeared just below the 28S (e.g. intermediate) and 18S bands (e.g. low banding region) at 0.005 uM and peaked at 0.2 uM.

Traces of the electropherograms also illustrate that the banding which appears just below the 28S and 18S peaks at a concentration of 0.005 uM and peaks at a concentration of 0.2 uM (FIG. 9E).

It should be noted that the RDI values shown in FIGS. 9F and 9G were determined using the methods 200 and 300 although method 400 could be used instead of method 300.

Analysis using RDA was performed. FIG. 9F is a plot of the measure of Intermediate/(28S+18S) for A2780 cells treated with docetaxel concentrations of 0.005 uM and 0.2 uM for 24 to 72 hours. Each value represents a single sample. Two replicate experiments had similar results. The graph demonstrates that the ratio of the Intermediate/(28S+18S) increases dramatically with time. Similarly, a graph of the ratio of Low banding area/(28S+18S) demonstrates this ratio also increases with time (FIG. 9G). As before each value represents a single sample. Two replicate experiments had similar results.

A time course experiment was conducted in A2780 cells. Cells were treated for up to 72 hours with docetaxel at 0.005 uM and 0.2 uM. RNA was isolated and run on an Agilent Bioanalyzer. FIG. 9H demonstrates that banding appears below the 28S and 18S bands at all time-points.

A docetaxel A2780 resistant cell line was made as described in Li et al., Int. J. Mol. Med 2004 14(20): 257-264.

A time course experiment was conducted. Sensitive parental and docetaxel resistant A2780 cells were treated with docetaxel for 24 hours. RNA was isolated and run on an Agilent Bioanalyzer.

As shown in FIG. 9I, banding appears below the 28S and 18S bands at 0.005 uM in sensitive cells. However, no banding is evident in resistant cells.

The effect of a caspase inhibitor on RNA integrity changes was next assessed. Cells were treated with or without docetaxel at a concentration of 0.2 uM in the presence or absence of the caspase inhibitor Q-DEVD-OPH (Biovision Laboratories) at a concentration of 10 uM.

Figure 9J:
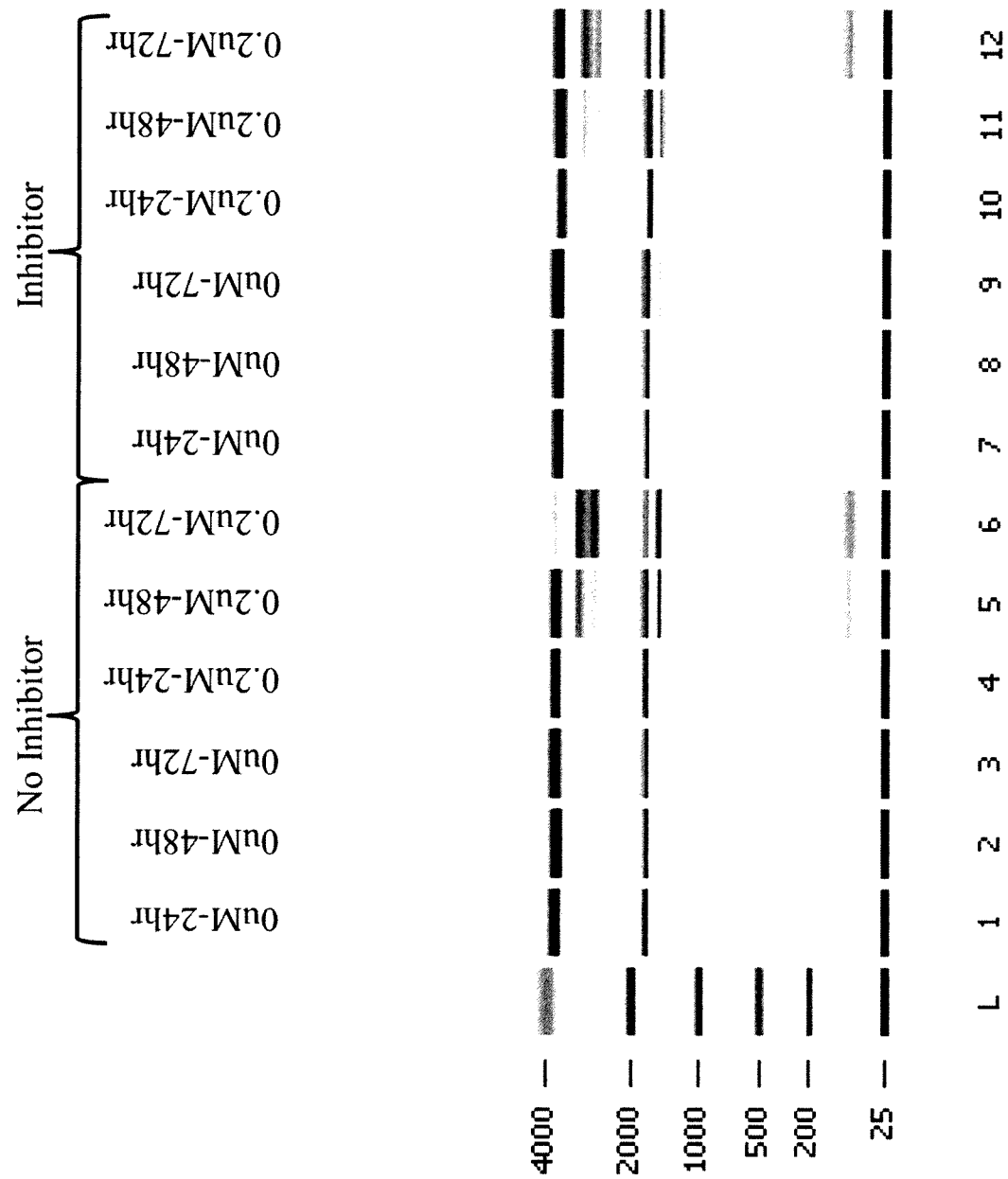
FIG. 9J is an image of a gel of electrophoretically separated A2780 ovarian cancer cell RNA samples treated with different concentrations of docetaxel for different time periods in the presence or absence of caspase inhibitor.

RNA was isolated and run on an Agilent Bioanalyzer and the banding pattern is shown in FIG. 9J. The inhibitor reduces the loss of 28S and 18S bands at 72 hr. Bands below the 28S and 18S bands are detectable in the presence and absence of the caspase inhibitor.

Although cell number remained constant for concentrations ≥0.005 uM docetaxel, withdrawal of the drug did not result in resumption of cell proliferation. RNA content increased per cell ($p<0.05$) while RIN did not change significantly in this range. However, novel discrete bands appeared in the rRNA banding pattern at 0.005 μM, peaking at 0.2 μM docetaxel, just below the 28 s and 18 s rRNA bands. In contrast, docetaxel-resistant A2780DXL cells did not display similar changes upon treatment, indicating that changes in tumor cell RNA content and integrity could be used to monitor response to chemotherapy agents.

Example 7

A2780 ovarian cancer cells were treated with radiation of 2 to 10 Gray using a Gulmay RS320 Irradiation System and subsequently harvested after 24, 48 and 72 hr. RNA was isolated and run on an Agilent Bioanalyzer. Analysis of the electropherogram demonstrated that an increase in the ratio Intermediate Area/(28S+18S Areas) at 72 hours is detectable in radiation treated cells (FIG. 10A). For example, cells treated at 10 Gray for 72 hours show RNA disruption in the intermediate region and the low banding region, but not much difference in the area of the electropherogram where the autolysis peak resides. FIG. 10B shows A2780 cells treated with 5 Gy for 24 hrs (lane A), 5 Gy for 48 hrs (lane B), 5 Gy for 72 hrs (lane C), 10 Gy for 24 hrs (lane D), 10 Gy for 48 hrs (lane E) and 10 Gy for 72 hrs (lane F). RNA disruption is evident at 72 hrs at both dose levels.

Example 8

Methods

Administration of the FEC-D Regimen with Concurrent Radiation

Thirty two patients with stage III non-metastatic, non-inflammatory locally advanced breast cancer were treated with neoadjuvant 5-Fluoro-uracil, Epirubicin, and Cyclophosphamide (FEC also referred to as CEF) q3 weekly for 4 cycles followed by weekly Docetaxel (35 mg/m²) concurrently with regional radiation (45 Gy with 16 Gy boost in 25 & 5 fractions) for 6 weeks followed by an additional 3 weeks of docetaxel chemotherapy without radiation. This was followed by a modified radical mastectomy. Patient and tumour characteristics were recorded at baseline and following treatment and clinical response and treatment-related toxicities noted. Image guided serial 14 gauge tumour core biopsies were taken from the patients pre-, mid- and post-treatment, and 1 mm³ sections were immediately taken from the biopsies, immersed in RNAlater™, and stored frozen. MID treatment is after FEC but before docetaxel with concurrent radiation therapy.

Isolation of RNA from Tumour Core Biopsies

RNA was isolated from image-guided tumour core biopsies of patients pre-, mid-, and post-treatment using Qiagen miRNeasy® Mini kits, following a modification of the protocol published on the manufacturer's website, http://www1.qiagen.com/literature/handbooks/literature.aspx?id=1000291. Biopsies were cut into several sections for various assays, with the section used for RNA integrity analysis placed in RNAlater. The biopsies in RNAlater were immediately dropped in 0.5 ml of RLT buffer containing β-ME (10 μl into 1 ml) in a 1.5 ml tube. The biopsies in RLT buffer were homogenized with a Coreless motor homogenizer for 5 min (from the Kontes Glass Company). The lysate was then passaged at least 5 times through a 20-gauge needle (0.9 mm diameter) fitted to an RNase-free syringe. The sample was then centrifuged at high speed in a refrigerated microfuge at 4° C. for 3 minutes, with transfer of the supernatant to a new tube. One volume (500 μl) of 70% ethanol was then added to the supernatant and the sample was mixed well by repeated pipetting. If some lysate was lost during homogenization, then the volume of ethanol was adjusted accordingly. Visible precipitates formed after the addition of ethanol in some samples did not affect the RNA isolation procedure. A maximum of 700 μl of the sample, including any precipitate, was added to a Qiagen® mini column and placed in a 2 ml collection tube. The column was centrifuged for 15 s at ≥8000×g (210,000 rpm) and the flow-through discarded. The remainder of the sample was then added to the column and the column centrifuged again. From this point forward, the column was then washed twice in RPE buffer and dried by centrifugation as per the manufacturer's protocol. The RNA was then eluted from the column in 30 μl of RNase-free water and the elute reapplied and eluted from the column to increase the yield and concentration of the RNA obtained.

Assessment of RNA Quality Using an Agilent 2100 Bioanalyzer

The above RNA samples were applied to RNA 6000 Nano Lapchips™ (purchased from Agilent Biotechnologies, Inc.) and subjected to capillary electrophoresis using an Agilent® 2100 Bioanalyzer.

Further details of the study and clinical results are provided Cancer Res 2012; 72(24 Suppl): Abstract nr P1-14-13.

Results

RNA isolated from patient tumour samples after radiation was run on an Agilent Bioanalyzer. Analysis of the electropherogram demonstrated an increase in the ratio Intermediate Area/(28S+18S Areas) in two patients that had a pathological complete response (FIG. 11a).

Analysis of the electropherogram also demonstrated an increase in the ratio Low Area/(28S+18S Areas) in two patients that had a pathological complete response (FIG. 11b).

Example 9

Another method can be used for peak identification and generally comprises determining a standard sample (i.e. a normal sample) for a plurality of samples, for example such as the samples provided on a platform such as an RNA chip and the 28S and 18S peaks, as well as other features of interest, are identified as the retention times for each sample to the standard sample. For example, when the standard sample is determined the method then generally comprises determining which samples require adjustment (e.g. forming an adjustment group), determining the standard retention time for the platform, adjusting samples in the adjusting group based on the standard retention time, determining peaks using the standard retention time and calculating one or more features of the peaks and nearby regions (as shown by the examples given in the discussion of FIG. 5A). By identifying a "standard" or "normal" sample for each platform, (for example, when multiple test samples are run simultaneously, as in the case of when an Agilent Bioanalyser chip platform can run 12 samples per chip, for example), the 28S and 18S peaks can more readily be determined by comparing the retention times of each sample to those of the "standard" sample of the chip platform. This then allows for a normalization for the samples that are collected at the same time using the same means. Further details on this method are provided in Example 10 and FIG. 12A which provides a flowchart of an example embodiment to implement the aforementioned method of peak identification and feature calculation.

Figure 12B:
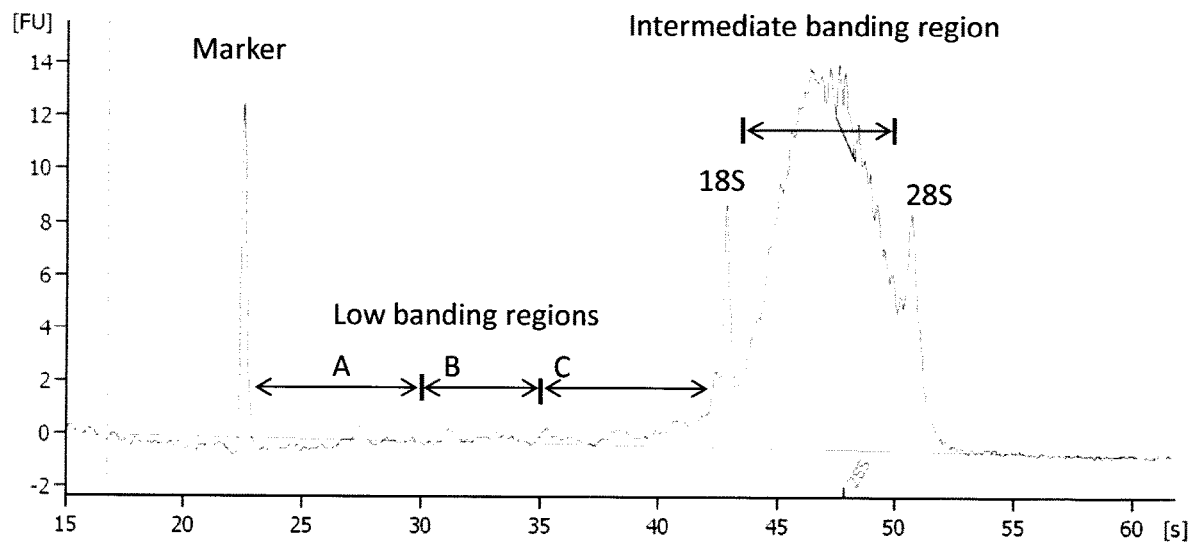
FIG. 12B is a graph of an example electropherogram in which the 18S peak, the 28S peak, the intermediate banding region, the low C banding region, the low B banding region, the low A banding region and the marker region are defined.

Additional features have also been identified as can be seen in FIG. 12B in which the low banding region is trisected into several regions including the low A banding region, the low B banding region and the low C banding region.

Example 10

Modified Method Using the Agilent Bioanalyzer

Referring now to FIG. 12A, shown therein is an example of an alternative embodiment of a method 400 for determining peaks and calculating features for electropherogram datasets. The method 400 generally involves identifying a standard sample or normal sample for a plurality of electropherogram datasets obtained from samples on a common analysis platform, such as an RNA chip for example, and then using the standard sample to adjust the location of peaks for the electropherograms for the samples that are determined to require adjustment and are therefore contained within an adjustment group. The plurality of electropherogram datasets are generated using samples that are analyzed using the same platform such as an RNA chip, for example. It has been found that the peak retention times are different for different RNA chips (e.g. different platforms). It has been found that the method 400 allows for the more accurate assessment of the 18S peak and the 28S peak in samples that are highly fragmented.

At 402, the method 400 determines a range for the peaks of interest. This range may be initialized to a default setting and then shifted if required. For example, for the 18S and 28S peaks, the default ranges can be initially set to [39.5 s, 44.95 s] and [45.05 s, 53.5 s]. On a scale of 0 to 100, the range for the 18S region is [45.85, 61.25], and that for the 28S region is [61.6, 85.75]. These ranges can then be shifted under certain conditions, such as, but not limited to the case when the marker region is not at its expected location. For example, these ranges may be shifted if the time of the marker, which is the time associated with the first peak that is a dye-only peak meaning that it does not contain any RNA but rather indicates the start of the run for the gel, is not at about 22.5 seconds. For these samples, a shift factor is calculated according to equation 1:

$$rngshft = \text{marker time} - 22.5 \quad (1)$$

where marker time is the start time of the marker. The range for the 18S region is then shifted up according to [39.5+ rngshft×1.5, 44.95+rngshft×1.5] and the range of the for the 28S region is shifted up according to [45.05+rngshft×2.5, 53.5+rngshft×2.5].

Figure 12C:
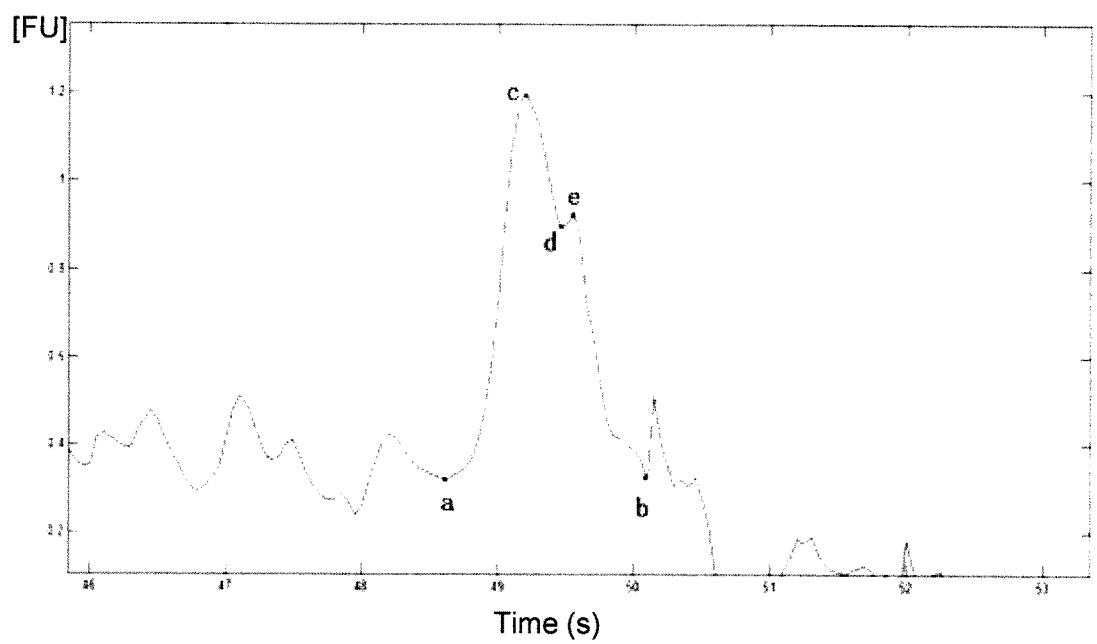
FIG. 12C is a graph showing how a peak is determined using the method of FIG. 12A.

Referring now to FIG. 12C, shown therein is a graph of an example peak which is now used to illustrate some aspects of how peaks are defined using method 400. FIG. 12C shows a plot of a general peak with one sub-peak with the x-axis being time in seconds and the y axis being is the value [FU].

It should be noted that a real-valued function f defined as a non-linear line is said to have a local (i.e. a relative) maximum point at the time point x*, if there exists some ε>0 such that f(x*)≥f(x) when |x−x*|<ε. The value of the local maximum point does not have to be larger than the value of all the other points but rather it just needs to be the largest value within a local range. The function f has a global (i.e. absolute) maximum point at x*, if f(x*)≥f(x) for all x. A global maximum point must have the largest value. A function can have more than one local maximum point, but only one global maximum point. In a similar way, there is also a local minimum point and a global minimum point.

The whole peak region is defined from time a to time b. The time point a is the starting point of the peak and the time point b is the ending point. The global minimum point in the range [a, b] is either a or b. The peak point is defined as the global maximum point, i.e. c. The peak height is defined as the value of the highest point, i.e. the value of c. The peak width is defined as (ending time−starting time), i.e. b−a. The peak area is defined as the area above the x-axis and under the curve from time point x=a to x=b. The local maximum point e is a sub-peak point. The 18S and 28S peaks can have more than one sub-peak. The local minimum point d is the sub-peak low.

At 404, the peaks are located by first searching for all possible peak candidates in the two identifying ranges. This involves searching for local maximums surrounded by local minima on either side. Each part of the electropherogram within the range which has these criteria is designated as a "peak candidate". The height difference of each possible peak candidate is then calculated. The height difference of a peak candidate is defined as the difference of the highest peak value and the average lowest peak values. The lowest peak values that are averaged are the starting point and ending point of the peak at the starting time and the ending time for each peak and any sub-peak low values (i.e. local minima) are not included. The two peak candidates with the largest height differences can be chosen as the 18S and 28S. The 18S peak or the 28S peak may have the higher value. Once the 18S peak and the 28S peak are correctly identified, the desired features can then be calculated such as, but not limited to, the width, the height and the area of the 18S and 28S peaks, the intermediate area, the low C banding region area, etc. The sub peak is included in the area calculation or the width calculation and it has no impact on the height (because it is always smaller). The values for these features can be calculated now since they will not change for some of the samples. In an alternative embodiment, the values for these features may be calculated for all samples after the samples requiring adjusting have been adjusted.

It should be noted that with method 400, there are two cases when the peak is allowed to have more than one maximum value. First, if the width of a peak is less than 0.15 seconds, this peak is considered as a sub-peak of its adjacent peak. Secondly, if the difference between the starting value and the ending value of a peak is too large, this peak is considered as a sub-peak of its adjacent peak. The difference is considered to be too large when the height of the sub-peak (i.e. the value at time point e minus the value at time point b in FIG. 12C) divided by the difference between the local maximum and local minimum (i.e. the value at time point e minus the value at time point d in FIG. 12C) is larger than a threshold value, such as, but not limited to, 5, for example, then it is too large. In general it has been found that one or two peaks may be associated with the 18S peak and the 28S peak using method 400.

Furthermore, in method 400, there is no restriction based on the width of the 18S peak and the 28S peak when determining the 18S peak and the 28S peak locations. Also, in method 400, there is no restriction based on the distance between the 18S peak and the 28S peak when determining the 18S peak and the 28S peak locations.

At 406, the standard sample for the plurality of samples is determined. The standard sample may be defined to be the sample having the smallest standard score in the plurality of samples wherein the standard score is defined equation 2.

$$\text{standard score} = \frac{\text{intermediate area} + \text{lower } b \text{ area} + \text{lower } c \text{ area}}{18S \text{ peak area} + 28S \text{ peak area}} \quad (2)$$

At 408, the retention time of the standard sample is compared with the retention time of the other samples. The retention time is examined for both the 28S and 18S peaks. Those samples whose retention time is not around the retention time of the standard sample will be assigned to an adjustment group, and the rest of the samples will be assigned to a standard group. A threshold value can be used to assess this (i.e. the retention time not "being around") such as, but not limited to, 0.5 seconds. Accordingly, if the difference between the retention time of both the 18S peak and the 28S peak for a sample is off by more than 0.5 seconds compared to the same peaks of the standard sample, then the sample is put into the adjustment group and requires adjusting.

At 410, the standard retention time for the 18S peak and the 28S peak is chosen based on the samples in the standard group. For example, the standard retention time may be chosen as the median of the retention time of the samples in the standard group. In alternative embodiments, other statistical measures may be used such as, but not limited to, the mean or some variations on the mean.

At 412, the 18S and 28S peaks for each sample in the adjustment group are determined by locating the peaks that are around the standard retention times determined in act 410 (i.e. the times of the 18S and 28S peaks determined from the standard samples). For example, using the samples that are in the standard group, and hence represent the most intact RNA, the median value of the retention time for the 28S and the 18S is identified. Each sample in the adjustment group is then examined to find the peaks that appear at that retention time. However, the actual retention time of the 28S and 18S peaks may not be identical to the those of the standard sample as the peak may not have its highest point at the same exact retention time. In this case if the peak area still includes the "standard retention time", this peak is designated as the 18S peak or the 28S peak even though the maximum value of the peak does not occur exactly at the same retention time. All measurements (width, height, area) are then taken based on this peak. Other regions of interest can also be determined once the 18S and 28S peaks are located such as, but not limited to, the low C banding region and the intermediate region, for example.

At 414, the features of interest that are used in determining the RDA score or RDI are then calculated for all of the samples.

An RDI score may be calculated for each sample on the RNA chip including the "control" sample, which may be defined as the sample on the RNA chip that is the closest to "intact RNA".

In one embodiment, the combination of features is a ratio of the low C banding region area to the sum of the 18S peak area and the 28S peak area, which can be represented by the expression "low C/(18S+28S)". Method 300 can also be used with this combination of features.

It should be noted that the method 400 can also operate if there are two samples on the RNA chip in which one of the samples is a positive control sample of intact RNA, which in fact is run on every chip, and the other sample can be the sample for which an RDA or an RDI value is obtained. Alternatively, the second sample may also be an analyzing sample which may be useful under certain circumstances.

Accordingly, at least one embodiment described herein comprises obtaining two electropherogram datasets corresponding to a test sample and a control sample, the test sample being a unique biological sample comprising cellular RNA optionally at a time point before, during or after the treatment requiring analysis and the control sample being another unique biological sample or a positive control sample of intact RNA or approximately intact RNA; placing the electropherogram of the test sample into an adjustment group and placing the electropherogram of the control sample into a standard group; identifying normal characteristics representative of a normal sample from the standard group; determining locations of peaks for the electropherogram in the adjustment group and adjusting the location of the peaks based on the normal characteristics; and determining values for features from the adjusted electropherogram and optionally the electropherogram from the standard group when the control sample is another unique biological sample requiring analysis.

Example 11

The Boundaries of the Low A, Low B, and Low C Banding Regions

The boundaries were set based on the location of discrete sets of peaks within the Low region, which is the region between the marker region and the 18S region (i.e. 18S band). The Low A banding region may be defined as the range between the marker region and 30.0 s. The Low B banding region may be defined as the range between 30.0 s and 35.0 s. The Low C banding region may be defined as the range between 35.0 s and the 18S region.

Linear Discriminant Analysis was used to identify features that are most predictive in the MA22 data set. Combinations of two or three features were found to improve prediction performance and many combinations listed in TABLES 7 to 8 were very close in their ability to predict responders. All peak measurements, area measurements, and width measurements for various features (i.e. 28S, 18S, intermediate, Low C) used in this analysis were normalized to the entire area. The entire area is defined to be the sum of the areas of the low banding region, the 18S region, the intermediate region and the 28S region which represents the total amount of RNA present in the analyzed sample.

Example 12

The methods 200 and 400 of were used to assess the MA22 trial dataset in a similar fashion as for the use of methods 200 and 300 in Example 2. RNA isolated from mid-therapy tumour samples was analyzed using an Agilent Bioanalyzer. The result was that the misidentification of the 28S peak in the chemotherapy treated samples fell to 0.3% using the method 400 (see TABLE 4).

TABLE 4

Error Rates and Types in MA22 Dataset

| Reason | Rate |
|---|---|
| Inadequate Sample | 9.6% of samples |
| Aberrant Run - baseline or marker issue | 1.9% of samples |
| Mis-identification of 28S and 18S peak | 0.3% of samples |

Figure 13:
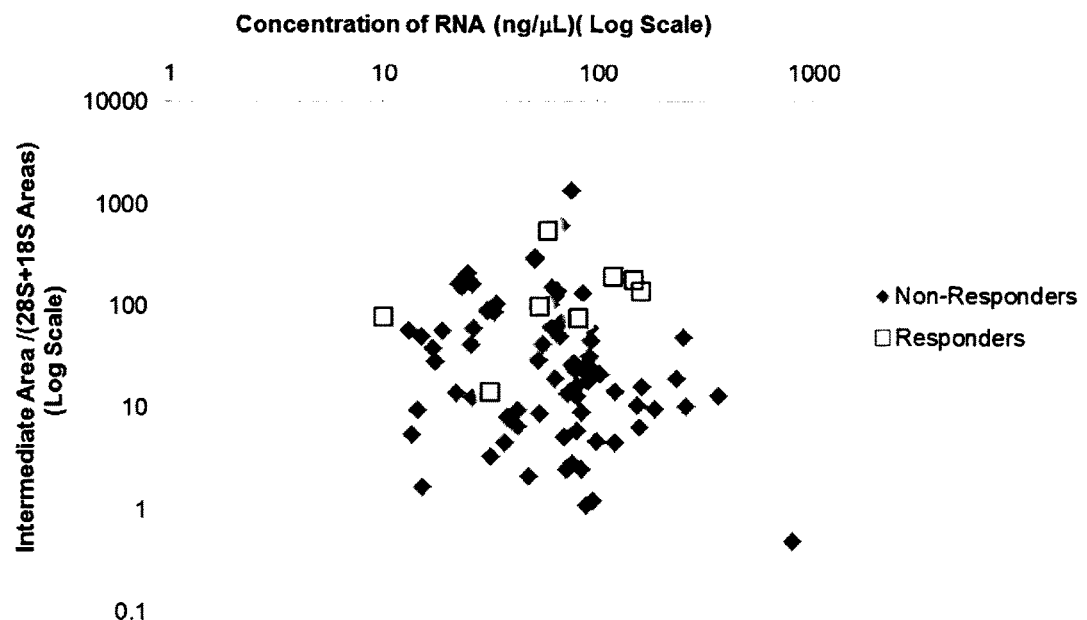
FIG. 13 is a log-log graph of the feature of log (Intermediate/(28S+18S)) versus log RNA concentration for a sample study using the modified peak identification method.
Figure 14A:
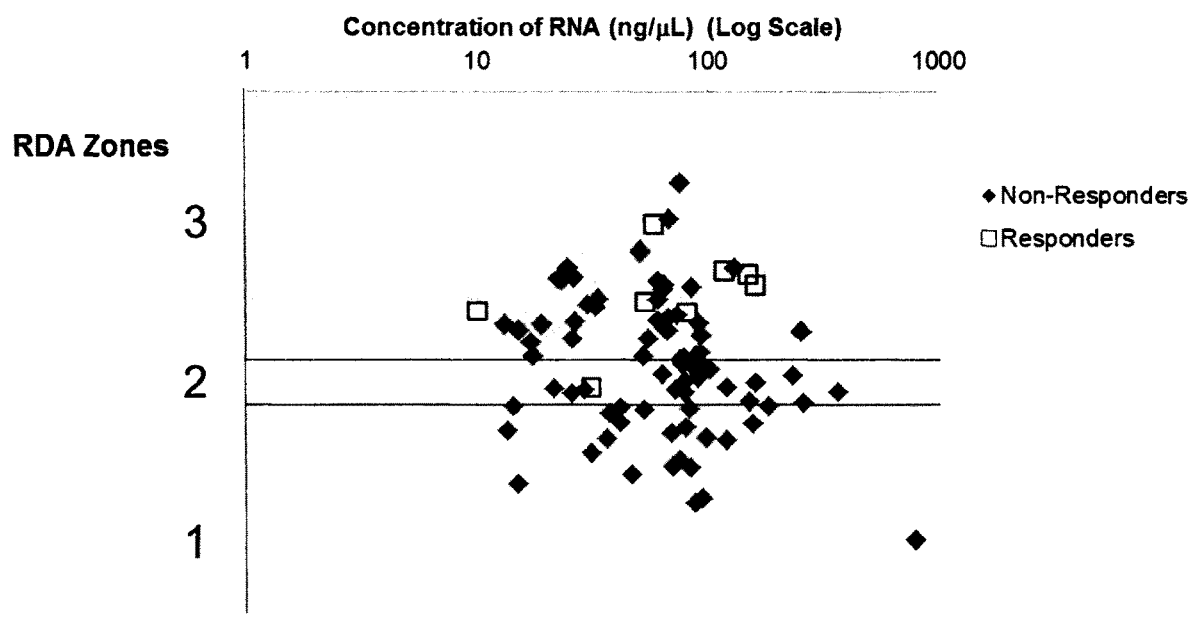
FIG. 14A is a graph of patient distribution in RDA zones using the modified peak identification method.
Figure 14B:
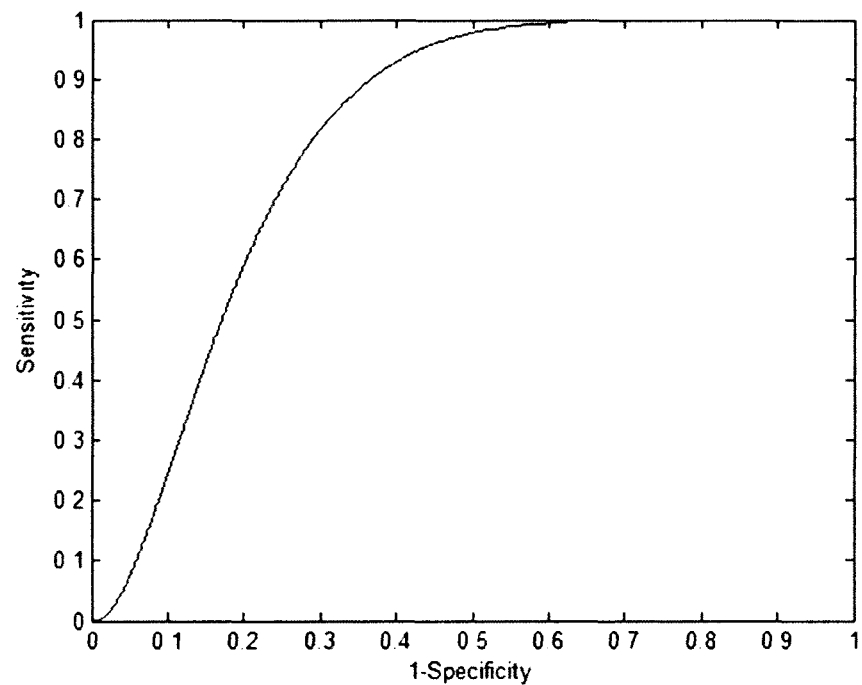
FIG. 14B is an ROC curve corresponding to FIG. 14A.

The ratio of the intermediate area to the sum of the 28S and 18S areas was generated for mid-therapy tumour samples and plotted versus concentration on a log-log graph. In particular, the maximum ratio value for each patient was graphed (FIG. 13). RDA zones were established based on clinical criteria. In this example, the clinical criteria was a negative predictive value for the threshold value between zone 1 and 2 at 0.98 or 0.99. For zones 2 and 3, the clinical criteria were chosen to be the best PPV value possible while including most of the responders in zone 3. The maximum RDA for each patient was graphed vs. log concentration on a semi-log chart and is shown in FIG. 14A for the various RDA zones. FIG. 14B shows the Receiver Operating Characteristic (Sensitivity vs. 1-Specificity) curve for Maximum value of the ratio of the Intermediate area/(18S+2S). The Area under the curve (AUC) was about 0.8.

Figure 14C:
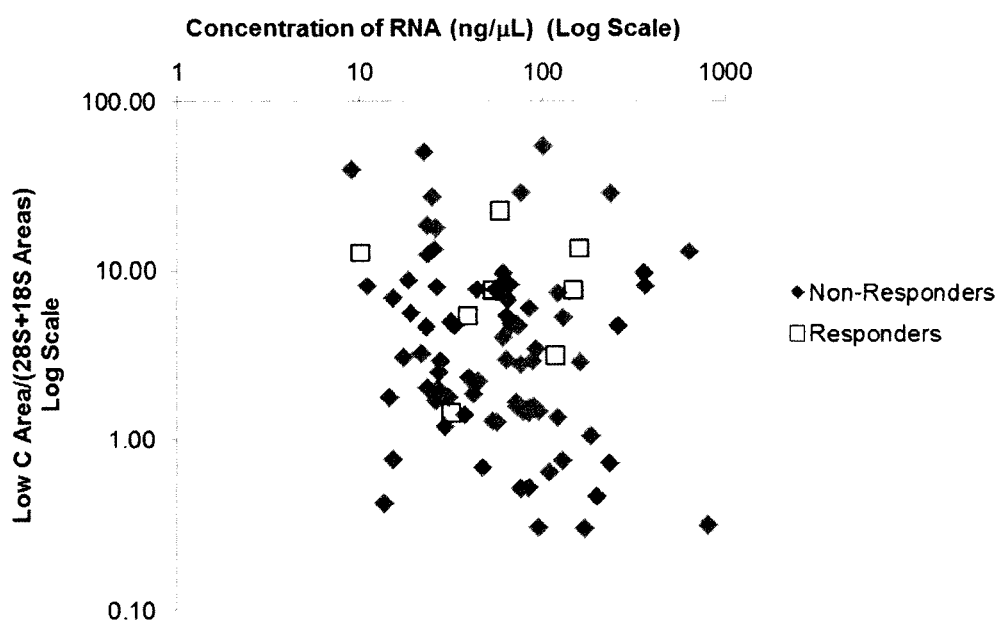
FIG. 14C is a log-log graph of the feature of log (low C/(28S+18S)) versus log RNA concentration for a sample study using the modified peak identification method.

A ratio of the Low C banding region area to the sum of the 28S and 18S areas was also generated. The maximum value for this ratio for each patient was plotted vs. RNA sample concentration (for the sample that had the maximum ratio) on a log-log plot and is shown in FIG. 14C.

Figure 14D:
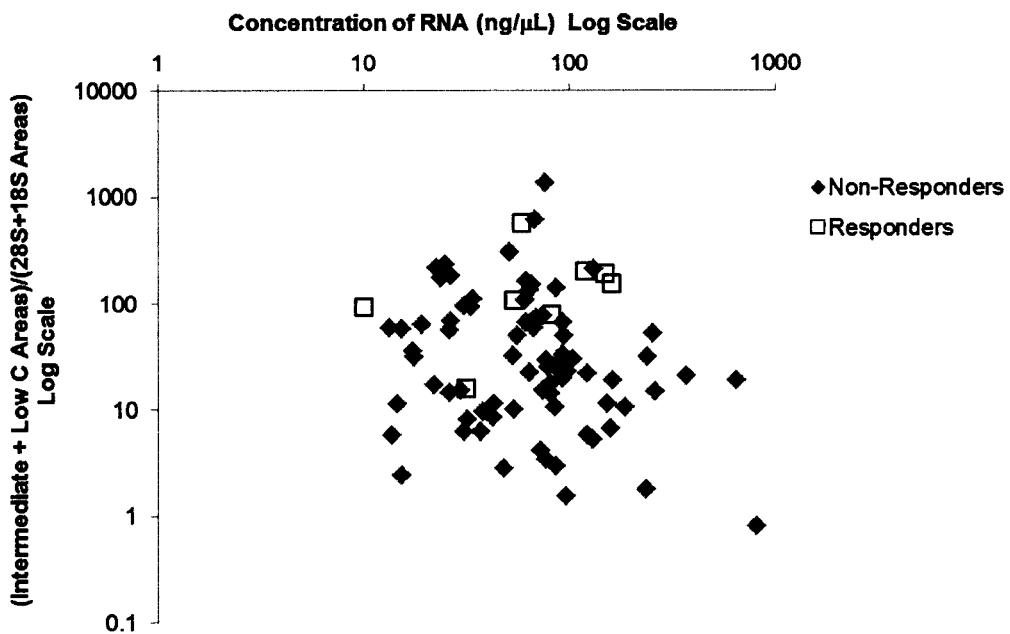
FIG. 14D is a log-log graph of the feature of log (Intermediate+low C)/(28S+18S) versus log RNA concentration for a sample study using the modified peak identification method.

A ratio of the sum of the intermediate area and the Low C banding region area to the sum of the 28S and 18S areas was also generated. The maximum value for this ratio for each patient was plotted vs. RNA sample concentration (for the sample that had the maximum ratio) and is shown in FIG. 14D.

Other ratios were also calculated and then Linear Discriminant Analysis (LDA) was used to identify the features that were most predictive for the MA22 data set. The details for the application of the LDA are discussed in Example 13 below. In general, combinations of two or three features were found to provide superior prediction performance but most of the combinations listed in TABLES 8 and 9 below were found to be close in their ability to predict responders vs. non-responders.

TABLE 5 identifies features associated with RNA disruption by Chemotherapy determined while using method 400.

TABLE 5

Features Associated with rRNA Disruption by Chemotherapy identified using Linear Discriminant analysis

| Feature | Effect |
|---|---|
| 28S peak | Loss of area, peak height, peak width |
| 18S peak | Loss of area, peak height, peak width |
| Intermediate region | Area, discrete banding |
| Low C region | Area, discrete banding |
| Concentration | Decrease |
| Ratio of 28S to 18S | Increase or decrease |

When the methods 100 and 400 were applied to patients in the MA-22 study (patient details available in Parissenti et al. 2010 and PCT patent application No. PCT/CA2008/001561) after the $3^{rd}$ or $4^{th}$ cycle of chemotherapy, the RDA score was used to predict that, out of the 85 patients that were studied, 27% were non-responders. This prediction had a negative predictive value of 0.99 with a 95% confidence limit of 0.95-1.0. Of patients achieving pCR, the RDA score predicted 87% of these patients as having an increased chance of responding. This prediction had a positive predictive value of 0.22 reflecting that some patients had a drug effect but did not achieve a pCR. FIG. 14A illustrates the RDA Zones and identified responders and non-responders and FIG. 14B illustrates the ROC curve. The number of responders is also tabulated below in TABLE 6.

TABLE 6

MA22 Patient Response

| Clinical Response | Complete Pathologic Response pCR | RDA |
|---|---|---|
| Complete: 17 patients | 6 patients | 7 patients Zone 3 |
|  |  | 38 patients |
|  |  | 31 No pCR |
|  |  | 7 pCR |
| Partial: 64 patients | 2 patients | 1 patient Zone 2 |
|  |  | 24 patients |
|  |  | 23 No pCR |
|  |  | 1 pCR |
| No response: 4 patients |  | Zone 1 |
|  |  | 23 patients |
|  |  | No pCR |

Example 13

The Area Under Curve (AUC) is an important measure of accuracy for a detection or prediction technique as is known to those skilled in the art. Accordingly, the AUC was used to determine which features and which combinations of features are useful for predicting responders or non-responders to a particular treatment based on samples taken at a certain time point in the treatment regimen. For example, such samples include patient samples that exhibit RNA changes in response to an inducer such as chemotherapy or radiation therapy. Linear Discriminant Analysis was also used (one of the most commonly used classification methods) with different thresholds to assess different features to determine which features or combination of features had the best predictive or discriminative ability. LDA was used when two or three sets of combinations were plotted against one another on two dimensional or three dimensional plots respectively as is shown in TABLES 8 and 9 and this is referred to as two dimensional feature sets and three dimensional feature sets respectively.

TABLE 7 provides the AUC values when a one dimensional feature set comprising single features was assessed on the MA22 dataset using the methods 100 and 400. In this case, the values for the various one dimensional single features were calculated and compared to various threshold values to discriminate between responders and non-responders (i.e. the threshold values were scalar values).

TABLE 7

AUC for one dimensional feature set analysis on the MA22 dataset

| Features | AUC |
|---|---|
| 18S peak area | 0.7706 |
| 28S peak area | 0.7500 |
| 18S peak height | 0.7184 |
| 28S peak height | 0.7848 |
| 18S peak width | 0.4509 |
| 28S peak width | 0.6266 |
| Intermediate region area | 0.7041 |
| Low C banding region area | 0.7041 |
| Low B banding region area | 0.6978 |
| Concentration | 0.5316 |

When a one dimensional feature set, in which only a single feature is used, is used to discriminate between responders and non-responders, the 18S peak area, the 28S peak area and the 28S peak height were found to have the best performance; while the features of 18S peak height, intermediate area, low C area and low B area had the second best performance. However, the features of 18S peak width, 28S peak width and concentration may also carry some useful prediction information.

Accordingly, in one embodiment, the single feature may be the 18S peak area in the 18S region. This can be represented by the expressions "18S" or "18S peak area".

In one embodiment, the single feature may be the 28S peak area in the 28S region. This can be represented by the expressions "28S" or "28S peak area".

In one embodiment, the single feature may be the 18S peak height in the 18S region. This can be represented by the expression "18S peak height".

In one embodiment, the single feature may be the 28S peak height in the 28S region. This can be represented by the expression "28S peak height".

In one embodiment, the single feature may be intermediate area. This can be represented by the expressions "Intermediate" or "Intermediate area".

In one embodiment, the single feature may be low C banding region area.

This can be represented by the expression "low C area" or "low C".

In one embodiment, the single feature may be low B banding region area. This can be represented by the expression "low B area" or "low B".

TABLE 8 provides the AUC values when two dimensional feature sets, comprising at least one feature in each feature set, was assessed on the MA22 dataset using the methods 100 and 400. In this case, the values for the various two dimensional feature sets were calculated and compared to various two dimensional threshold zones to discriminate between responders and non-responders (i.e. the threshold zones are defined by lines).

TABLE 8

AUC for two feature analysis on the MA22 dataset

| Combination of Features | AUC |
|---|---|
| 18S peak area vs. 28S peak area | 0.7722 |
| 18S peak height vs. 28S peak height | 0.7769 |
| (18S peak area + 28S peak area) vs. intermediate area | 0.7587 |
| (18S peak area + 28S peak area) vs. low B banding region area | 0.7745 |
| (18S peak area + 28S peak area) vs. low C banding region area | 0.7951 |
| (18S peak area + 28S peak area) vs. (18S peak width + 28S peak width) | 0.7935 |
| (18S peak area + 28S peak area) vs. concentration | 0.7832 |
| (18S peak height + 28S peak height) vs. intermediate area | 0.7508 |
| (18S peak height + 28S peak height) vs. low C banding region area | 0.784 |
| (18S peak height + 28S peak height) vs. (18S peak area + 28S peak area) | 0.7927 |
| (18S peak height + 28S peak height) vs. (18S peak width + 28S peak width) | 0.7698 |
| (18S peak height + 28S peak height) vs. concentration | 0.7714 |

When a two dimensional feature set was used to do the discrimination between responders and non-responders, it was found that the peak areas and peak heights are useful for discrimination. Accordingly, better discrimination results can be obtained when combining them with other features. From TABLE 8, the two dimensional feature sets of (18S peak area+28S peak area) and low C banding region area, (18S peak area+28S peak area) and (18S peak width+28S peak width), and (18S peak height+28S peak height) and (18S peak area+28S peak area) were found to have the best AUC results. Other combinations listed in Table 8 may also be useful.

Accordingly, in one embodiment, the two dimensional feature sets are used in a two dimensional plot using two orthogonal variables representing each feature set to graph an RDA coordinate that is used to discriminate responders from non-responders. One of the variables is defined by a first feature set and the other variable is defined by a second feature set. These variables may be combined using LDA or QDA as will be described with respect to FIGS. 15A-15D. The first variable comprises the 18S peak area and the second variable comprises the 28S peak area. This can be represented by the expression "18S area vs. 28S area" or "18S vs. 28S".

In another embodiment, the first variable comprises the 18S peak height and the second variable comprises the 28S peak height. This can be represented by the expression "18S peak height vs. 28S peak height".

In another alternative embodiment, the first variable comprises the sum of the 28S peak area and the 18S peak area and the second variable comprises the low C banding region area. This can be represented by the expression "(28S+18S) vs. low C".

In another alternative embodiment, the first variable comprises the sum of the 28S peak area and the 18S peak area and the second variable comprises the low B banding region area. This can be represented by the expression "(28S+18S) vs. low B".

In another alternative embodiment, the first variable comprises the sum of the 18S peak area and the 28S peak area and the second variable comprises the sum of the 18S and 28S peak widths. This can be represented by the expression "(18S+28S) vs. (18S peak width+28S peak width)".

In another alternative embodiment, the first variable comprises the sum of the 28S and 18S peak heights and the second variable comprises the sum of the 28S peak area and the 18S peak area. This can be represented by the expression "(28S peak height+18S peak height) vs. (28S+18S)".

In another alternative embodiment, first variable comprises the sum of the 18S peak area and the 28S peak area and the second variable comprises the intermediate area. This can be represented by the expression "(18S+28S) vs. (intermediate)".

In another embodiment, the first variable comprises the sum of the 18S peak area and the 28S peak area and the second variable comprises the RNA concentration of the sample. This can be represented by the expression "(18S+28S) vs. (concentration)".

In another embodiment, the first variable comprises the sum of the 18S peak height and the 28S peak height and the second variable comprises the RNA concentration of the sample. This can be represented by the expression "(18S peak height+28S peak height) vs. (concentration)".

It should be noted that concentration may be used as a feature in two-feature analysis as it has been found to show good discriminative ability when combined with some other features. The concentration is the RNA concentration in the sample which may be determined using various techniques. For example, in embodiments where the electropherogram is produced by a system like the Bioagilent system, the RNA concentration can be determined using measurements obtainable from the electropherogram. In an example, RNA concentration may be determined by comparing to a known quantity of a known standard such as the marker or ladder. For example the amount of the RNA in a standard or ladder band is divided by the area under the curve for the entire marker. The Total Area of each sample may then be multiplied by this value to give a RNA concentration for each sample.

In another embodiment, the first variable comprises the sum of the 18S and 28S peak heights and the second variable comprises the intermediate area. This can be represented by the expression "(18S peak height+28S peak height) vs. (intermediate)".

In another embodiment, the first variable comprises the sum of the 18S and 28S peak heights and the second variable comprises the low C banding region area. This can be represented by the expression "(18S peak height+28S peak height) vs. low C".

In another embodiment, the first variable comprises the sum of the 18S and 28S peak widths and the second variable comprises the sum of 18S peak area and the 28S peak area, which can be represented by the expression "(18S peak width+28S peak width) vs. (18S+28S)".

TABLE 9 provides the AUC values when three dimensional features sets, comprising at least one feature in each feature set, was assessed on the MA22 dataset using the methods 100 and 400. In this case, the values for the various three dimensional feature sets were calculated and compared to various three dimensional threshold zones to discriminate between responders and non-responders (i.e. the threshold zones were defined by planes).

TABLE 9

AUC for three feature analysis on the MA22 dataset

| Combinations of Features | AUC |
| --- | --- |
| (18S peak area + 28S peak area) vs. (18S peak height + 28S peak height) vs. low C banding region area | 0.7864 |
| (18S peak area + 28S peak area) vs. (18S peak height + 28S peak height) vs. (18S peak width + 28S peak width) | 0.7761 |
| (18S peak area + 28S peak area) vs. (18S peak height + 28S peak height) vs. intermediate area | 0.7445 |
| (18S peak area + 28S peak area) vs. (18S peak width + 28S peak width) vs. low C banding region area | 0.8141 |

The three dimensional feature sets were selected for analysis based on the best two dimensional feature set combinations. The three dimensional feature set where the first feature comprises (18S peak area+28S peak area), the second feature set comprises (18S peak width+28S peak width) and the third feature set comprises lower c area was found to have the highest AUC based on the sample study. It has also been found that using three dimensional feature sets increases the spread in the data which makes it easier to discriminate between responders and non-responders.

Accordingly, in one embodiment, the three dimensional feature sets are used in a three dimensional plot using three orthogonal variables representing each feature set to graph an RDA coordinate that is used to discriminate responders from non-responders. One of the variables is defined by a first feature set, another variable is defined by a second feature set and the third variable is defined by a third feature set. These variables may be combined using LDA or QDA as will be described with respect to FIGS. 15A-15D. The first variable comprises the sum of the 18S peak area and the 28S peak area and is associated with a first axis. The second variable comprises the sum of the 18S peak height and the 28S peak height and is associated with a second axis. The third variable comprises the low C banding area and is associated with a third axis. This can be represented by the expression "(18S+28S) vs. (18S peak height+28S peak height) vs. low C banding area".

In another embodiment, the first variable comprises the sum of the 18S peak area and the 28S peak area and is associated with a first axis. The second variable comprises the sum of the 18S peak height and the 28S peak height and is associated with a second axis. The third variable comprises the sum of the 18S peak width and the 28S peak width and is associated with a third axis. This can be represented by the expression "(18S+28S) vs. (18S peak height+28S peak height) vs. (18S peak width+28S peak width)".

In another embodiment, the first variable comprises the sum of the 18S peak area and the 28S peak area and is associated with a first axis. The second variable comprises the sum of the 18S peak height and the 28S peak height and is associated with a second axis. The third variable comprises the intermediate area and is associated with a third axis. This can be represented by the expression "(18S+28S) vs. (18S peak height+28S peak height) vs. intermediate area".

In another embodiment, the first variable comprises the sum of the 18S peak area and the 28S peak area and is associated with a first axis. The second variable comprises the sum of the 18S peak width and the 28S peak width and is associated with a second axis. The third variable comprises the low C band area and is associated with a third axis. This can be represented by the expression "(18S+28S) vs. (18S peak width+28S peak width) vs. low C band area".

Example 14

The following example describes how a selection threshold is determined for a dataset for a selected set of features comprising the combination of features (18S peak area+28S peak area) and (18S peak width+28S peak width), which is showed herein for illustrative purposes only. This procedure can be repeated with other features or combinations of features. It should be noted that the feature sets that are used with LDA or QDA have been normalized with respect to the total area which is the area of the low banding region, the 18S region, the intermediate region and the 28S region.

Figure 15A:
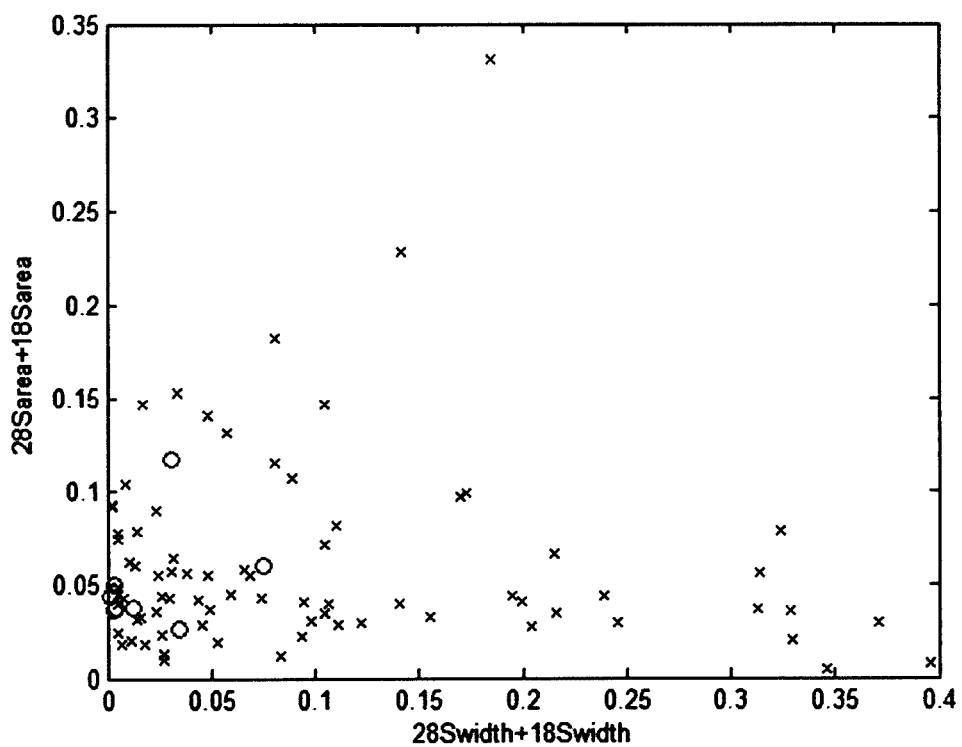
FIG. 15A is a graph of the feature of (28S peak width+18S peak width) versus (28S+18S) for a sample study using the modified peak identification method.

Referring now to FIG. 15A, a first variable representing the 18S peak area+28S peak area was plotted along the x-axis and a second variable representing the 18S peak width+28S peak width was plotted along the y-axis for different patients from the MA22 study. The circles 'O' represent responders and the crosses 'x' represent non-responders in FIG. 15A.

For each threshold value, LDA, which is a classification method, was used to generate values for coefficients that can be used with the first and second variables and the threshold value to define a line that can be used to divide the samples into two groups (i.e. responders and non-responders). This line satisfies equation 3:

$$a \times (18S \text{ peak area} + 28S \text{ peak area}) + b \times (18S \text{ peak width} + 28S \text{ peak width}) - \text{threshold} = 0 \quad (3)$$

where a and b are the coefficient values determined by LDA.

It should be noted that in general, equation 3 can be rewritten as equation 4:

$$y = kx + b \quad (4)$$

in which a feature or a combination of features are used for the variables x and y. In this example, x is (18S area+28S area) and y is (18S width+28S width). The parameter k is the slope of the line which is determined by LDA. The parameter b is the intercept of the line which is the intersection point of the y axis and the line.

Figure 15B:
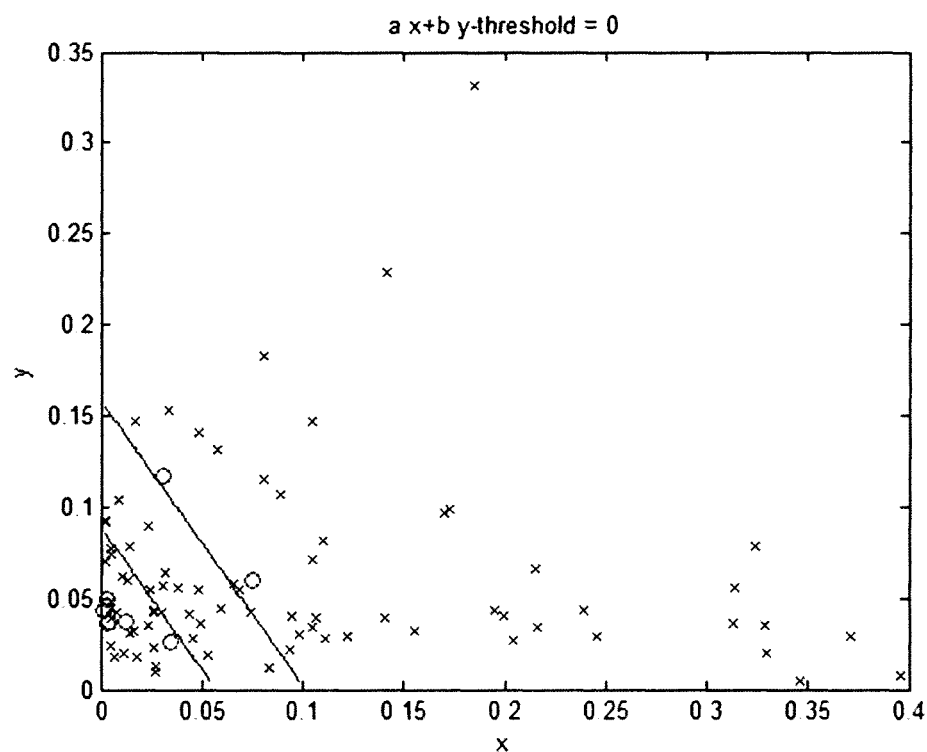
FIG. 15B is the graph of FIG. 15A further comprising Linear Discriminant Analysis (LDA) determined partition lines.

Multiple lines can be determined using multiple threshold values (each threshold value is associated with a line) and these lines can be used to create zones in a plot of the two variables. For example, two lines can be determined for two different threshold values to divide the patients into three zones with two lines. This can be done such that the lines are parallel to one another as is shown in FIG. 15B. The slope of the lines is determined by the LDA and it depends on the actual data samples as well as the combination of features that is used for the different variables.

In order to determine the threshold values, many different threshold values are assessed in terms of one or more predictive or detective measures. For example, for each threshold value, LDA can be used to generate the line and then the samples in the resulting zones can be assessed to determine at least one of the sensitivity, specificity, negative predictive value, positive predictive value, false negative rate and false positive rate associated with the threshold value. The threshold value is then selected based on the one that has the best discriminative or predictive values. For example, the threshold values can be assessed on which threshold value has the best positive predictive value and the negative predictive value.

For each patient, using the two features that are selected as the x and y variable as well as the slope that is determined by LDA analysis, the equation 3 can be used to determine a particular intercept for the patient can be used as the LDA score for the patient.

Figure 15C:
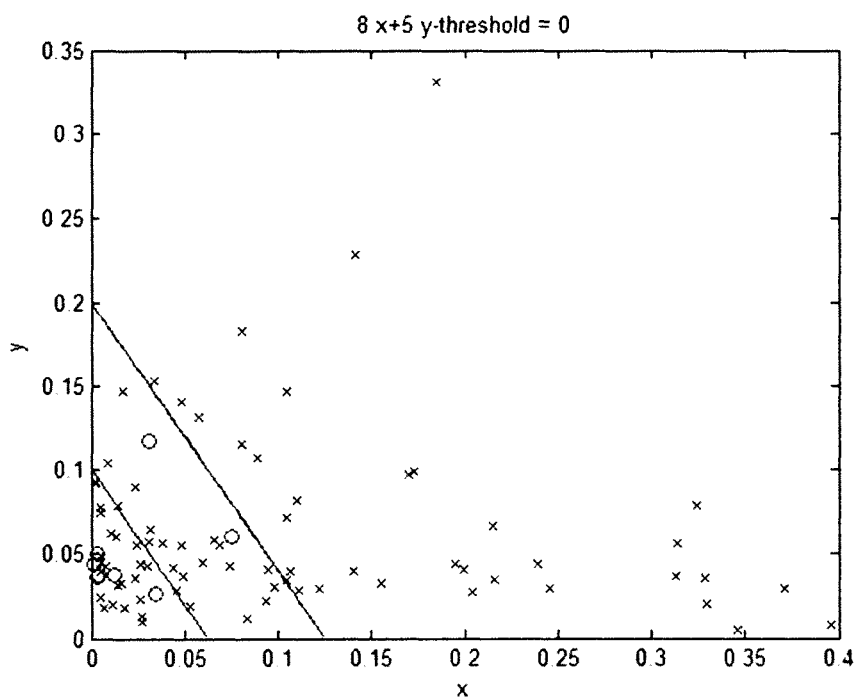
FIG. 15C is the graph of FIG. 15A further comprising another example pair of LDA determined partition lines.

For example, assume 0.1 and 0.2 are selected as the y-intercept to define the zone-partitions. The patients can then be divided into three zones as shown in FIG. 15C. The uppermost line is given by the equation y=−1.6x+0.2 (or 8x+5y=1) and the lowermost line is given by the equation y=−1.6x+0.1 (or 8x+5y=0.5). The x-axis and y-axis variables are (18S peak area+28S peak area) and (18S peak width+28S peak width), respectively.

The region underneath the lowermost line, above the x axis and to the right of the y axis defines zone 1 in which there are 29 patients, 6 of which are responders. The region between the uppermost and lowermost lines and to the right of the y axis defines zone 2 in which there are 22 patients, 2 of which are responders. The region above the uppermost line and to the right of the y-axis define zone 3 in which there are 34 patients, all of which are non-responders.

Example 15

In an alternative embodiment, rather than using LDA to determine RDA zones as was done in FIGS. 15B and 15C, Quadratic Discriminant Analysis (QDA) can be used to determine partitions for the zones that can be used for prediction. With different thresholds, QDA gives different curves to divide the samples into various groups. For example, using two threshold values two groups, satisfying the following equation 5:

$$c_1 \times (18S \text{ peak area} + 28S \text{ peak area})^2 + \quad (5)$$
$$c_3 \times (18S \text{ peak width} + 28S \text{ peak width})^2 +$$
$$c_2 \times (18S \text{ peak area} + 28S \text{ peak area}) \times$$
$$(18S \text{ peak width} + 28S \text{ peak width}) +$$
$$a_1 \times (18S \text{ peak area} + 28S \text{ peak area}) +$$
$$b_1 \times (18S \text{ peak width} + 28S \text{ peak width}) - \text{threshold} = 0$$

where a first variable represents the feature 18S peak area+28S peak area and a second variable represents the feature 18S peak width+28S peak width and the parameters $a_1$, $b_1$, $c_1$, $c_2$ and $c_3$ are determined by QDA.

Figure 15D:
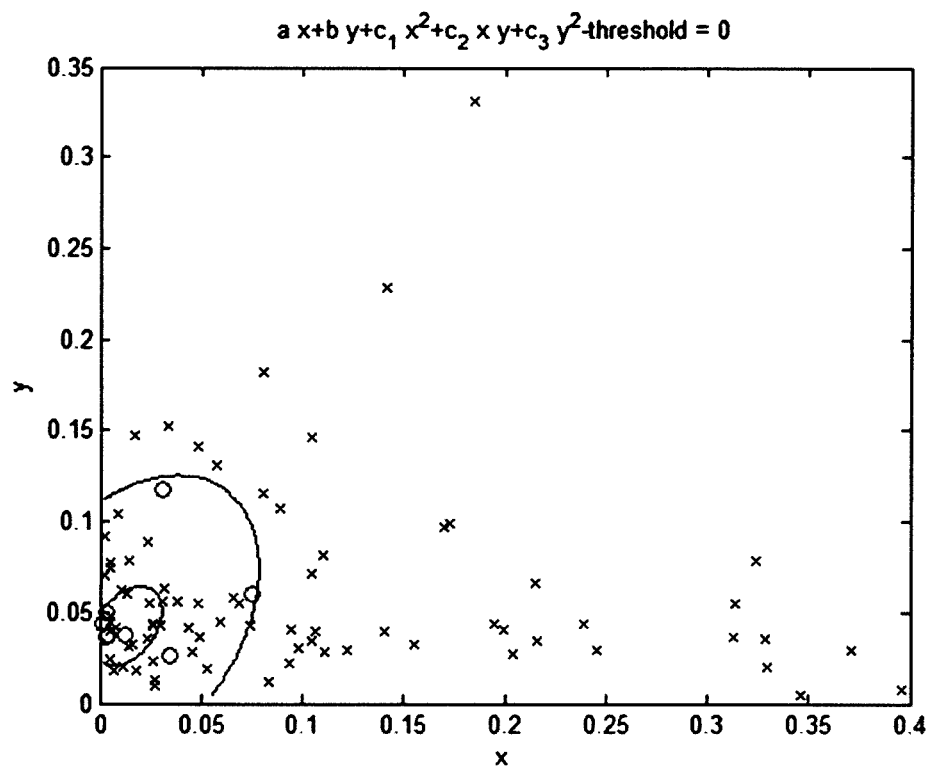
FIG. 15D is the graph of FIG. 15A further comprising Quadratic Discriminant Analysis (QDA) determined partition lines.

Equation 4 can be used with two thresholds to generate two concentric curves that can divide the patients into three zones as shown in FIG. 15D. Once again, the circles 'O' represent responders, and the crosses 'x' represent non-responders. The appropriate threshold values can be determined as was explained previously using LDA, namely that for several threshold values the predictive measures of sensitivity, specificity, negative predictive value, positive predictive value, false negative rate and false positive rate can be calculated for each threshold. The desired threshold values can then be selected which result in the best predictive values.

For combinations of three features, the same analysis can be used to determine the RDA zones using either LDA or QDA.

It should be noted that in alternative embodiments, other techniques may be used to determine the RDA zones. For example, other machine learning methods may be used to do the prediction where there is a larger dataset such as, but not limited to, Support Vector Machine (SVM), Neural Networks, and the k-nearest neighbors algorithm (kNN).

Example 16

RDI

The RNA Disruption index (RDI) is the output of an RDA assay described herein, for example a value corresponding to a ratio of at least some of the various combinations of features described herein or the result of LDA or quadratic discriminant analysis of at least two of the feature sets described herein. The cutoff point between zone 2 and zone 3 may be chosen to maximize the PPV such that most of the responders from the MA22 dataset would be located in zone 3. For example, the RDI ranges used based on the study samples are about: 0.3 to 10 (zone 1), 10.1 to 35 (zone 2) and greater than 35.1 (zone 3). There may be other zones in other situations. For example, the fragmented RNA can be determined by the sum of the intermediate region area and the low C region area. This index can be used to compare samples for the extent of RNA disruption, for example for research purposes. Clinical zones can be established which capture a range of RDI values wherein the clinical zones are defined by cutoff points (e.g. between zone 1 and 2 and between zone 2 and 3). For example the cutoff point between zone 1 and zone 2 can be set to correspond to a RDI value that gives an NPV of 0.99.

Example 17

The data described in Example 6 was reanalyzed using the peak identification method 400 described in Example 10.

Plots of the combination of features Intermediate Area/(28S+18S) and Low C Area/(28S+18S) were generated using the method 400 although method 300 may also be used.

The ratio of Low C Area/(28S+18S) was plotted against docetaxel dose. Little change was seen at 8 hr, 24 hr, or 48 hr. However, after 72 hr, a dramatic increase in the sample. Two replicate experiments had similar results.

Figure 16A:
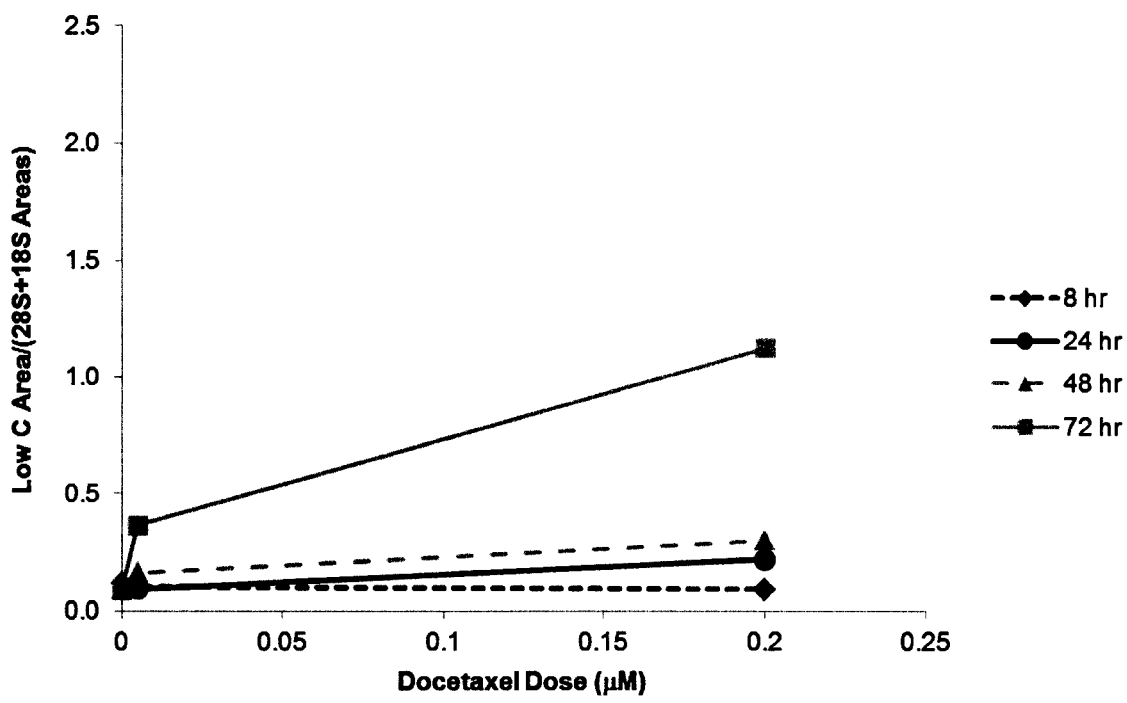
FIG. 16A is a graph of the feature low C/(28S+18S) versus docetaxel dose for an in vitro study using the modified peak identification method.
Figure 16B:
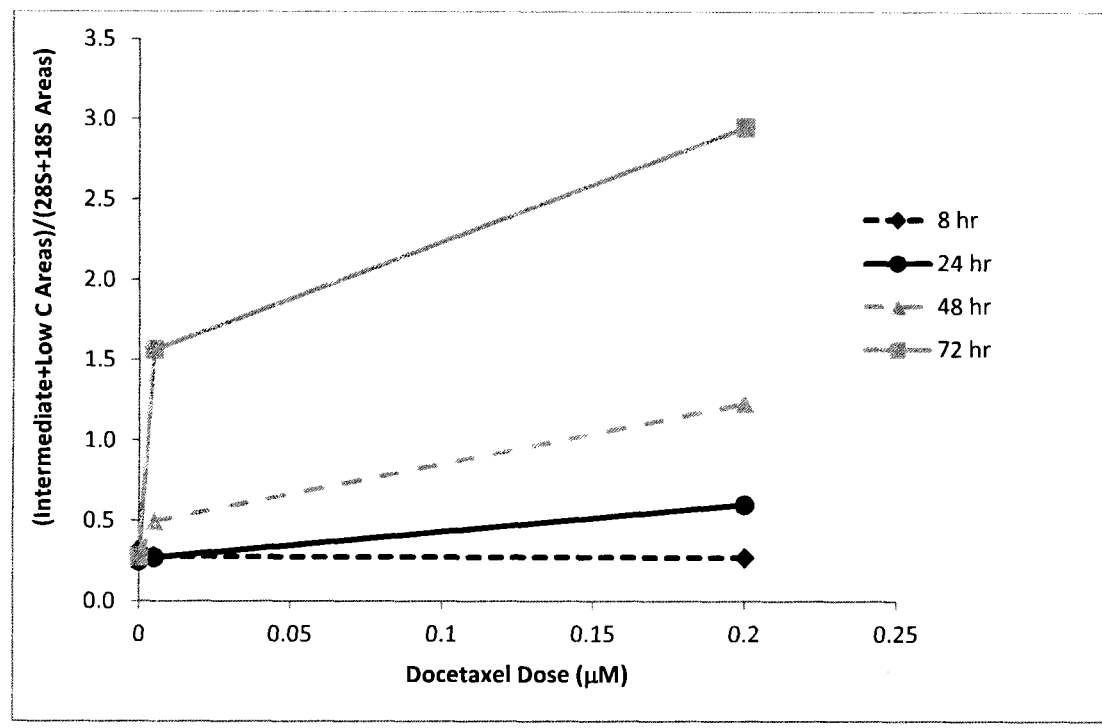
FIG. 16B is a graph of the feature (Intermediate+low C)/(28S+18S) versus docetaxel dose for an in vitro study using the modified peak identification method.

The maximum of the ratio (Intermediate Area+Low C Area)/(28S+18S) was plotted against docetaxel dose and the results are shown in FIG. 16B. Each value represents a single sample. Two replicate experiments had similar results.

Example 18

Figure 17A:
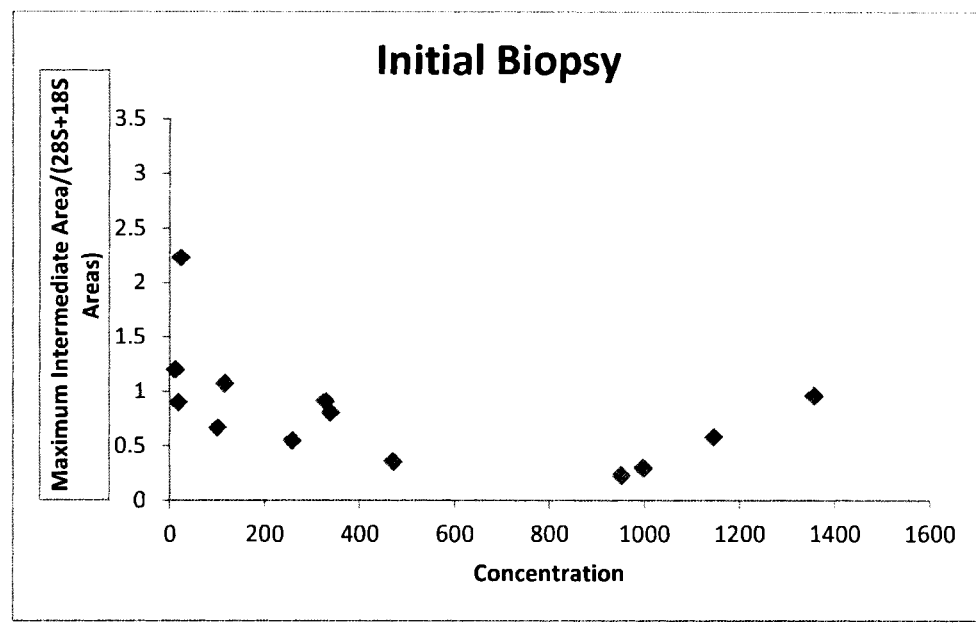
FIG. 17A is a graph of the feature Maximum Intermediate/(28S+18S) versus RNA concentration for a sample study for patients undergoing neo-adjuvant therapy with Trastuzumab.
Figure 17B:
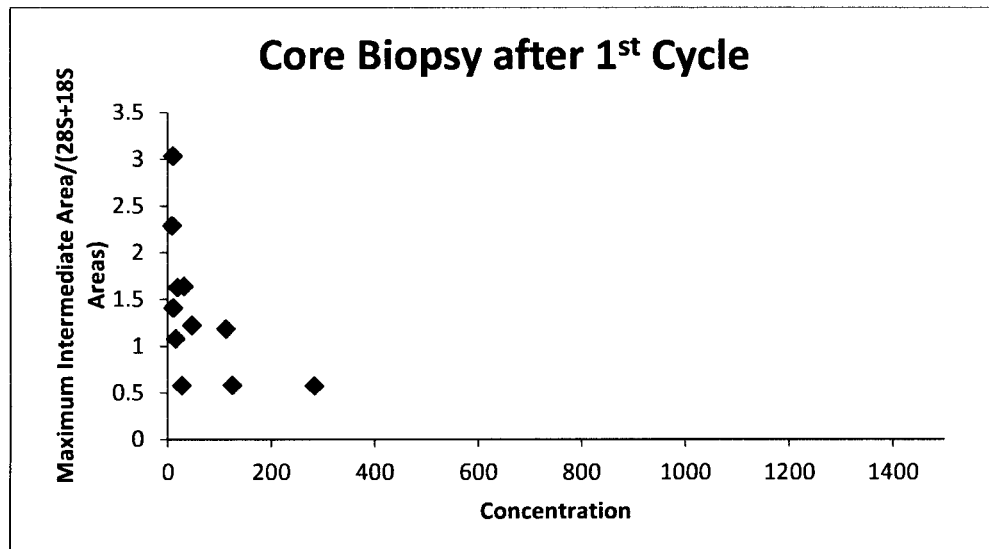
FIG. 17B is a graph of the feature Maximum Intermediate/(28S+18S) versus RNA concentration for a sample study for patients undergoing neo-adjuvant therapy with Trastuzumab.

Biopsy samples before and after a treatment dose were obtained from patients undergoing neo-adjuvant therapy with Trastuzumab. RNA was isolated and analyzed using the Agilent Bioanalyzer. Electropherograms were analyzed using the methods 100 and 400 and the maximal RDI score was graphed for each tumour sample at each time-point. The RDI values are increased in some patients after the first cycle of Trastuzumab (FIG. 17A and FIG. 17B).

Figure 17C:
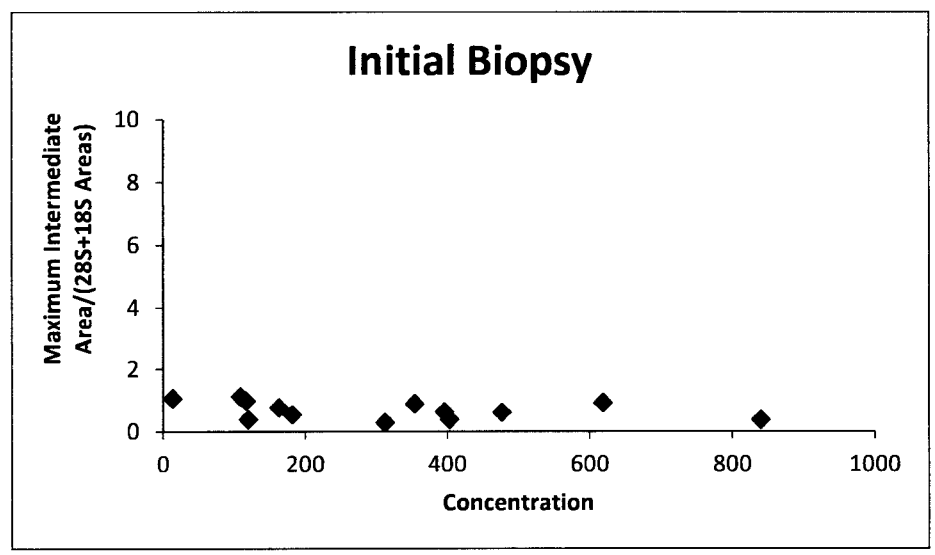
FIG. 17C is a graph of the feature Maximum Intermediate/(28S+18S) versus RNA concentration for a sample study for patients undergoing neo-adjuvant therapy with Zometa.
Figure 17D:
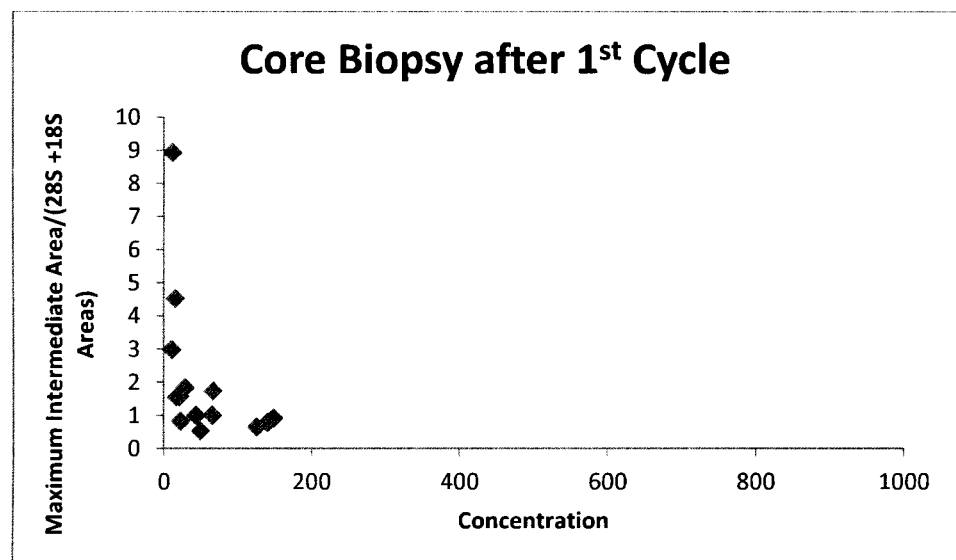
FIG. 17D is a graph of the feature Maximum Intermediate/(28S+18S) versus RNA concentration for a sample study for patients undergoing neo-adjuvant therapy with Zometa.
Figure 18A:
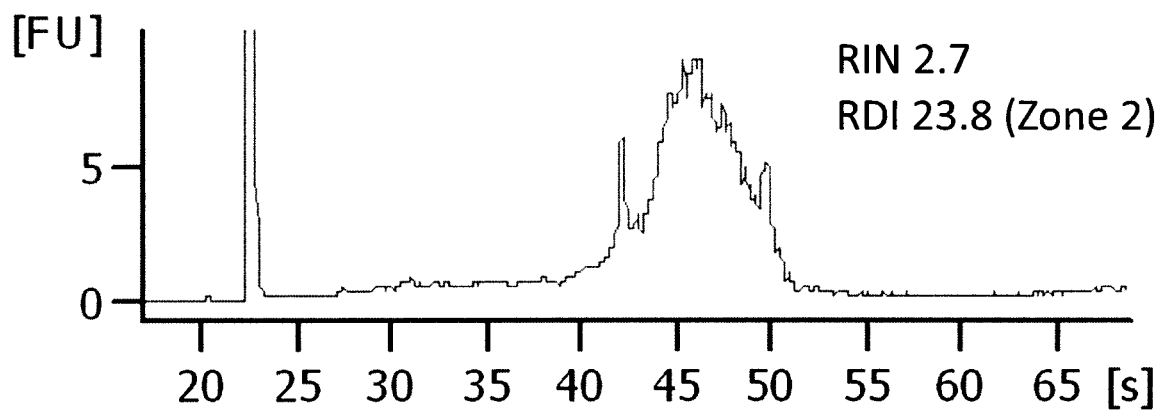
FIGS. 18A-18F are a series of illustrations of electropherogram traces with the calculated RIN and RDI values for each.
Figure 18B:
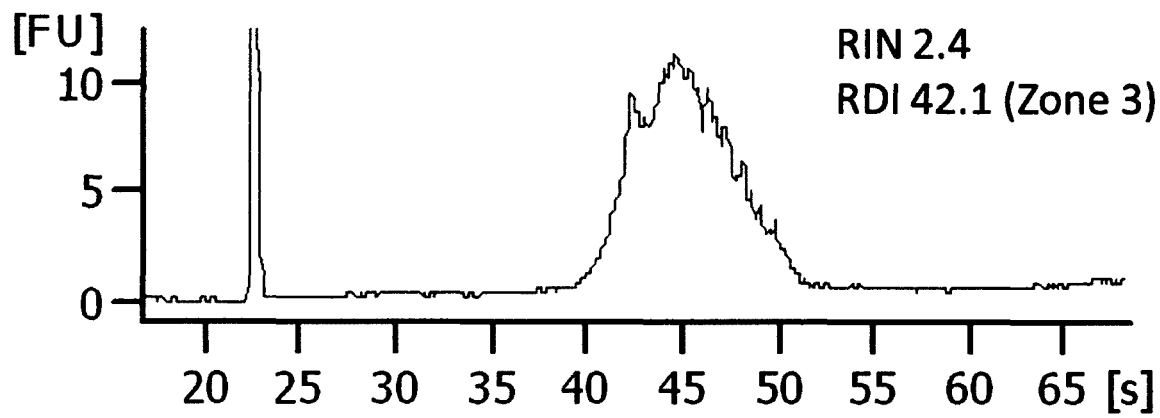
Figure 18C:
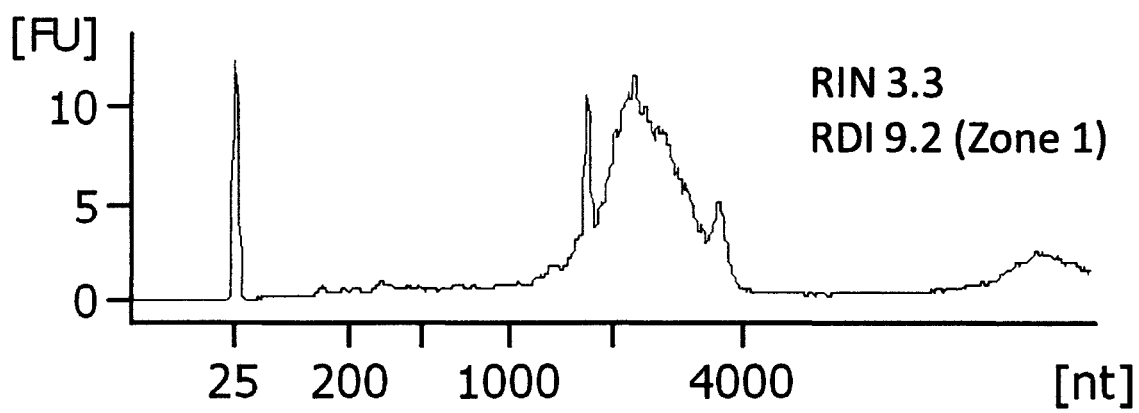
Figure 18D:
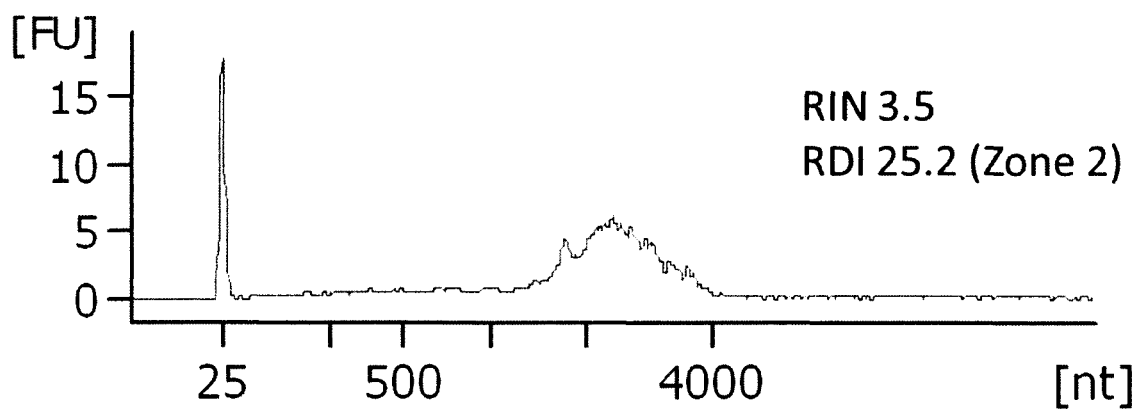
Figure 18E:
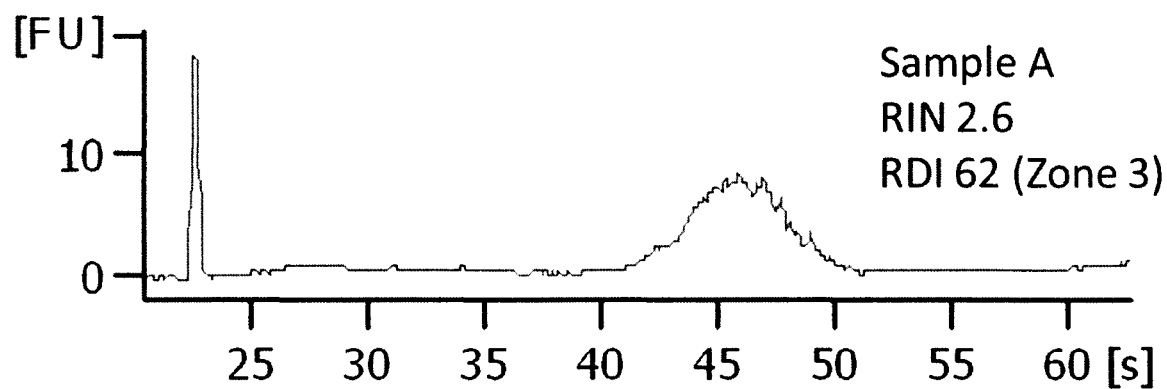
Figure 18F:
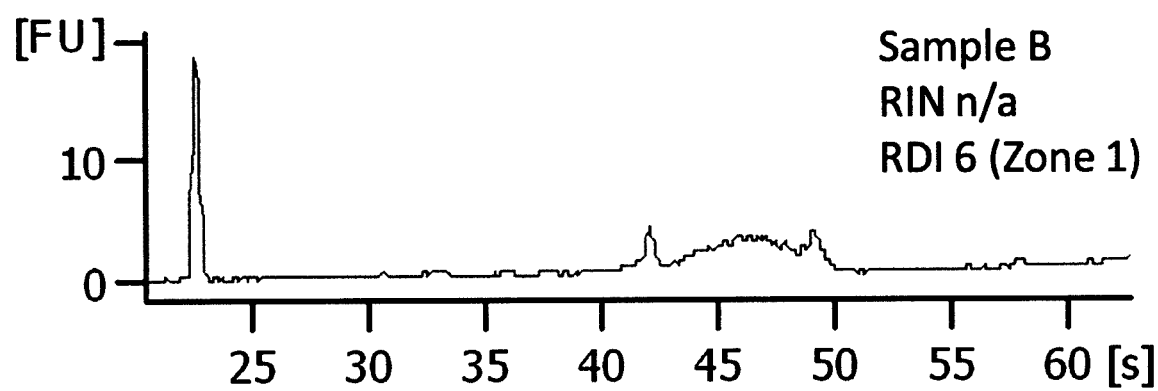

Biopsy samples were obtained from patients undergoing neo-adjuvant therapy with Zometa. RNA was isolated and analyzed using the Agilent Bioanalyzer. Electropherograms were analyzed using the methods 100 and 400 and the maximal RDI score was graphed for each tumour sample at each time-point. The RDI values are increased in some patients after the first cycle of Zometa (FIG. 17C and FIG. 17D).

Example 19

FIGS. 18A-18F show several samples where the RIN algorithm gives a low RIN or "n/a" whereas the RDI score, determined as described herein, is better able to differentiate these samples. The electropherograms of FIGS. 18A-18F were taken from mid-therapy MA22 data. FIGS. 18A-18F also show that RIN values can be the same in electropherograms which demonstrate different patterns whereas the RDI score appears to be able to differentiate between these electropherograms. The RDI was calculated using the ratio or feature combination Intermediate Area/(28S+18S Areas).

Figure 19:
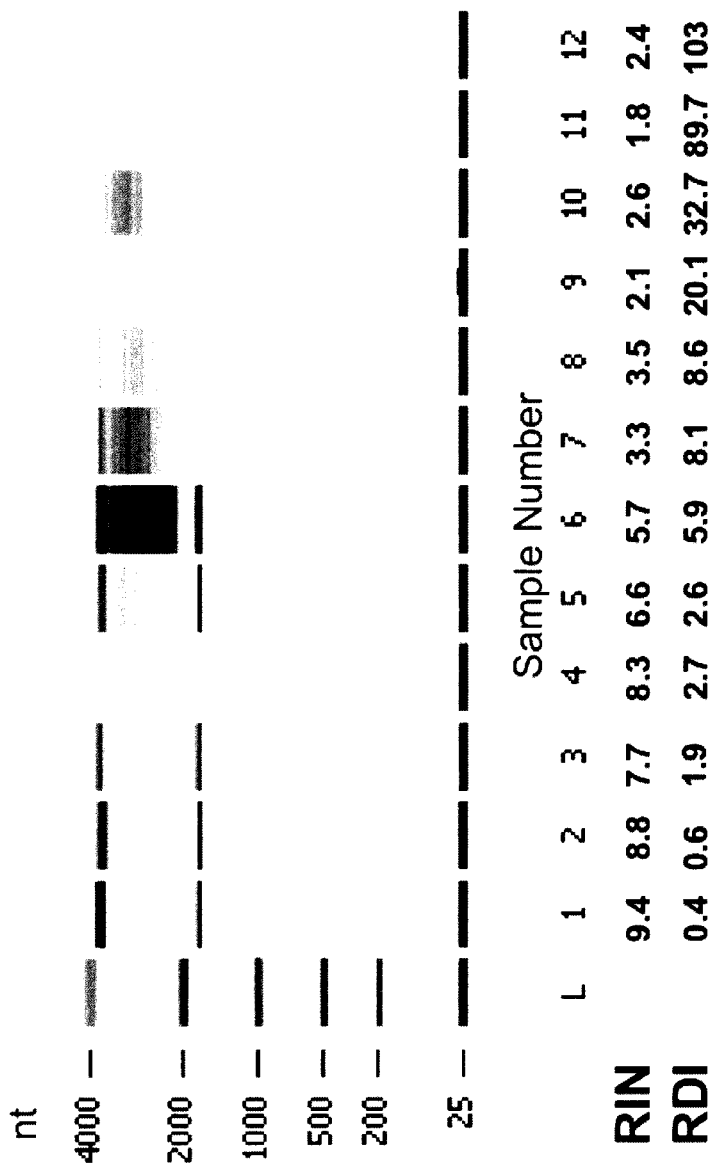
FIG. 19 is an image of a gel of electrophoretically separated RNA samples and corresponding RIN and RDI values for each sample.

FIG. 19 compares RIN to RDI in mid-therapy MA22 samples. When the RNA is intact, both the RIN and RDI scores are accurate. However, once the RNA becomes fragmented, for example due to drug exposure, the RDI is a better measure. The feature combination that was used for the RDI determination was Intermediate Area/(28S+18S).

Example 20

The need for biomarkers to accurately assess long term breast cancer chemotherapy efficacy is well established and is particularly needed for triple negative breast cancer (TNBC). To date, most in vitro diagnostic tests offered have been limited to hormone receptor positive patients. The RNA Disruption Assay (RDA), described herein, is a novel prognostic test for patients undergoing neoadjuvant chemotherapy that enables assessment of drug efficacy during treatment. RDA was developed in association with the CAN-NCIC-CTG MA-22 clinical trial for women with locally advanced breast cancer. Varying doses of docetaxel and epirubicin were given at two weekly (dose dense) or three weekly intervals. Tumours were biopsied in duplicate at three time points: pre-therapy, mid-therapy and post-therapy. Trial endpoints included clinical response, pathological complete response (pCR), disease-free survival and overall survival.

RDA is based on RNA electropherogram analysis generated to assess RNA quality as measured by the extent of ribosomal RNA (rRNA) disruption, mid-therapy. rRNA Disruption is quantified by a method described herein for example as described in FIGS. 5A and 5B or 12A and then stratified into an RNA Disruption Assay (RDA) score with 3 zones corresponding to the degree of RNA disruption. An RDA score in Zone 3 is associated with an increased likelihood of subsequent pathological complete response, an RDA score in Zone 2 is associated with an increased likelihood of at least partial response, and an RDA score in Zone 1 indicates that patients are very unlikely to receive long term chemotherapy benefit, NPV>0.98, for example.

When applied to the MA-22 study after the $3^{rd}$ or $4^{th}$ cycle of chemotherapy, 34 of 85 patients (40%) had tumours with RDA scores in zone 1.

Subsequently, it has been demonstrated in tumour cell lines that rRNA disruption leads directly to subsequent tumour cell death and that the extent of rRNA disruption is cell line type, dose, and time dependent.

Methods

Paraffin-embedded, formalin-fixed tumours from 82 MA-22 patients were subtyped by immunohistochemistry for estrogen receptor (ER), progesterone receptor (PR) and Her2/neu (Her2) expression status pre-therapy.

RDA, clinical response data and pCR occurrence data were obtained for each patient and matched to the tumour expression status for the above receptors. The feature combination that was used for the RDA determination was Intermediate Area/(28S+18S). The TNBC patients' tumours were then assessed for RNA disruption (RDA zones 1, 2 or 3) and compared to similar data for receptor positive patients. A similar comparison was made classifying patients by clinical response (e.g. no response/stable disease, partial response, or complete clinical response).

Results

Both Triple Negative Breast Cancer (TNBC) patients and receptor positive patients had tumours in each of the three RDA zones and in each of the clinical response categories. The pCR response rates were 3 of 21 (14% response rate) for TNBC patients, 0 of 43 (0% response rate) for ER+, Her2−ve patients, 1 of 6 (17% response rate) for ER+, Her2+ patients, and 4 of 12 (33% response rate) for Her2+ patients. Six of eight pCR responders were in RDA Zone 3 and two were in RDA Zone 2. Clinically, 6 of 8 pCR responders had a complete response, and two had partial responses. For the three TNBC clinical non responders who had stable disease, the RDA scores were in RDA Zone 3 for one patient, RDA Zone 2 for the second patient and RDA Zone 1 for the third. Seven of 18 non-responder TNBC patients were in RDA Zone 1. However, clinically, five of these patients had a partial response, one had a complete response and one had stable disease. Two of the three TNBC pCR responders showed an RDA score in RDA Zone 3 but clinically one had a partial response. For other subtypes, 12 of 44 ER+, Her2−ve patients were in RDA Zone 1; 3 of 6 Er+ve, Her2+ve patients were in RDA Zone 1; 2 of 12 Her2+ve patients were in RDA zone 1. Using pCR and non pCR as definitive criteria, RDA was equally predictive with clinical response for prediction of complete response but was much superior for prediction of pCR non-response.

Conclusions

In both TNBC and other subtypes of locally advanced breast cancer, RDA can identify pCR non-responders much better than clinical response. Currently, based on this study, RDA can identify approximately 33% of TNBC patients as non-responders compared to approximately 28% for ER+ve Her2−ve patients. These results indicate that RDA, as a test for response guided therapy, can identify a subpopulation of non-responding TNBC patients who can be considered for alternate therapy.

Example 21

One major obstacle to the successful destruction of tumors using chemotherapy drugs is the presence of intrinsic or acquired resistance to anti-cancer agents. Assessed herein is whether chemotherapy-dependent alterations in tumor RNA quantity and integrity could also be demonstrated in vitro using the A2780 ovarian cancer cell line. An equal number of cells were plated and treated with various doc-etaxel concentrations to determine the effect of the drug on cell division, cellular RNA content, and RNA integrity. At low docetaxel concentrations, RNA content increased per cell, likely due to increased rRNA production prior to a cell cycle arrest at mitosis. However, at higher docetaxel concentrations (≥0.1 µM), dose and time-dependent reductions in cell number and cell RIN values were observed while the RDI based on the feature combination of Intermediate Area/(28S+18S) increased, which coincided with dramatic changes in the RNA banding pattern (i.e. RNA disruption). This included the formation of novel discrete bands distinct from the 28S and 18S rRNA bands. In contrast, treating docetaxel-resistant A2780DXL cells with docetaxel did not result in RNA disruption or changes in cellular RNA content. These findings support the view that chemotherapy dependent changes in tumor cell RNA content and integrity (as measured using the RNA disruption assay or RDA technique described herein) could effectively be used to monitor cellular response to chemotherapy agents and to differentiate between drug-sensitive and drug-resistant tumor cells in vitro and in vivo.

Example 22

Figure 20A:
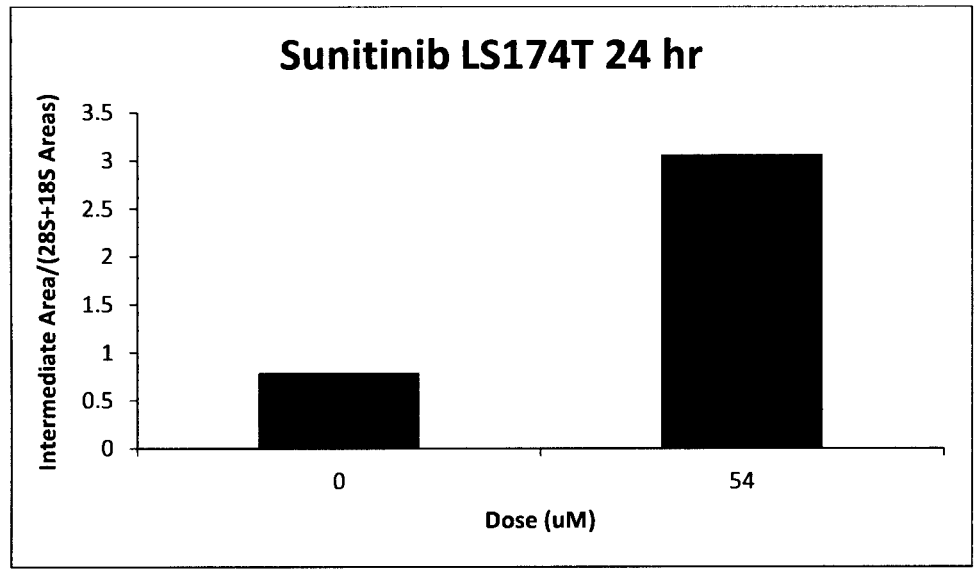
FIG. 20A is a graph of the feature Intermediate Area/(28S+18S Areas) for colon adenocarcinoma cells incubated with Sunitinib.

Colon adenocarcinoma cells LS174T were incubated with Sunitinib, a receptor tyrosine kinase inhibitor. RNA was isolated from the cells and analyzed using an Agilent Bio-analyzer. RNA Disruption is evident at 24 hr at 54 mM (see FIG. 20A).

Figure 20B:
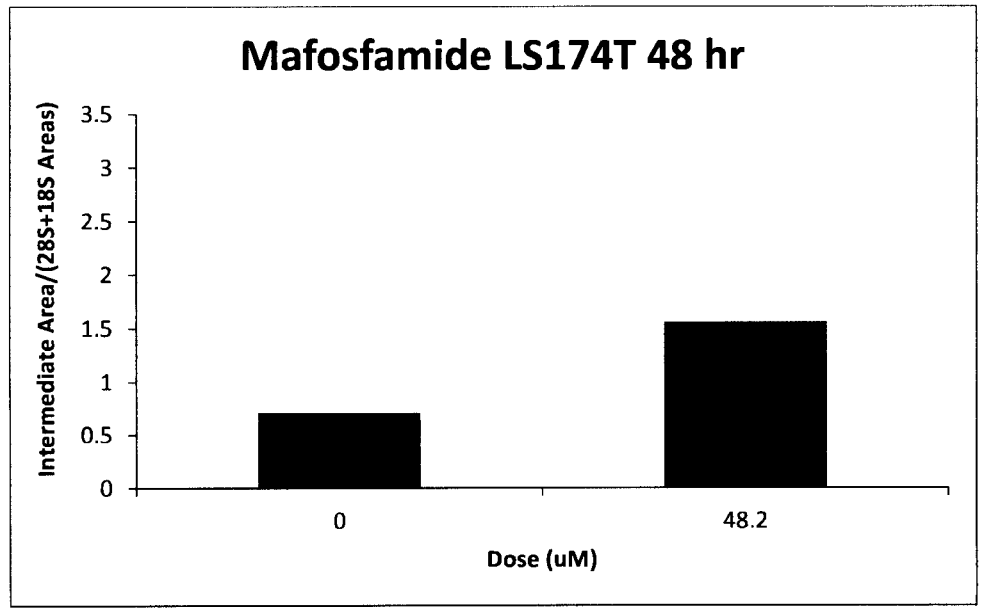
FIG. 20B is a graph of the feature Intermediate Area/(28S+18S Areas) for colon adenocarcinoma cells incubated with Mafosfamide.

Colon adenocarcinoma cells LS174T were incubated with Mafosfamide, a DNA cross-linking agent. RNA was isolated from the cells and analyzed using an Agilent Bioanalyzer. RNA Disruption is evident at 48 hr at 48.2 mM (see FIG. 20B).

Figure 20C:
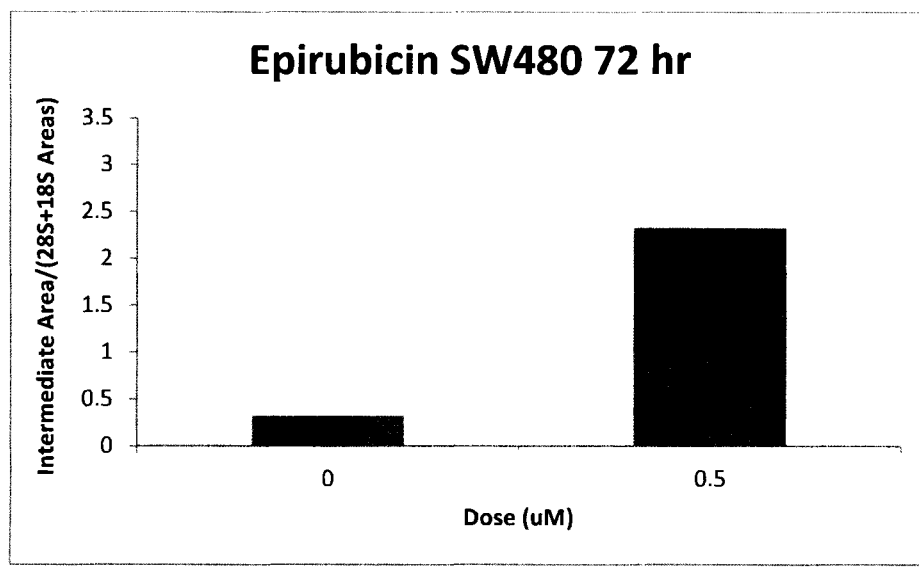
FIG. 20C is a graph of the feature Intermediate Area/(28S+18S Areas) for colon adenocarcinoma cells incubated with Epirubicin.

Colon adenocarcinoma cells SW480 were incubated with Epirubicin, a DNA synthesis inhibitor. RNA was isolated from the cells and analyzed using an Agilent Bioanalyzer. RNA Disruption is evident at 72 hr at 0.5 mM (see FIG. 20C).

It should be noted that either method 300 or method 400 can be used in determining the values for the combinations of features or the feature sets used in LDA and QDA analysis.

While the applicant's teachings described herein are in conjunction with various embodiments for illustrative purposes, it is not intended that the applicant's teachings be limited to such embodiments. On the contrary, the applicant's teachings described and illustrated herein encompass various alternatives, modifications, and equivalents, without departing from the embodiments, the general scope of which is defined in the appended claims.

All publications, patents and patent applications are herein incorporated by reference in their entirety to the same extent as if each individual publication, patent or patent application was specifically and individually indicated to be incorporated by reference in its entirety. Specifically, the sequences associated with each accession number provided herein including, for example, accession numbers and/or biomarker sequences (e.g. protein and/or nucleic acid) provided in the Tables or elsewhere, are incorporated by reference in its entirely.

CITATIONS FOR REFERENCES REFERRED TO IN THE SPECIFICATION

Brackstone et al *Cancer Res* 2012; 72(24 Suppl): Abstract nr P1-14-13.
Cappallo-Obermann, H., W. Schulze, et al. (2011). "Highly purified spermatozoal RNA obtained by a novel method indicates an unusual 28S/18S rRNA ratio and suggests impaired ribosome assembly." *Molecular Human Reproduction* 17(11): 669-678.
Fimognari C; Sestili P et al (2009) Protective effect of creatie against RNA damage *Mutation Researach* 670:59-67
Hurley, J. (2011). "Meta-analysis of clinical studies of diagnostic tests: developments in how the receiver operating characteristic "works"." *Arch Pathol Lab Med* 135 (12): 1585-1590.
Li et al., Int. J. Mol. Med 2004 14(20): 257-264.
Mori, N., D. i. Mizuno, et al. (1978). "Increase in the ratio of 18S to 28S RNA in the cytoplasm of mouse tissues during aging." *Mechanisms of Ageing and Development:* 285-297.
Mueller, O. L., S.; Schroeder, A (2004) RNA Integrity Number (RIN)—Standardization of RNA Quality Control.
Parissenti, A. M., J.-A. W. Chapman, et al. (2010). "Association of low tumor RNA integrity with response to chemotherapy in breast cancer patients." *Breast Cancer Res Treat* 119: 347-356.
Schroeder, A., O. Mueller, et al. (2006). "The RIN: an RNA integrity number for assigning integrity values to RNA measurements." *BMC Mol Biol* 7: 3.
Skrypina, N. A., A. V. Timofeeva, et al. (2003). "Total RNA suitable for molecular biology analysis." *Journal of Biotechnology* 105: 1-9.
Vespucci, U. G. (2005). Agilent 2100 Bioanalyzer, Agilent Technologies, Inc. 2100 Expert User's Guide. Agilent Technologies Hewlett-Packard Str. 8 76337 Waldbronn Germany, Agilent Technologies, Inc. Agilent2100 G2946-90004_Vespucci_UG_eBook_(NoSecPack)[2].

The invention claimed is:

1. A method for treating a subject with cancer wherein the method comprises:
   a) treating the subject with a cytotoxic treatment selected from a chemotherapeutic, a neo-adjuvant hormonal, a cytotoxic antibody and/or a radiation treatment regimen;
   b) obtaining a unique biological sample comprising cellular ribonucleic acids (RNA) from the subject after having been treated with the cytotoxic treatment, the cytotoxic treatment selected from a chemotherapeutic, neo-adjuvant hormonal, cytotoxic antibody and/or radiation treatment regimen;
   c) separating the cellular RNA by electrophoresis, detecting a quantity of the separated cellular RNA, plotting the quantity of separated cellular RNA and obtaining at least one electropherogram dataset from the electropherogram plot;
   d) obtaining a plurality of electropherogram datasets including the at least one electropherogram dataset from a data input device, the plurality of electropherogram datasets corresponding to a plurality of unique biological samples comprising cellular RNA;
   e) employing a processor that is coupled to the data input device, wherein the processor is configured to analyze the plurality of electropherogram datasets by:
      e-i) defining two identifying ranges by initializing the identifying ranges to default ranges, and
         e-i-1) performing shifting when a marker region is not at an expected location, where the expected location is a time associated with a first peak that is a dye-only peak that indicates a start of a run of a gel during the electrophoresis for obtaining the at least one electropherogram dataset and the shifting is done so that the two identifying ranges include a shifted 18S peak and a shifted 28S peak, respectively, which are an 18S rRNA peak and a 28S rRNA peak, respectively, or
         e-i-2) maintaining the two identifying ranges at the default ranges when the marker region is at the expected location; e-ii) identifying the 18S peak and 28S peak by selecting from possible peak candidates in the two identifying regions where the possible peak candidates are identified by searching for local maximums in the at least one electropherogram;
      e-iii) calculating values including one or more of a peak height, a peak width and a peak position based on the identified 18S peak and 28S peak;
      e-iv) identifying a standard sample from the plurality of electropherogram datasets using the values calculated from the identified 18S peak and 28S peak and area values for neighboring regions, where the standard sample is a sample of intact RNA or approximately intact RNA after treatment;
      e-v) separating the plurality of electropherogram datasets into an adjustment group and a standard group by comparing retention times for both the 28S peak and the 18S peak of the electropherogram dataset of the standard sample with retention times of the 28S peak and the 18S peak of the electropherogram datasets of the other samples;
      e-vi) identifying normal characteristics representative of the standard sample from the plurality of electropherogram datasets in the standard group, the normal characteristics comprising the retention times for the 18S peak and the 28S peak from samples in the standard group which are defined as standard retention times;
      e-vii) determining locations of the 18S peak and the 28S peak for the electropherogram datasets in the adjustment group by determining retention times for the 18S and 28S peaks of the electropherograms in the adjustment group where these peaks have areas that include the standard retention times for the 18S and 28S peak;
      e-viii) determining an intermediate region and a low C banding region for the electropherogram datasets in the adjustment group after locating the 18S peak and the 28S peak in the adjustment group, where the intermediate region is between the located 18S peak and the located 28S peak and the low C banding region is an upper portion of a low banding region below the 18S peak and adjacent to the 18S peak;
      e-ix) determining values for features from the electropherograms from the adjustment group after locating the 18S peak and the 28S peak from the electropherograms from the standard group, the features comprising at least one of intermediate region area and low C banding region area, and at least one of 28S peak area, and 18S peak area;
      e-x) determining an RNA disruption assay (RDA) score based on a ratio using the values of the features, the RDA score being indicative of the extent of treatment induced RNA degradation; and
      e-xi) outputting the RDA score to a data output device that is coupled to the processor;
   f) assessing response to the cytotoxic treatment by comparing the RDA score to at least one threshold value or at least one threshold curve to determine when the subject is a responder or a non-responder to the cytotoxic treatment; and
   g-i) continuing administration of the cytotoxic treatment when the subject is determined to be a responder; or
   g-ii) switching the cytotoxic treatment when the subject is determined to be a non-responder, wherein switching the cytotoxic treatment comprises increasing a dose of the cytotoxic treatment administered, adding one or more of radiation and a chemotherapeutic agent to the cytotoxic treatment regimen, discontinuing the cytotoxic treatment and initiating a different cytotoxic treatment regimen.

2. The method of claim 1, wherein the default ranges for the identifying ranges are [39.5 seconds, 44.95 seconds] and [45.05 seconds, 53.5 seconds] for the 18S and 28S peaks respectively, the marker region occurs in time before the low banding region in the electropherogram plot, the marker time is about 22.5 seconds, rngshft is a shift factor determined according to rngshft=marker time −22.5 and step (e-i-1) comprises shifting the default range for the identifying range for the 18S peak according to [39.5+rngshft×1.5, 44.95+rngshft×1.5] and shifting the default range for the identifying range for the 28S peak is shifted according to [45.05+rngshft×2.5, 53.5+rngshft×2.5].

3. The method of claim 1, wherein the 18S peak and the 28S peak are identified and located by first locating the possible peak candidates in the two identifying ranges, calculating height differences of each possible peak candidate, and defining the 18S peak and the 28S peak as the two largest peak candidates; wherein a height difference of a given peak candidate is defined as a difference of a highest peak value and an average of lowest peak values for the given peak candidate where the low peak values that are averaged are a starting point and an ending point associated with the highest peak value.

4. The method of claim 1, wherein:
  i) the standard sample has a smallest standard score defined by a ratio of a sum of intermediate area, low B banding region area and the low C banding region area to a sum of the 18S peak area and the 28S peak area;
  ii) identifying the normal characteristics comprises defining the standard retention times by a statistical measure of corresponding retention times for electropherograms in the standard group, wherein the statistical measure comprises one of a median and a mean;
  iii) the plurality of electropherogram datasets are derived from the unique biological sample on an RNA chip; and/or
  iv) the RDA score is compared to at least two RDA zones where each of the RDA zones is defined by one or two boundaries that each correspond to a selected threshold corresponding to a desired Negative Predictive Value (NPV) or a desired Positive Predictive Value (PPV) of treatment response, or wherein the RDA score comprises an RDI score, wherein each RDA zone is a clinical zone associated with treatment response outcome comprising a range of RNA disruption scores and RDI is a ratio of features analysed.

5. The method of claim 1, wherein:
  i) the features are used to define a ratio of the low C banding region area to a sum of the 18S peak area and the 28S peak area;
  ii) the features are used to define a ratio of the sum of the low C banding region area and the intermediate area to the sum of the 28S peak area and the 18S peak area;
  iii) the features are used to define a maximum ratio determined from at least two electropherogram datasets, wherein the ratio is defined as an intermediate area divided by the sum of the 18S peak area and the 28S peak area;
  iv) the features are used to define a ratio of low C banding region area to a sum of the 18S peak area and the 28S peak area; and/or
  v) the features are used to define a ratio of intermediate area to a sum of the 28S peak area and the 18S peak area.

6. The method of claim 1, wherein a peak area for a given peak is defined by an area between two local minimum values on either side of the given peak.

7. The method of claim 1, wherein the electrophoresis comprises microcapillary gel electrophoresis; or wherein the electrophoresis comprises using an RNA chip comprising microchannels for electrophoretically separating the RNA of a given sample.

8. The method of claim 1, wherein the method further comprises comparing the RDA score to more than one threshold where each threshold corresponds to an RDA zone boundary to determine effectiveness of the treatment where the RDA zone boundary defines two RDA zones that each correspond to a selected threshold corresponding to a desired Negative Predictive Value (NPV) or a desired Positive Predictive Value (PPV) of treatment response.

9. The method of claim 8, wherein one of the thresholds corresponds to a selected negative predictive value (NPV) and defines a boundary between an RDA zone 2 and an RDA zone 3 and another of the thresholds corresponds to a selected positive predictive value (PPV) and defines the boundary between an RDA zone 1 and the RDA zone 2.

10. The method of claim 1, wherein for performing the RNA Disruption Assay (RDA) for cellular RNA the method comprises:
  determining at least one parameter value for a given 18S peak and a given 28S peak; wherein the at least one parameter value comprises at least one of a given peak area, a given peak width and a given peak location; and
  redefining at least one of the given 18S peak and the given 28S peak only when:
    (a) at least one of the given 18S peak and the given 28S peak have more than one maximum value based on the given peak area;
    (b) widths of the given 18S peak and the given 28S peak require adjustment to be in a predefined width range; or
    (c) a location of at least one of the given 18S peak and the given 28S peak requires adjustment only when a distance between the given 18S peak and the given 28S peak is greater than a distance threshold.

11. The method of claim 1, wherein the data input device comprises at least one of an electropherogram device, a data interface, a wireless module, I/O hardware, and a memory.

12. The method of claim 1, wherein the data output device comprises at least one of a display, a wireless module, a data interface, and a memory.

* * * * *